US010688119B2

(12) United States Patent
Gustafsen et al.

(10) Patent No.: US 10,688,119 B2
(45) Date of Patent: Jun. 23, 2020

(54) INHIBITORS OF PCSK9 FOR TREATMENT OF LIPOPROTEIN METABOLISM DISORDERS

(71) Applicant: Aarhus Universitet, Aarhus C (DK)

(72) Inventors: Camilla Gustafsen, Aarhus (DK); Peder Sondergaard Madsen, Risskov (DK); Simon Glerup Pedersen, Risskov (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 15/558,491

(22) PCT Filed: Mar. 18, 2016

(86) PCT No.: PCT/DK2016/050082
§ 371 (c)(1),
(2) Date: Sep. 14, 2017

(87) PCT Pub. No.: WO2016/150444
PCT Pub. Date: Sep. 29, 2016

(65) Prior Publication Data
US 2018/0193376 A1    Jul. 12, 2018

(30) Foreign Application Priority Data

Mar. 20, 2015 (DK) .................................. 201570158
Oct. 2, 2015 (DK) .................................. 201570623
Dec. 21, 2015 (DK) .................................. 201570839

(51) Int. Cl.
*C07K 16/40* (2006.01)
*A61K 39/395* (2006.01)
*A61K 31/737* (2006.01)
*A61K 31/727* (2006.01)
*C08B 37/00* (2006.01)
*A61K 31/185* (2006.01)
*A61K 39/00* (2006.01)

(52) U.S. Cl.
CPC .......... *A61K 31/737* (2013.01); *A61K 31/185* (2013.01); *A61K 31/727* (2013.01); *A61K 39/3955* (2013.01); *C07K 16/40* (2013.01); *C08B 37/0075* (2013.01); *A61K 2039/505* (2013.01); *C07K 2317/24* (2013.01); *C07K 2317/56* (2013.01); *C07K 2317/565* (2013.01); *C07K 2317/622* (2013.01); *C07K 2317/74* (2013.01); *C07K 2317/76* (2013.01); *Y02A 50/473* (2018.01)

(58) Field of Classification Search
None
See application file for complete search history.

(56) References Cited

U.S. PATENT DOCUMENTS

| 7,754,208 B2 | 7/2010 | Ledbetter et al. |
| 8,829,165 B2 | 9/2014 | Jackson et al. |
| 9,255,154 B2 | 2/2016 | Feldhaus et al. |
| 2003/0133939 A1 | 7/2003 | Ledbetter et al. |
| 2011/0033465 A1* | 2/2011 | Hedrick ................. C07K 16/40 424/136.1 |

FOREIGN PATENT DOCUMENTS

| EP | 0404097 | 12/1990 |
| EP | 0404097 A2 | 12/1990 |
| EP | 2495242 A2 | 9/2012 |
| WO | 9307167 A1 | 4/1993 |
| WO | 9311161 A1 | 6/1993 |
| WO | WO9311161 | 6/1993 |
| WO | 9409131 A1 | 4/1994 |
| WO | WO9409131 | 4/1994 |
| WO | 9413806 A1 | 6/1994 |
| WO | WO9413806 | 6/1994 |
| WO | 0243478 A2 | 6/2002 |
| WO | WO0243478 | 6/2002 |
| WO | 2009049370 A1 | 4/2009 |
| WO | 2010029513 A2 | 3/2010 |
| WO | WO2010029513 | 3/2010 |
| WO | 2010077854 A1 | 7/2010 |
| WO | 2012101253 A1 | 8/2012 |
| WO | 2012109530 A1 | 8/2012 |
| WO | 2013039958 A1 | 3/2013 |
| WO | 2013091103 A1 | 6/2013 |
| WO | WO2013091103 | 6/2013 |
| WO | 2013148284 A1 | 10/2013 |
| WO | WO2013148284 | 10/2013 |
| WO | 2013177536 A2 | 11/2013 |
| WO | WO2013177536 | 11/2013 |
| WO | 2014005224 A1 | 1/2014 |
| WO | 2014107739 A1 | 7/2014 |
| WO | 2014150983 A2 | 9/2014 |
| WO | WO 2014/150983 A2 | 9/2014 |

(Continued)

OTHER PUBLICATIONS

Paul, Fundamental Immunology, 3rd Edition, 1993, pp. 292-295.*
Casset et al; Biochemical and Biophysical Research Communications, 2003; 307:198-205.*
Sheridan, Phase 3 Data for PCSK9 Inhibitor Wows, (2013). Nat Biotechnol. Dec. 2013;31(12)-1057-8. doi- 10.1038_nbt1213-1057.
Benimetskaya et al., "Binding of phosphorothioate oligodeoxynucleotides to basic fibroblast growth factor, recombinant soluble CD4, laminin and fibronectin is P-chirality independent," Nucleic Acids Res, 1995, 23—4239-4245.

(Continued)

*Primary Examiner* — Bridget E Bunner
*Assistant Examiner* — Fozia Hamud
(74) *Attorney, Agent, or Firm* — Dinsmore & Shohl LLP; Weston R. Gould

(57) ABSTRACT

The present disclosure relates to inhibitors of proprotein convertase subtilisin-like/kexin type 9 (PCSK9) for the treatment of lipoprotein metabolism disorders.

10 Claims, 31 Drawing Sheets

Specification includes a Sequence Listing.

(56) References Cited

FOREIGN PATENT DOCUMENTS

WO         2016150444 A1     9/2016

OTHER PUBLICATIONS

Bird et al., "Single-Chain Antigen-Binding Proteins," (1988) Science 242:423-426.
Chan et al., "A proprtein convertase subtilisin/kexin type 9 neutralizing antibody reduces serum cholesterol in mice and nonhuman primates," (2009) Proc Natl Acad Sci USA. Jun. 16, 2009;106(24)9820-5. doi- 10-1073-pnas-0903849106.
Cunningham et al., "Structural and biophysical studies of PCSK9 and its mutants linked to familial hypercholesterolemia," (2007) Nat Struct Mol Biol 1485)—p. 413-9.
Fisher et al., "Effects of pH and Low Density Lipoprotein (LDL) on PCSK9-dependent LDL Recetor Regulation," J. Biol. Chem.-2007-20502-12.
Greenberg et al, "A new antigen receptor gene family that undergoes rearrangement and extensive somatic diversification in sharks," (1995) Nature. 374, 168-173.
Guns et al., "P2Y receptors and atherosclerosis in apolipoprotein E-deficient mice," 2009. British Journal of Pharmacology (2010), 159, 326-336.
Gustafsen et al., "The hypercholesterolemia-risk gene SORT1 facilitates PCSK9 Secretion," 2014 Cell Met.vol. 19, Issue 2, p. 310-318.
Hamers-Casterman et al. "Naturally occurring antibodies devoid of light chains," (1993) Nature. 363(6428)-446-8.
Herbert et al. Biochemical and Pharmacological Properties of SANORG 32701, Circ Res 79, 590-600 (1996).
Holliger et al."Diabodies: Small bivalent and bispecific antibody fragments," (1993) Proc. Natl. Acad Sci. USA 90—6444-6448.
Huston et al."Protein engineering of antibody binding sites: recovery of specific activity in an antidigoxin single-chain Fv analogue produced in *Escherichia coli*," (1988) Proc. Natl. Acad. Sci. USA 85-5879-5883.
Jerabek-Willemsen et al, "Molecular Interaction Studies Using Microscale Thermophoresis," Assay Drug Dev technol 9(4)—p. 342-53, Nov. 2011.
Kohler and Milstein, "Continuous cultures of fussed cells secreting antibody of predefined specificity," (1975) Nature 256-495.
Lagace et al., "Secreted PCSK9 decreases the number of LDL receptors in hepatocytes and in livers of parabiotic mice," (2006) J Clin Invest. Nov. 2006;116(11)-2995-3005.
Lakoski et al., Genetic and Metabolic Determinants of Plasma PCSK9 Levels, (2009) J Clin Endocrinol metab 94(7) p. 2537-43.
Lonberg, N. et al., Antigen-specific human antibodies from mice comprising four distinct genetic modifications, (1994) Nature 368 (6474)-856-859.
Mullard, Asher, PCSK9 Inhibitors are go, (2015) Nat Rev Drug Discov, 14, 593.
Munck Petersen et al, Propeptide cleavage conditions sortilin/neurotensin receptor-3 for ligand binding, (1999) EMBO J 18(3)-595-604.
Nour-Eldin et al, Advancing uracil-excision based cloning towards an ideal technique for cloning PCR fragments, (2006) Nucleic Acids Res. 34(18)-e122.
Piper et al., The Crystal Structure of PCSK9: A Regulator of Plasma LDL-Cholesterol, (2007) Structure 15(5)—p. 545-52.
Reiter et al., Improved Binding and Antitumor Activity of a Recombinant Anti-erbB2 Immunotoxin by Disulfide Stabilization of the Fv Fragment, (1994) J. Biol. Chem. 269(15)-18327-31.
Seidah, Nabil G. et al; "PCSK9 a Key Modulator of Cardiovascular Health"; Circulation Reaearch; vol. 114, No. 6; Mar. 14, 2014; pp. 1022-1036; XP055221336.
Sheridan, "New Class PCSK9 blockers stride into cholesterol market," C. Nat. Biotechnol. 33, 8, 785-786 (2015).
Soderberg et al., Direct Observation of individual endogenous protein complexes in situ by proximity ligation, Nat Methods 3, 995-1000 (2006).
Stein, C.A., Does antisense exist? (1995) Nat Med 1—1119-1121.
Yabukov et al. (1993) J Biol Chem. 268(25)-18818-23.
Villiers et al, User friendly DNA recombination (USERec): a simple and flexible near homology-independent method ofr gene library construction, (2010) Protein Eng Des Sel. 23(1)-1-8.
Ward et al, Binding activities of a repertoire of single immunoglobulin variable domains secreted from *Escherichia coli*, (1989) Nature 341-544-546.
Wozniak Knopp et al, Stabilisation of the Fc Fragment of Human IgG1 by Engineered Intradomain Disulfide Bonds, (2012) PLoS One 7(1)—e30083.
Xu and Esko, Demystifying Haparan Sulfate-Protein Interactions, (2014) Annu Rev Biochem. 2014;83-129-57.
Yakubov et al, Oligodeoxynucleotides Interact with Recombinant CD4 at Multiple Sites, J Blol Chem (1993) 268 (25); 18818-23.
Tyrrell D J., et al.: "Therapeutic uses of heparin beyond its traditional role as an anticoagulant," Trends in Pharmacological Sciences, Elsevier, Haywarth, GB, vol. 16, No. 6, Jun. 1, 1995, pp. 198-204, XP004207497, ISSN: 0165-6147, DOI: 10.1016/S0165-6147 (00) 89022-7 p. 200-p. 201.
Hecht, et al; Journal of Clinical Oncology; vol. 27; No. 5; Feb. 10, 2009; pp. 672-680.
Benimetskaya et al.; Nucleic Acids Research, 1995, vol. 23, No. 21; pp. 4239-4245.
Biessen, et al; Biochemical Journal; vol. 302, No. 1, Aug. 15, 1994; pp. 283-289.
Bird, et al; Science, vol. 242, No. 4877 (Oct. 21, 1988), pp. 423-426.
Casset, et al; Biochemical and Biophysical Research Communications; vol. 307, 2003, pp. 198-205.
Chan, et al; Proc. Natl. Acad. Sci. USA; vol. 106, No. 24; Jun. 16, 2009; pp. 9820-9825.
Cunningham, et al.; Nature Structural & Molecular Biology; vol. 14 No. 5; May 2007.
de la Paz, et al.; Pharmacologyonline 3: pp. 462-466 (2006).
Fisher, et al; Journal of Biological Chemistry; vol. 282; No. 28; Jul. 13, 2007.
Greenberg, et al; Nature; vol. 374; Mar. 9, 1995.
Guns, el al; British Journal of Pharmacology (2010): vol. 159: pp. 326-336.
Gustafsen, el al; Cell Metabolism 19, 310-318, Feb. 4, 2014.
Gustafsen, el al: Nature Communications; vol. 8. No. 1, Sep. 11, 2017.
Hamers-Casterman, et al; Letters to Nature; vol. 363; Jun. 3, 1993.
Herbert, et al; Circ Res 79: pp. 590-600 (1996).
Hollinger, et al.; Proc. Natl Acad. Sci. USA, vol. 90, pp. 6444-6448; Jul. 1993.
Horlacher. T. el al.; Biochemistry, Apr. 5, 2011, vol. 50, pp. 2650-2659.
Huston, et al: Proc. Natl. Acad. Sci. USA, vol. 85, pp. 5879-5883, Aug. 1988; Biochemistry.
Jerabek-Willemsen, el al.; Assay and Drug Development Technologies. vol. 9, No. 4; Aug. 2011.
Kohler and Milstein; Nature, vol. 256, Aug. 7, 1975; pp. 495-497.
Lagace, et al.; The Journal of Clinical Investigation: vol. 116; No. 11, Nov. 2001.
Lakoski, et al.; J Clin Endocrinol Metab., 2009; vol. 94(7): pp. 2537-2543.
Lonberg, et al.; Nature, vol. 368; Apr. 28, 1994.
Mullard; Nature Reviews: Drug Discovery; vol. 14, (Sep. 2015) 593.
Munck Petersen ,et al.; The EMBO Journal: vol. 18, No. 3; pp. 595-604, 1999.
Nonaka, et al; Proc. Natl. Acad. Sci. USA; Jun. 3, 2014; vol. 111, No. 22; pp. 8173-8178.
Nour-Eldin, et al.; Nucleic Acids Research, 2006, vol. 34, No. 18.
Paul, William E., Fundamental Immunology, pp. 292-295 (William Paul Ed., Raven Press 1993).
Piper, et al; Structure: vol. 15, pp. 545-552, May 2007.
Reiter, et al; The Journal of Biological Chemistry; vol. 269, No. 28, Issue of Jul. 1994 15, pp. 18327-18331, 1994.
Seidah, et al; Review; Circ Res. 2014; vol. 114; 1022-1036.
Sheridan, C.; Nature Biotechnology; vol. 33, No. 8 Aug. 2015.

(56) References Cited

OTHER PUBLICATIONS

Stein, C.A.; Nature Medicine, vol. 1; No. 11, Nov. 1995; pp. 1119-1121.
Soderberg, et al; Nature Methods; vol. 3; No. 12; Dec. 2006; pp. 995-10006.
Villiers, Br. et al; Protein Engineering, Design & Selection; vol. 23 No. 1 pp. 1-8, 2010.
Walley, et al; Curr Opin Cril Care, 2016, 22:464-469; vol. 22, No. 5; Oct. 2016.
Ward et al; (1989) Nature; vol. 341; pp. 544-546.
Wozniak-Knopp, et al; PLoS One; Jan. 2012 ; vol. 7. Issue 1; e30083.
Xu and Esko; (2014) Annu Rev Biochem.; 2014; vol. 83; pp. 129-157.
Yabukov et al. (1993) J Biol Chem.; vol. 268, No. 25; pp. 18818-18823.
Tyrrell DJ., et al.; Trends in Pharmacological Sciences, Elsevier, Haywarth, GB, vol. 16, No. 6, Jun. 1, 1995, pp. 198-204.
Lima et al., Structural and thermodynamic analysis of thrombin:suramin interaction in solution and crystal phases, Biochim Biophys Acta. Jun. 2009 ;1794(6)-873-81.
McCoy, A.J., et al., Structure of beta-antithrombin and the effect of glycosylation on antithrombin's heparin affinity and activity. J Mol Biol, 2003. 326(3)—p. 823-33.

\* cited by examiner

C

D

E

C

D

D

*** pAb control

I

J

Mouse liver LDLR 1 hour post injection

SEQUENCE LISTING

```
<160> NUMBER OF SEQ ID NOS: 27

<210> SEQ ID NO 1
<211> LENGTH: 692
<212> TYPE: PRT
<213> ORGANISM: Homo sapiens
<220> FEATURE:
<221> NAME/KEY: BINDING
<222> LOCATION: (78)..(167)
<223> OTHER INFORMATION: HSPG binding site
<220> FEATURE:
<221> NAME/KEY: MISC_FEATURE
<222> LOCATION: (93)..(93)
<223> OTHER INFORMATION: R93
<220> FEATURE:
<221> NAME/KEY: MISC_FEATURE
<222> LOCATION: (96)..(96)
<223> OTHER INFORMATION: R96
<220> FEATURE:
<221> NAME/KEY: MISC_FEATURE
<222> LOCATION: (97)..(97)
<223> OTHER INFORMATION: R97
<220> FEATURE:
<221> NAME/KEY: MISC_FEATURE
<222> LOCATION: (104)..(104)
<223> OTHER INFORMATION: R104
<220> FEATURE:
<221> NAME/KEY: MISC_FEATURE
<222> LOCATION: (105)..(105)
<223> OTHER INFORMATION: R105
<220> FEATURE:
<221> NAME/KEY: MISC_FEATURE
<222> LOCATION: (136)..(136)
<223> OTHER INFORMATION: K136
<220> FEATURE:
<221> NAME/KEY: MISC_FEATURE
<222> LOCATION: (139)..(139)
<223> OTHER INFORMATION: H139
<220> FEATURE:
<221> NAME/KEY: MISC_FEATURE
<222> LOCATION: (165)..(165)
<223> OTHER INFORMATION: R165
<220> FEATURE:
```

```
<221> NAME/KEY: MISC_FEATURE
<222> LOCATION: (167)..(167)
<223> OTHER INFORMATION: R167

<400> SEQUENCE: 1
```

| | | | | | | | | | | | | | | |
|---|---|---|---|---|---|---|---|---|---|---|---|---|---|---|
| Met | Gly | Thr | Val | Ser | Ser | Arg | Arg | Ser | Trp | Trp | Pro | Leu | Pro | Leu | Leu |
| 1 | | | | 5 | | | | | 10 | | | | | 15 | |

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu

```
                                385                 390                 395                 400
        Ser Ala Glu Pro Glu Leu Thr Leu Ala Glu Leu Arg Gln Arg Leu Ile
                        405                 410                 415

His Phe Ser Ala Lys Asp Val Ile Asn Glu Ala Trp Phe Pro Glu Asp
                        420                 425                 430

Gln Arg Val Leu Thr Pro Asn Leu Val Ala Ala Leu Pro Pro Ser Thr
                        435                 440                 445

His Gly Ala Gly Trp Gln Leu Phe Cys Arg Thr Val Trp Ser Ala His
                450                 455                 460

Ser Gly Pro Thr Arg Met Ala Thr Ala Val Ala Arg Cys Ala Pro Asp
        465                 470                 475                 480

Glu Glu Leu Leu Ser Cys Ser Phe Ser Arg Ser Gly Lys Arg Arg
                        485                 490                 495

Gly Glu Arg Met Glu Ala Gln Gly Gly Lys Leu Val Cys Arg Ala His
                        500                 505                 510

Asn Ala Phe Gly Gly Glu Gly Val Tyr Ala Ile Ala Arg Cys Cys Leu
                        515                 520                 525

Leu Pro Gln Ala Asn Cys Ser Val His Thr Ala Pro Pro Ala Glu Ala
                530                 535                 540

Ser Met Gly Thr Arg Val His Cys His Gln Gln Gly His Val Leu Thr
        545                 550                 555                 560

Gly Cys Ser Ser His Trp Glu Val Glu Asp Leu Gly Thr His Lys Pro
                        565                 570                 575

Pro Val Leu Arg Pro Arg Gly Gln Pro Asn Gln Cys Val Gly His Arg
                        580                 585                 590

Glu Ala Ser Ile His Ala Ser Cys Cys His Ala Pro Gly Leu Glu Cys
                        595                 600                 605

Lys Val Lys Glu His Gly Ile Pro Ala Pro Gln Glu Gln Val Thr Val
                        610                 615                 620

Ala Cys Glu Glu Gly Trp Thr Leu Thr Gly Cys Ser Ala Leu Pro Gly
        625                 630                 635                 640

Thr Ser His Val Leu Gly Ala Tyr Ala Val Asp Asn Thr Cys Val Val
                        645                 650                 655

Arg Ser Arg Asp Val Ser Thr Thr Gly Ser Thr Ser Glu Gly Ala Val
                        660                 665                 670

Thr Ala Val Ala Ile Cys Cys Arg Ser Arg His Leu Ala Gln Ala Ser
                        675                 680                 685

Gln Glu Leu Gln
                690

<210> SEQ ID NO 2
<211> LENGTH: 318
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(318)
<223> OTHER INFORMATION: BNT-8H4-B8/C7-E11_VK
<220> FEATURE:
<221> NAME/KEY: V_region
<222> LOCATION: (1)..(69)
<220> FEATURE:
<221> NAME/KEY: V_segment
<222> LOCATION: (70)..(102)
<223> OTHER INFORMATION: CDR1
```

```
<220> FEATURE:
<221> NAME/KEY: V_region
<222> LOCATION: (103)..(147)
<220> FEATURE:
<221> NAME/KEY: V_segment
<222> LOCATION: (148)..(168)
<223> OTHER INFORMATION: CDR2
<220> FEATURE:
<221> NAME/KEY: V_region
<222> LOCATION: (169)..(264)
<220> FEATURE:
<221> NAME/KEY: V_segment
<222> LOCATION: (265)..(288)
<223> OTHER INFORMATION: CDR3
<220> FEATURE:
<221> NAME/KEY: J_segment
<222> LOCATION: (289)..(318)

<400> SEQUENCE: 2 gat att gtg atg acc cag tct ccc tca ctc ctg tct gca tct gtg gga       48
Asp Ile Val Met Thr Gln Ser Pro Ser Leu Leu Ser Ala Ser Val Gly
1               5                   10                  15 gac aga gtc act ctt agc tgc aaa gga agt cag aat att aac aat tac       96
Asp Arg Val Thr Leu Ser Cys Lys Gly Ser Gln Asn Ile Asn Asn Tyr
            20                  25                  30 tta gcc tgg tac caa caa aag ctc gga gaa gct ccc aaa ctc ctg atc      144
Leu Ala Trp Tyr Gln Gln Lys Leu Gly Glu Ala Pro Lys Leu Leu Ile
        35                  40                  45 tat aat aca aac agt tta caa acg ggc atc cca tca agg ttc agt ggc      192
Tyr Asn Thr Asn Ser Leu Gln Thr Gly Ile Pro Ser Arg Phe Ser Gly
    50                  55                  60 agt gga tct ggt aca gat tgc aca ctc acc atc aga agc ctg cag cct      240
Ser Gly Ser Gly Thr Asp Cys Thr Leu Thr Ile Arg Ser Leu Gln Pro
65                  70                  75                  80 gaa gat gtt gcc aca tat ttc tgc tat cag tat aac aac ggg aac acg      288
Glu Asp Val Ala Thr Tyr Phe Cys Tyr Gln Tyr Asn Asn Gly Asn Thr
                85                  90                  95 ttt gga ggt ggg acc aag ctg gag ctg aaa                              318
Phe Gly Gly Gly Thr Lys Leu Glu Leu Lys
            100                 105

<210> SEQ ID NO 3
<211> LENGTH: 106
<212> TYPE: PRT
<213> ORGANISM: Artificial sequence
<220> FEATURE:
<223> OTHER INFORMATION: Synthetic Construct

<400> SEQUENCE: 3

Asp Ile Val Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Asn Thr Asn Ser Leu Gln Thr Gly Ile Pro Ser Arg Phe Ser Gly
    50                  55                  60

Ser Gly Ser Gly Thr Asp Cys Thr Leu Thr Ile Arg Ser Leu Gln Pro
65                  70                  75                  80

Glu Asp Val Ala Thr Tyr Phe Cys Tyr Gln Tyr Asn Asn Gly Asn Thr
                85                  90                  95

Phe Gly Gly Gly Thr Lys Leu Glu Leu Lys
            100                 105
```

<210> SEQ ID NO 4
<211> LENGTH: 336
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(336)
<223> OTHER INFORMATION: BNT-5E11-D4/G1-E4_VK
<220> FEATURE:
<221> NAME/KEY: V_region
<222> LOCATION: (1)..(69)
<223> OTHER INFORMATION: FWR1
<220> FEATURE:
<221> NAME/KEY: V_segment
<222> LOCATION: (70)..(117)
<223> OTHER INFORMATION: CDR1
<220> FEATURE:
<221> NAME/KEY: V_region
<222> LOCATION: (118)..(162)
<223> OTHER INFORMATION: FWR2
<220> FEATURE:
<221> NAME/KEY: V_segment
<222> LOCATION: (163)..(183)
<223> OTHER INFORMATION: CDR2
<220> FEATURE:
<221> NAME/KEY: V_region
<222> LOCATION: (184)..(279)
<223> OTHER INFORMATION: FWR3
<220> FEATURE:
<221> NAME/KEY: V_segment
<222> LOCATION: (280)..(306)
<223> OTHER INFORMATION: CDR3
<220> FEATURE:
<221> NAME/KEY: J_segment
<222> LOCATION: (307)..(336)
<223> OTHER INFORMATION: JK

<400> SEQUENCE: 4

```
gat gtt gtg ttg aca caa act cca gtt ttc ctg tct gtc aca ctt gga      48
Asp Val Val Leu Thr Gln Thr Pro Val Phe Leu Ser Val Thr Leu Gly
1               5                   10                  15 gat cag act tct ata tct tgt agg tct agt cag agt ctg gaa tat agt      96
Asp Gln Thr Ser Ile Ser Cys Arg Ser Ser Gln Ser Leu Glu Tyr Ser
            20                  25                  30 gat gga tac act tat ttg gaa tgg tac cta cag aaa ccg ggc cag tct     144
Asp Gly Tyr Thr Tyr Leu Glu Trp Tyr Leu Gln Lys Pro Gly Gln Ser
        35                  40                  45 cca cag ctc ctc atc tat gaa gtt tcc aac cga ttt tct ggg gtc cca     192
Pro Gln Leu Leu Ile Tyr Glu Val Ser Asn Arg Phe Ser Gly Val Pro
    50                  55                  60 gac agg ttc att ggc agt ggg tca ggg aca gat ttc acc ctc aag atc     240
Asp Arg Phe Ile Gly Ser Gly Ser Gly Thr Asp Phe Thr Leu Lys Ile
65                  70                  75                  80 agc aga gta gag cct gag gac ttg gga gtt tat tac tgc ttc caa ggt     288
Ser Arg Val Glu Pro Glu Asp Leu Gly Val Tyr Tyr Cys Phe Gln Gly
                85                  90                  95 aca cat gat cct ctc acg ttc ggt tct ggg acc aag ctg gag atc aaa     336
Thr His Asp Pro Leu Thr Phe Gly Ser Gly Thr Lys Leu Glu Ile Lys
            100                 105                 110
```

<210> SEQ ID NO 5
<211> LENGTH: 112
<212> TYPE: PRT
<213> ORGANISM: Artificial sequence
<220> FEATURE:
<223> OTHER INFORMATION: Synthetic Construct

<400> SEQUENCE: 5

| Asp | Val | Val | Leu | Thr | Gln | Thr | Pro | Val | Phe | Leu | Ser | Val | Thr | Leu | Gly |
|---|---|---|---|---|---|---|---|---|---|---|---|---|---|---|---|
| 1 | | | | 5 | | | | | 10 | | | | | 15 | |

| Asp | Gln | Thr | Ser | Ile | Ser | Cys | Arg | Ser | Ser | Gln | Ser | Leu | Glu | Tyr | Ser |
|---|---|---|---|---|---|---|---|---|---|---|---|---|---|---|---|
| | | | 20 | | | | | 25 | | | | | 30 | | |

| Asp | Gly | Tyr | Thr | Tyr | Leu | Glu | Trp | Tyr | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Gln | Leu | Leu | Ile | Tyr | Glu | Val | Ser | Asn | Arg | Phe | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Ile | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Pro | Glu | Asp | Leu | Gly | Val | Tyr | Tyr | Cys | Phe | Gln | Gly |
|---|---|---|---|---|---|---|---|---|---|---|---|---|---|---|---|
| | | | | 85 | | | | | 90 | | | | | 95 | |

| Thr | His | Asp | Pro | Leu | Thr | Phe | Gly | Ser | Gly | Thr | Lys | Leu | Glu | Ile | Lys |
|---|---|---|---|---|---|---|---|---|---|---|---|---|---|---|---|
| | | | 100 | | | | | 105 | | | | | 110 | | |

<210> SEQ ID NO 6
<211> LENGTH: 336
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(336)
<223> OTHER INFORMATION: BNT-5E11-D4/G1-E4_VH
<220> FEATURE:
<221> NAME/KEY: V_region
<222> LOCATION: (1)..(90)
<223> OTHER INFORMATION: FWR1
<220> FEATURE:
<221> NAME/KEY: V_segment
<222> LOCATION: (91)..(108)
<223> OTHER INFORMATION: CDR1
<220> FEATURE:
<221> NAME/KEY: V_region
<222> LOCATION: (109)..(150)
<223> OTHER INFORMATION: FWR2
<220> FEATURE:
<221> NAME/KEY: V_segment
<222> LOCATION: (151)..(198)
<223> OTHER INFORMATION: CDR2
<220> FEATURE:
<221> NAME/KEY: V_region
<222> LOCATION: (199)..(294)
<223> OTHER INFORMATION: FWR3
<220> FEATURE:
<221> NAME/KEY: V_segment
<222> LOCATION: (295)..(303)
<223> OTHER INFORMATION: CDR3
<220> FEATURE:
<221> NAME/KEY: J_segment
<222> LOCATION: (304)..(336)
<223> OTHER INFORMATION: JH

<400> SEQUENCE: 6

| gag | gtg | cag | ctg | cag | gag | tca | gga | cct | ggc | ctt | gtg | aaa | cct | tca | cag | 48 |
|---|---|---|---|---|---|---|---|---|---|---|---|---|---|---|---|---|
| Glu | Val | Gln | Leu | Gln | Glu | Ser | Gly | Pro | Gly | Leu | Val | Lys | Pro | Ser | Gln | |
| 1 | | | | 5 | | | | | 10 | | | | | 15 | | |

| tca | ctc | tcc | ctc | acc | tgt | tct | gtc | act | ggt | tac | acc | att | acc | agt | ggt | 96 |
|---|---|---|---|---|---|---|---|---|---|---|---|---|---|---|---|---|
| Ser | Leu | Ser | Leu | Thr | Cys | Ser | Val | Thr | Gly | Tyr | Thr | Ile | Thr | Ser | Gly | |
| | | | 20 | | | | | 25 | | | | | 30 | | | |

| tat | gat | tgg | agc | tgg | atc | cgg | agg | ttc | cca | gga | aat | aca | atg | gag | tgg | 144 |
|---|---|---|---|---|---|---|---|---|---|---|---|---|---|---|---|---|
| Tyr | Asp | Trp | Ser | Trp | Ile | Arg | Arg | Phe | Pro | Gly | Asn | Thr | Met | Glu | Trp | |
| | | 35 | | | | | 40 | | | | | 45 | | | | |

```
atg gga gac ata agt tac agt ggt agc act aac tac aac cca tcg ctc      192
Met Gly Asp Ile Ser Tyr Ser Gly Ser Thr Asn Tyr Asn Pro Ser Leu
    50              55                  60 aaa agt cga gtc tcc att aca aga gac aca tcc aag aat cag ttc ttc      240
Lys Ser Arg Val Ser Ile Thr Arg Asp Thr Ser Lys Asn Gln Phe Phe
65              70                  75                  80 ctg cag ttg aac tct gta act act ggg gat aca gcc aca tat tac tgt      288
Leu Gln Leu Asn Ser Val Thr Thr Gly Asp Thr Ala Thr Tyr Tyr Cys
                85                  90                  95 gca aaa cta ccc ggc tgg ggc caa ggc act ctg gtc act gtc tct tca      336
Ala Lys Leu Pro Gly Trp Gly Gln Gly Thr Leu Val Thr Val Ser Ser
            100                 105                 110
```

<210> SEQ ID NO 7
<211> LENGTH: 112
<212> TYPE: PRT
<213> ORGANISM: Artificial sequence
<220> FEATURE:
<223> OTHER INFORMATION: Synthetic Construct

<400> SEQUENCE: 7

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Ser Trp Ile Arg Arg Phe Pro Gly Asn Thr Met Glu Trp
        35                  40                  45

Met Gly Asp Ile Ser Tyr Ser Gly Ser Thr Asn Tyr Asn Pro Ser Leu
    50              55                  60

Lys Ser Arg Val Ser Ile Thr Arg Asp Thr Ser Lys Asn Gln Phe Phe
65              70                  75                  80

Leu Gln Leu Asn Ser Val Thr Thr Gly Asp Thr Ala Thr Tyr Tyr Cys
                85                  90                  95

Ala Lys Leu Pro Gly Trp Gly Gln Gly Thr Leu Val Thr Val Ser Ser
            100                 105                 110
```

<210> SEQ ID NO 8
<211> LENGTH: 354
<212> TYPE: DNA
<213> ORGANISM: Artificial sequence
<220> FEATURE:
<223> OTHER INFORMATION: Sequences obtained by sequencing of the
      variable regions of the immunoglobulin genes expressed by rat
      hybridomas BNT-8H4-B8/C7-E11, BNT-5E11-D4/G1-E4
<220> FEATURE:
<221> NAME/KEY: CDS
<222> LOCATION: (1)..(354)
<223> OTHER INFORMATION: BNT-8H4-B8/C7-E11_VH
<220> FEATURE:
<221> NAME/KEY: V_region
<222> LOCATION: (1)..(90)
<223> OTHER INFORMATION: FWR1
<220> FEATURE:
<221> NAME/KEY: V_segment
<222> LOCATION: (91)..(111)
<223> OTHER INFORMATION: CDR1
<220> FEATURE:
<221> NAME/KEY: V_region
<222> LOCATION: (112)..(153)
<223> OTHER INFORMATION: FWR2
<220> FEATURE:
<221> NAME/KEY: V_segment
<222> LOCATION: (154)..(201)
<223> OTHER INFORMATION: CDR2
<220> FEATURE:
<221> NAME/KEY: V_region

```
<222> LOCATION: (202)..(297)
<223> OTHER INFORMATION: FWR3
<220> FEATURE:
<221> NAME/KEY: V_segment
<222> LOCATION: (298)..(321)
<223> OTHER INFORMATION: CDR3
<220> FEATURE:
<221> NAME/KEY: J_segment
<222> LOCATION: (322)..(354)
<223> OTHER INFORMATION: JH

<400> SEQUENCE: 8 cag gtt act ctg aaa gag tct ggc cct ggg ata ttg cag cct tcc cag       48
Gln Val Thr Leu Lys Glu Ser Gly Pro Gly Ile Leu Gln Pro Ser Gln
1               5                   10                  15 acc ctc agt ctg act tgc tct ttc tct ggg ttt tca ctg agc agt tca       96
Thr Leu Ser Leu Thr Cys Ser Phe Ser Gly Phe Ser Leu Ser Ser Ser
            20                  25                  30 ggt ata tgt gtg agc tgg att cgt cag cct tca ggg aag ggt ctg gag      144
Gly Ile Cys Val Ser Trp Ile Arg Gln Pro Ser Gly Lys Gly Leu Glu
        35                  40                  45 tgg ctg gca act att tgt tgg gag gat agt aag ggc tac aac cct tct      192
Trp Leu Ala Thr Ile Cys Trp Glu Asp Ser Lys Gly Tyr Asn Pro Ser
50                  55                  60 ctg aag aac cgg ctc acg atc tcc aag gac acc tcc aac aac caa gca      240
Leu Lys Asn Arg Leu Thr Ile Ser Lys Asp Thr Ser Asn Asn Gln Ala
65                  70                  75                  80 ctc ctc agg atc acc agt gtg gac act gca gat acc gcc att tac tac      288
Leu Leu Arg Ile Thr Ser Val Asp Thr Ala Asp Thr Ala Ile Tyr Tyr
                85                  90                  95 tgt gct cgg gtt tat tac tgg tac ttt gac ttc tgg ggc cca gga acc      336
Cys Ala Arg Val Tyr Tyr Trp Tyr Phe Asp Phe Trp Gly Pro Gly Thr
            100                 105                 110 atg gtc acc gtg tcc tca                                              354
Met Val Thr Val Ser Ser
        115

<210> SEQ ID NO 9
<211> LENGTH: 118
<212> TYPE: PRT
<213> ORGANISM: Artificial sequence
<220> FEATURE:
<223> OTHER INFORMATION: Synthetic Construct

<400> SEQUENCE: 9

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Ser Ser
            20                  25                  30

Gly Ile Cys Val Ser Trp Ile Arg Gln Pro Ser Gly Lys Gly Leu Glu
        35                  40                  45

Trp Leu Ala Thr Ile Cys Trp Glu Asp Ser Lys Gly Tyr Asn Pro Ser
50                  55                  60

Leu Lys Asn Arg Leu Thr Ile Ser Lys Asp Thr Ser Asn Asn Gln Ala
65                  70                  75                  80

Leu Leu Arg Ile Thr Ser Val Asp Thr Ala Asp Thr Ala Ile Tyr Tyr
                85                  90                  95

Cys Ala Arg Val Tyr Tyr Trp Tyr Phe Asp Phe Trp Gly Pro Gly Thr
            100                 105                 110

Met Val Thr Val Ser Ser
        115
```

```
<210> SEQ ID NO 10
<211> LENGTH: 6
<212> TYPE: PRT
<213> ORGANISM: Artificial sequence
<220> FEATURE:
<223> OTHER INFORMATION: CDR1 of SEQ ID NO: 7

<400> SEQUENCE: 10

Ser Gly Tyr Asp Trp Ser
1               5

<210> SEQ ID NO 11
<211> LENGTH: 16
<212> TYPE: PRT
<213> ORGANISM: Artificial sequence
<220> FEATURE:
<223> OTHER INFORMATION: CDR2 of SEQ ID NO: 7

<400> SEQUENCE: 11

Asp Ile Ser Tyr Ser Gly Ser Thr Asn Tyr Asn Pro Ser Leu Lys Ser
1               5                   10                  15

<210> SEQ ID NO 12
<211> LENGTH: 3
<212> TYPE: PRT
<213> ORGANISM: Artificial sequence
<220> FEATURE:
<223> OTHER INFORMATION: CDR3 of SEQ ID NO: 7

<400> SEQUENCE: 12

Leu Pro Gly
1

<210> SEQ ID NO 13
<211> LENGTH: 16
<212> TYPE: PRT
<213> ORGANISM: Artificial sequence
<220> FEATURE:
<223> OTHER INFORMATION: CDR1 of SEQ ID NO: 5

<400> SEQUENCE: 13

Arg Ser Ser Gln Ser Leu Glu Tyr Ser Asp Gly Tyr Thr Tyr Leu Glu
1               5                   10                  15

<210> SEQ ID NO 14
<211> LENGTH: 7
<212> TYPE: PRT
<213> ORGANISM: Artificial sequence
<220> FEATURE:
<223> OTHER INFORMATION: CDR2 of SEQ ID NO: 5

<400> SEQUENCE: 14

Glu Val Ser Asn Arg Phe Ser
1               5

<210> SEQ ID NO 15
<211> LENGTH: 9
<212> TYPE: PRT
<213> ORGANISM: Artificial sequence
<220> FEATURE:
<223> OTHER INFORMATION: CDR3 of SEQ ID NO: 5

<400> SEQUENCE: 15

Phe Gln Gly Thr His Asp Pro Leu Thr
1               5
```

```
<210> SEQ ID NO 16
<211> LENGTH: 7
<212> TYPE: PRT
<213> ORGANISM: Artificial sequence
<220> FEATURE:
<223> OTHER INFORMATION: CDR1 of SEQ ID NO: 9

<400> SEQUENCE: 16

Ser Ser Gly Ile Cys Val Ser
1               5

<210> SEQ ID NO 17
<211> LENGTH: 16
<212> TYPE: PRT
<213> ORGANISM: Artificial sequence
<220> FEATURE:
<223> OTHER INFORMATION: CDR2 of SEQ ID NO: 9

<400> SEQUENCE: 17

Thr Ile Cys Trp Glu Asp Ser Lys Gly Tyr Asn Pro Ser Leu Lys Asn
1               5                   10                  15

<210> SEQ ID NO 18
<211> LENGTH: 8
<212> TYPE: PRT
<213> ORGANISM: Artificial sequence
<220> FEATURE:
<223> OTHER INFORMATION: CDR3 of SEQ ID NO: 9

<400> SEQUENCE: 18

Val Tyr Tyr Trp Tyr Phe Asp Phe
1               5

<210> SEQ ID NO 19
<211> LENGTH: 11
<212> TYPE: PRT
<213> ORGANISM: Artificial sequence
<220> FEATURE:
<223> OTHER INFORMATION: CDR1 of SEQ ID NO: 3

<400> SEQUENCE: 19

Lys Gly Ser Gln Asn Ile Asn Asn Tyr Leu Ala
1               5                   10

<210> SEQ ID NO 20
<211> LENGTH: 7
<212> TYPE: PRT
<213> ORGANISM: Artificial sequence
<220> FEATURE:
<223> OTHER INFORMATION: CDR2 of SEQ ID NO: 3

<400> SEQUENCE: 20

Asn Thr Asn Ser Leu Gln Thr
1               5

<210> SEQ ID NO 21
<211> LENGTH: 8
<212> TYPE: PRT
<213> ORGANISM: Artificial sequence
<220> FEATURE:
<223> OTHER INFORMATION: CDR3 of SEQ ID NO: 3

<400> SEQUENCE: 21

Tyr Gln Tyr Asn Asn Gly Asn Thr
1               5

<210> SEQ ID NO 22
```

```
<211> LENGTH: 21
<212> TYPE: DNA
<213> ORGANISM: Artificial Sequence
<220> FEATURE:
<223> OTHER INFORMATION: LDLR forward primer

<400> SEQUENCE: 22
acggcgtctc ttcctatgac a                                              21

<210> SEQ ID NO 23
<211> LENGTH: 20
<212> TYPE: DNA
<213> ORGANISM: Artificial sequence
<220> FEATURE:
<223> OTHER INFORMATION: LDLR reverse primer

<400> SEQUENCE: 23
cccttggtat ccgcaacaga                                                20

<210> SEQ ID NO 24
<211> LENGTH: 19
<212> TYPE: DNA
<213> ORGANISM: Artificial sequence
<220> FEATURE:
<223> OTHER INFORMATION: PCSK9 forward primer

<400> SEQUENCE: 24
cctggagcgg attacccct                                                 19

<210> SEQ ID NO 25
<211> LENGTH: 22
<212> TYPE: DNA
<213> ORGANISM: Artificial sequence
<220> FEATURE:
<223> OTHER INFORMATION: PCSK9 reverse primer

<400> SEQUENCE: 25
ctgtatgctg gtgtctagga ga                                             22

<210> SEQ ID NO 26
<211> LENGTH: 22
<212> TYPE: DNA
<213> ORGANISM: Artificial sequence
<220> FEATURE:
<223> OTHER INFORMATION: GAPDH forwrad primer

<400> SEQUENCE: 26
acaactttgg tatcgtggaa gg                                             22

<210> SEQ ID NO 27
<211> LENGTH: 19
<212> TYPE: DNA
<213> ORGANISM: Artificial sequence
<220> FEATURE:
<223> OTHER INFORMATION: GAPDH reverse primer

<400> SEQUENCE: 27
gccatcacgc cacagtttc                                                 19
```

INHIBITORS OF PCSK9 FOR TREATMENT OF LIPOPROTEIN METABOLISM DISORDERS

TECHNICAL FIELD

The present disclosure relates to inhibitors of proprotein convertase subtilisin-like/kexin type 9 (PCSK9) for the treatment of lipoprotein metabolism disorders.

BACKGROUND

Coronary artery disease caused by atherosclerosis is the leading cause of death in Europe and the US. A major risk factor in the development of atherosclerosis is hypercholesterolemia with an elevated level of cholesterol-carrying low-density-lipoprotein (LDL cholesterol or LDL-C) particles in the circulation. The metabolism of LDL cholesterol particles is highly regulated to balance the synthesis of cholesterol with the dietary intake to serve the need for cholesterol in the body. A key regulator in the turnover of LDL cholesterol is the LDL receptor (LDLR) that mediates cellular uptake of LDL particles and decreases the level of LDL cholesterol in the circulation, as illustrated by patients with familial hypercholesterolemia caused by LDLR deficiency or functional impairment.

A successful strategy to reduce LDL cholesterol plasma levels is to increase the cellular levels of LDLR, and today the most widely used medication to lower LDL cholesterol is statins. Statins inhibit the synthesis of cholesterol and up-regulate the expression of LDLR, thus overall resulting in decreased amounts of circulating LDL cholesterol. However, a considerable number of patients do not respond to or tolerate statins due to various side effects. Furthermore, statins also increase the expression of proprotein convertase subtilisin-like/kexin type 9 (PCSK9) that was recently identified as a potent negative regulator of LDLR (Seidah et al., 2014), thereby counteracting the beneficial effect on the LDL cholesterol.

Targeting of PCSK9 is a recent strategy for lowering plasma LDL-C (Lagace et al., 2006). The cellular level of the LDLR is reduced due to the ability of PCSK9 to bind the LDLR thereby impairing recycling and enhancing lysosomal degradation of the receptor. PCSK9 gain-of-function mutations lead to a significant increase in circulating LDL-C due to increased degradation of LDLR. In contrast, individuals with PCSK9 loss-of-function mutations show reduced levels of LDL-C and exhibit fewer incidents of coronary heart disease. Several leading pharmaceutical companies have obtained approval for therapeutic strategies targeting PCSK9 for the alleviation of hypercholesterolemia. Administration of PCSK9-specific antibodies directed against the LDLR-binding site of PCSK9 is reported to decrease LDL-C plasma levels in Phase III clinical trials (Mullard (2015) Nat Rev Drug Discov; Sheridan (2015) Nature Biotechnology). However, the PCSK9: LDLR binding constant is in the range of 120-620 nM (Cunningham et al., 2007; Fisher et al., 2007) while the PCSK9 plasma concentration is around 6 nM (Lakoski et al., 2009), rendering it highly unlikely that PCSK9 binds LDLR directly at physiologically relevant concentrations. In addition, PCSK9 only targets LDLR in the liver and not in e.g. steroid hormone producing tissues, which also express high levels of LDLR, suggesting the requirement of a liver-specific co-receptor (Seidah et al., 2014). Thus, LDLR is most likely not the primary PCSK9 receptor. Instead, an unknown receptor (receptor X) may capture circulating PCSK9 and subsequently deliver it to LDLR. Inhibition of PCSK9 binding to this receptor is therefore a superior strategy compared to inhibition of the PCSK9:LDLR interaction.

SUMMARY OF THE INVENTION

The present invention relates to the finding that LDLR is not the sole PCSK9 receptor on the surface of hepatocytes. The present inventors found that PCSK9 harbours a binding motif for heparan sulfate proteoglycans (HSPGs). Mutations introduced into this motif as well as inhibition of binding to HSPGs by heparin surprisingly protect the LDLR against PCSK9-induced degradation. Inhibition of the interaction between PCSK9 and HSPGs has superior therapeutic potential as compared to the clinical trials of a PCSK9 inhibitory antibody (Chan et al., 2009). Importantly, the HSPG-binding motif in PCSK9 is different from that of the LDLR-binding surface. HSPGs consist of a core protein substituted with one or more heparan sulfate glycosaminoglycan chains. Heparin is a type of heparan sulfate glycosaminoclycan. HSPGs are highly glycosylated cell surface proteins, which bind protein ligands having HSPG-binding motifs, creating local depots of e.g. growth factors (Xu and Esko, 2014). The data show that PCSK9 binds HSPG, and that the interaction is abolished by site-directed mutagenesis of the HSPG-binding motif in PCSK9, resulting in a PCSK9 mutant unable to bind heparin and exhibiting impaired capacity to degrade the LDLR. In addition, incubation of cells with heparin, heparin mimetics or monoclonal antibodies directed against the HSPG binding site in PCSK9 results in elevated levels of the LDLR, accompanied by increased concentration of PCSK9 in the media. Taken together, the results outlined in the present examples demonstrate that PCSK9 function is dependent on binding of HSPGs, and that the cellular level of LDLR is increased when the interaction between PCSK9 and HSPGs is abrogated.

Thus HSPGs function as critical co-receptors in PCSK9 mediated degradation of cell surface LDLR. The present findings show that HSPGs have a crucial function in PCSK9-induced down regulation of LDLR.

The site of interaction between PCSK9 and HSPGs can be targeted in blocking PCSK9 function, in particular in inhibiting the effect of PCSK9 on LDLR levels. Thus a new strategy in treatment of hypercholesterolemia and prevention of coronary heart diseases is disclosed.

In a first aspect, the invention relates to a compound capable of inhibiting binding of heparan sulfate proteoglycan receptors to PCSK9.

In another aspect, the invention relates to a compound as defined herein for the preparation of a medicament for the treatment of a disorder of lipoprotein metabolism.

In yet another aspect, the invention relates to a compound as defined herein for use as a medicament.

In yet another aspect, the invention relates to a compound as defined herein for use in a method of treatment of a disorder of lipoprotein metabolism in a subject in need thereof.

In yet another aspect, the invention relates to a method of treatment of a disorder of lipoprotein metabolism in a subject in need thereof, said method comprising administering to said subject a compound as defined herein.

In yet another aspect, the invention relates to a method of treatment of a disorder of lipoprotein metabolism such as the group consisting of dyslipidemia, hypercholesterolemia and heart coronary diseases in an individual in need thereof, the method comprising the steps of:

i. providing a tissue sample or a plasma sample isolated from said individual,
ii. determining the levels of LDLR in said tissue and/or the levels of PCSK9 and/or the levels of LDL-C in said plasma sample,
iii. correlating the expression level of step ii) with the levels of a control tissue sample or a control plasma sample,
iv. assessing a treatment regime,
v. administering to the individual a composition comprising a therapeutically effective amount of a composition as defined herein.

In yet another aspect, the invention relates to a method of inhibiting degradation of LDLR, said method comprising administering a compound as defined herein.

In yet another aspect, the invention relates to a pharmaceutical composition comprising a compound as defined herein.

In yet another aspect, the invention relates to a method of selecting an antibody specifically recognising and binding an epitope within the HSPG binding site of PCSK9 (SEQ ID NO: 1), said method comprising the steps of:
i. administering to a mammal a polypeptide fragment of PCSK9 or a polynucleotide fragment encoding a polypeptide fragment of PCSK9 comprising at least one amino acid residue of the domain consisting of amino acid residues 78 to 167 of SEQ ID NO: 1, such as at least 5, such as at least 10, such as at least 15, such as at least 20, such as at least 25, such as at least 30, such as at least 35, such as at least 40, such as at least 45, such as at least 50, such as at least 55, such as at least 60, such as at least 65, such as at least 70, such as at least 75, such as at least 80, such as at least all amino acids of the domain consisting of amino acid residues 78 to 167 of SEQ ID NO: 1;
ii. identifying and selecting antibodies recognising said polypeptide, and
iii. determining whether said selected antibodies are capable of displacing one or more reference antibodies in a competitive ELISA assay.

In yet another aspect, the invention relates to a method of selecting a peptide or a heparin analogue or mimetic capable of inhibiting binding of HSPGs such as heparin to PCSK9, said method comprising the steps of:
i. providing a plurality of peptides or heparin analogues or mimetics;
ii. incubating said plurality of peptides or heparin analogues or mimetics with cells derived from an LDLR-expressing cell line such as a hepatocyte-derived cell line in a medium;
iii. determining the levels of PCSK9 in said medium and/or the levels of LDLR of said cells;
iv. selecting the peptides or heparin analogues or mimetics resulting in the highest levels of PCSK9 and/or LDLR as determined in step iii.

In yet another aspect, the invention relates to a compound capable of selectively binding the compound as defined herein.

In yet another aspect, the invention relates to a method for producing the antibody as defined herein, said method comprising the steps of:
i. administering to a mammal a protein or a polynucleotide encoding a protein comprising the HSPG binding domain of PCSK9 or a fragment thereof or a functional equivalent thereof;
ii. selecting said antibody if it is able to bind to PCSK9 (SEQ ID NO: 1);
iii. selecting said antibody if it is unable to bind to mutated PCSK9, wherein said mutated PCSK9 is unable to bind to HSPG.

In another aspect, the invention relates to a method for reducing plasma LDL-C levels in a subject in need thereof, said method comprising the step of administering to said subject a compound or a pharmaceutical composition as defined herein.

****p<0.0001. (K) MST binding curve for PCSK9 and S-dC-36. Y axis: fluorescence signal. X axis S-dC-36 concentration. Circles: S-dC-36, $K_D$=4.8 µM. Squares: control.

Figure 10:
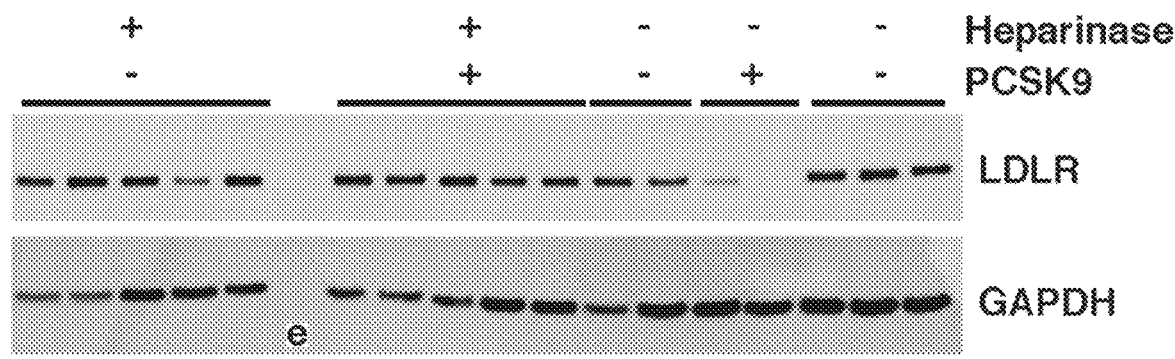
Figure 10:
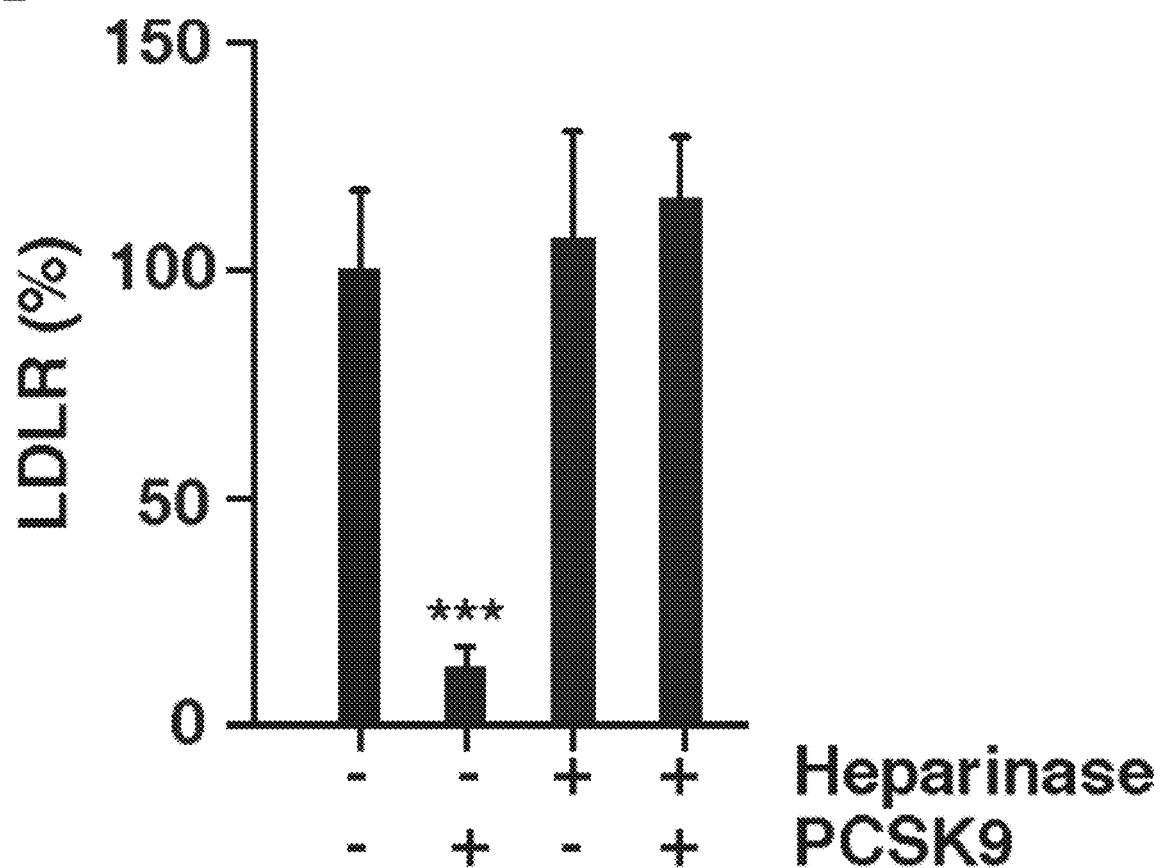
Figure 10:
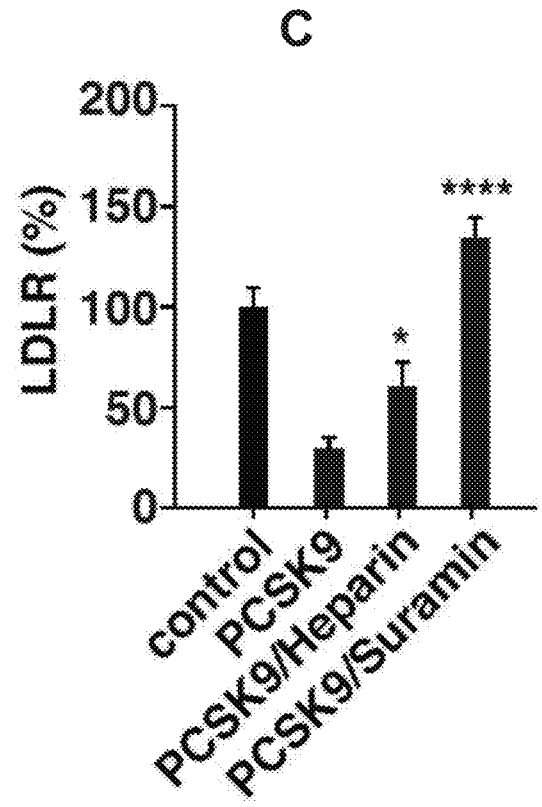
Figure 10:
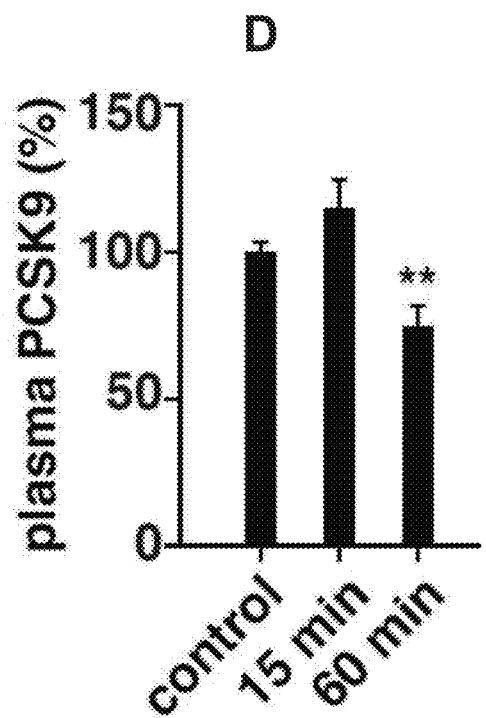

FIG. 10: Infusion of heparinase I prior injection of PCSK9 (10 µg) completely inhibits PCSK9 induced degradation of LDLR. Shown is a Western blot of representative samples (A) and bar graph quantification of LDLR (B). For Western blots, GAPDH is used as a loading control. e: empty lane. Control n=7, PCSK9 n=6, heparinase n=5, heparinase/PCSK9 n=5. Mice co-injected with PCSK9 (10 µg) and heparin (50 U) or suramin (300 µg) show significantly higher level of LDLR compared to mice injected with PCSK9 alone (C). Control n=15, PCSK9 n=10, PCSK9/heparin n=7, PCSK9/suramin n=3. (D) Plasma levels of PCSK9 after intravenous injection of heparin (50 u) as assessed by murine PCSK9 specific ELISA.

Figure 11:
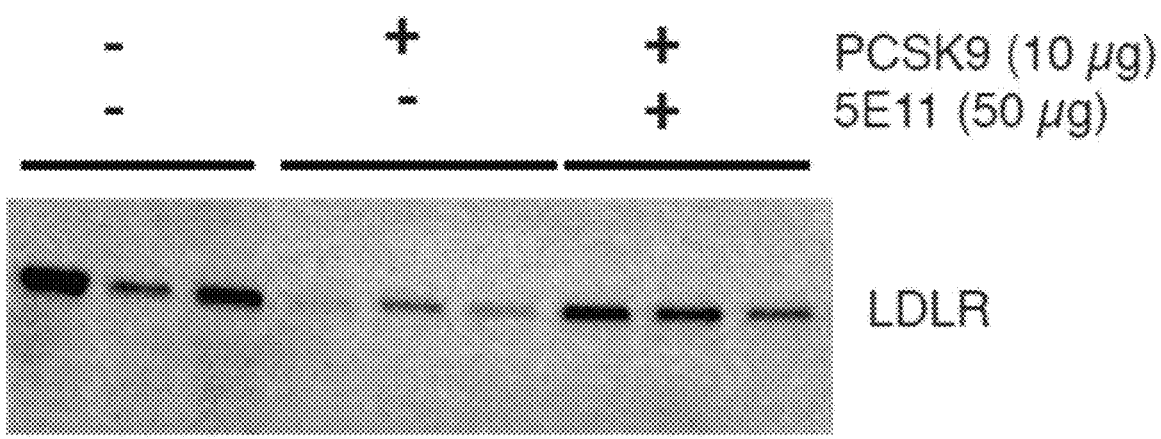

FIG. 11: LDLR levels in liver of mice 1 hour after intraveinous administration of 10 µg PCSK9 alone or in combination with 50 µg mAbs.

Figure 12:
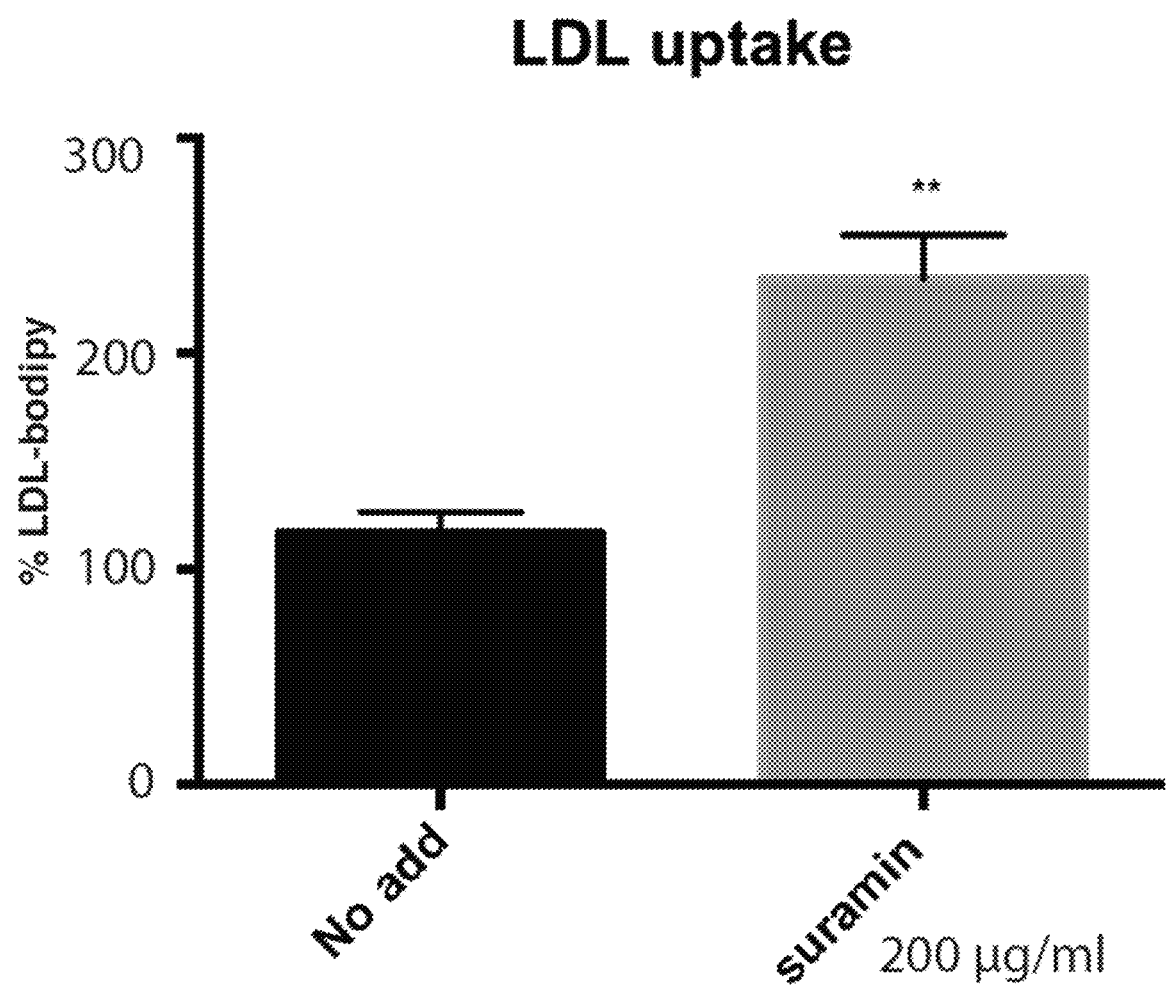

FIG. 12: Bar graphs showing the relative fluorescence signal in HepG2 cells after overnight incubation with suramin (200 µg/ml) following 4 hours incubation with 10 ng/ml LDL particles labeled with fluorescence dye Bodipy. Inhibition of PCSK9 with suramin increases the uptake of LDL two-fold.

Figure 13:
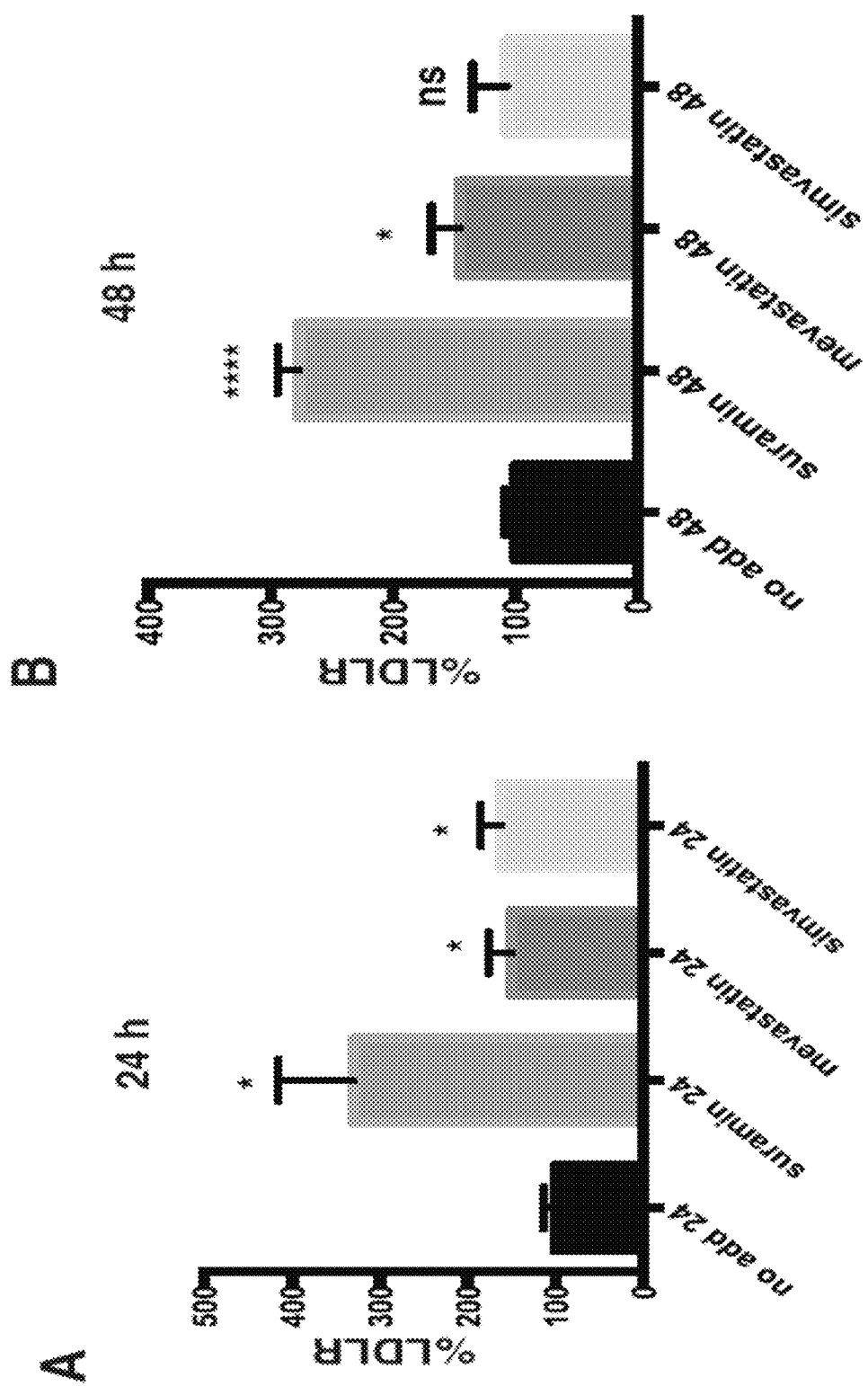

FIG. 13: A) and B) Bar graphs showing LDLR levels, as assessed by Western Blot, in HepG2 cells following 24 and 48 hours of incubation with 100 µM suramin or HMG CoA reductase inhibitors mevastatin and simvastatin. Cells incubated with suramin display a higher level of LDLR that cells incubated with statins.

DEFINITIONS

Heparin analogue: the term as used herein refers to compounds being structurally similar to heparin.

Heparin mimetic: the term herein refers to compounds behaving functionally like, i.e. mimicking, heparin. This term thus includes both compounds being structurally similar, but also compounds having different structure but same functionality as heparin, in the context of the present disclosure.

LDL-cholesterol (LDL-C) levels: The optimal LDL-C levels for a given individual vary depending on his/her underlying risk of heart disease. For healthy individuals, LDL-C levels should ideally be less than 2.6-3.3 mmol/L (or 100-129 mg/dL). Levels between 3.4 and 4.1 mmol/L or 130 and 159 mg/dL are borderline high, levels between 4.1 and 4.9 mmol/L or 160 and 189 mg/dL are high, and levels above 4.9 mmol/L or 189 mg/dL are very high. For individuals at risk of heart disease, levels below 2.6 mmol/L or 100 mg/dL are recommended, while levels below 1.8 mmol/L or 70 mg/dL are desirable for individuals at very high risk of heart disease.

Low-density lipoprotein receptor (LDLR) levels: Synthesis of LDLR in the cell is regulated by the level of free intracellular cholesterol; if cholesterol is in excess for the needs of the cell then the transcription of LDLR will be inhibited. LDLR levels can be estimated by methods known in the art, such as, but not limited to, Western blotting, RT-PCR an flow cytometry.

Low-molecular weight heparin: Natural heparin consists of molecular chains of varying lengths, or molecular weights. For example, chains of varying molecular weights, from 5000 to over 40,000 Daltons, make up polydisperse pharmaceutical-grade heparin. Low-molecular weight heparins, in contrast, consist of only short chains of polysaccharide. Low-molecular weight heparins are defined as heparin salts having an average molecular weight of less than 8000 Da and for which at least 60% of all chains have a molecular weight less than 8000 Da. These are obtained by various methods known to the person skilled in the art, such as fractionation or depolymerisation of polymeric heparin.

Lipoprotein metabolism disorder: the term refers to disorders of lipid homeostasis and disorders associated therewith, including by way of example hypercholesterolemia, hyperlipidemia, hypertriglyceridaemia, sitosterolemia, atherosclerosis, arteriosclerosis, coronary heart disease, metabolic syndrome, acute coronary syndrome, xanthoma, hypertension, angina, obesity, diabetes and vascular inflammation.

PCSK9 levels: plasma levels of PCSK9 vary from 30 to 3000 ng/mL in the general population, and median levels are in general higher in women than in men. PCSK9 levels correlate with LDL-C levels.

Phosphorothioates (or phosphorothioate oligonucleotides or S-oligos) are a DNA variant in which one of the non-bridging oxygens is replaced by a sulfur. The sulfurization of the internucleotide bond is thought to dramatically reduce the action of various nucleases and to increase the potential for crossing the lipid bilayer.

DETAILED DESCRIPTION OF THE INVENTION

The invention is as defined in the claims.

The present invention relates in a first aspect to a compound capable of inhibiting binding of HSPGs to PCSK9. It will be understood throughout this disclosure that compounds capable of inhibiting binding of HSPGs to variants of PCSK9 is also within the scope of the invention. By variant of PCSK9 is understood a polypeptide which has essentially the same sequence as SEQ ID NO: 1, for example variants having conservative substitutions of some residues of SEQ ID NO: 1.

In some embodiments, said compound specifically recognises and binds a region within the HSPG binding site of PCSK9 (SEQ ID NO: 1) that comprises at least one of amino acid residues 78 to 167 of PCSK9 (SEQ ID NO: 1), such as at least one of amino acid residues 78 to 92, such as at least one of amino acid residues 93 to 97, such as at least one of amino acid residues 98 to 103, such as at least one of amino acid residues 104 to 105, such as at least one of amino acid residues 106 to 135, such as at least one of amino acid residues 136 to 139, such as at least one of amino acid residues 140 to 164, such as at least one of amino acid residues 165 to 167 of PCSK9 (SEQ ID NO: 1).

Herein is provided a compound that specifically recognises and binds a region within the HSPG binding site of PCSK9 (SEQ ID NO: 1) that comprises at least one of amino acid residues 78 to 167 of PCSK9 (SEQ ID NO: 1), such as at least 2, such as at least 5, such as at least 10, such as at least 15, such as at least 20, such as at least 25, such as at least 30, such as at least 35, such as at least 40, such as at least 45, such as at least 50, such as at least 55, such as at least 60, such as at least 65, such as at least 70, such as at least 75, such as at least 80, such as at least 85, such as all of amino acid residues 78 to 167 of PCSK9 (SEQ ID NO: 1).

In some embodiments, the compound specifically recognises and binds a region comprising at least one of amino acid residues 78 to 92, such as at least one of amino acid residues 93 to 97, such as at least one of amino acid residues 98 to 103, such as at least one of amino acid residues 104 to 105, such as at least one of amino acid residues 106 to 135, such as at least one of amino acid residues 136 to 139, such as at least one of amino acid residues 140 to 164, such as at least one of amino acid residues 165 to 167 of PCSK9 (SEQ ID NO: 1).

In some embodiments, the compound specifically recognises and binds a region comprising at least one of amino acid residues 78 to 92, such as amino acid residues 93 to 97, such as amino acid residues 98 to 103, such as amino acid residues 104 to 105, such as amino acid residues 106 to 135, such as amino acid residues 136 to 139, such as amino acid residues 140 to 164, such as amino acid residues 165 to 167 of PCSK9 (SEQ ID NO: 1).

Thus in one embodiment, the compound specifically recognises and binds a region within the HSPG binding site of PCSK9 comprising amino acid residues 78 to 167. In another embodiment, the compound specifically recognises and binds a region within the HSPG binding site of PCSK9 comprising amino acid residues 78 to 95. In another embodiment, the compound specifically recognises and binds a region within the HSPG binding site of PCSK9 comprising amino acid residues 96 to 100. In another embodiment, the compound specifically recognises and binds a region within the HSPG binding site of PCSK9 comprising amino acid residues 101 to 105. In another embodiment, the compound specifically recognises and binds a region within the HSPG binding site of PCSK9 comprising amino acid residues 106 to 110. In another embodiment, the compound specifically recognises and binds a region within the HSPG binding site of PCSK9 comprising amino acid residues 111 to 115. In another embodiment, the compound specifically recognises and binds a region within the HSPG binding site of PCSK9 comprising amino acid residues 116 to 120. In another embodiment, the compound specifically recognises and binds a region within the HSPG binding site of PCSK9 comprising amino acid residues 121 to 125. In another embodiment, the compound specifically recognises and binds a region within the HSPG binding site of PCSK9 comprising amino acid residues 126 to 130. In another embodiment, the compound specifically recognises and binds a region within the HSPG binding site of PCSK9 comprising amino acid residues 131 to 135. In another embodiment, the compound specifically recognises and binds a region within the HSPG binding site of PCSK9 comprising amino acid residues 136 to 140. In another embodiment, the compound specifically recognises and binds a region within the HSPG binding site of PCSK9 comprising amino acid residues 141 to 145. In another embodiment, the compound specifically recognises and binds a region within the HSPG binding site of PCSK9 comprising amino acid residues 146 to 150. In another embodiment, the compound specifically recognises and binds a region within the HSPG binding site of PCSK9 comprising amino acid residues 151 to 155. In another embodiment, the compound specifically recognises and binds a region within the HSPG binding site of PCSK9 comprising amino acid residues 156 to 160. In another embodiment, the compound specifically recognises and binds a region within the HSPG binding site of PCSK9 comprising amino acid residues 161 to 167.

Thus there is provided a compound which binds to one or more amino acids selected from the group consisting of R93, R96, R97, R104, R105, K136, H139, R165 and R167 of PCSK9 (SEQ ID NO: 1), such as one amino acid, such as two amino acids, such as three amino acids, such as four amino acids, such as five amino acids, such as six amino acids, such as seven amino acids, such as eight amino acids, such as all of the amino acids selected from the group consisting of R93, R96, R97, R104, R105, K136, H139, R165 and R167 of PCSK9.

Thus in one embodiment, the compound binds to R93 of PCSK9. In another embodiment, the compound binds to R96 of PCSK9. In another embodiment, the compound binds to R97 of PCSK9. In another embodiment, the compound binds to R104 of PCSK9. In another embodiment, the compound binds to R105 of PCSK9. In another embodiment, the compound binds to K136 of PCSK9. In another embodiment, the compound binds to H139 of PCSK9. In another embodiment, the compound binds to R165 of PCSK9. In another embodiment, the compound binds to R167 of PCSK9.

In one embodiment, the compound binds to R96 and to R97 of PCSK9. In another embodiment, the compound binds to R104 and R105 of PCSK9. In another embodiment, the compound binds to K136 and H139 of PCSK9. In another embodiment, the compound binds to R93 and H139 of PCSK9. In another embodiment, the compound binds to R93, R104, R105 and H139 of PCSK9. In another embodiment, the compound binds to R165 and R167 of PCSK9. In another embodiment, the compound binds to R93, R96, R97, R104, R105 and H139 of PCSK9.

Antibodies

Also disclosed is a compound as defined herein, wherein the compound is an antibody or functional equivalent thereof.

An antibody of the invention may be any polypeptide or protein capable of recognising and binding an antigen as defined herein. Preferably, said antibody is capable of specifically binding said antigen. By the term "specifically binding" is meant binding with at least 10 times higher affinity to the antigen than to a non-specific antigen (e.g. BSA).

The antibody may be a naturally occurring antibody or a functional equivalent thereof. A naturally occurring antibody is a heterotetrameric glycoprotein capable of recognising and binding an antigen. It comprises two identical heavy (H) chains and two identical light (L) chains inter-connected by disulfide bonds. Each heavy chain comprises or preferably consists of a heavy chain variable region (abbreviated herein as $V_H$) and a heavy chain constant region (abbreviated herein as $C_H$). Each light chain comprises or preferably consists of a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Each $V_H$ and $V_L$ comprises and preferably consists of three CDRs and four FRs, arranged from amino-terminus to carboxy-terminus in the following order: FR1, CDR1, FR2, CDR2, FR3, CDR3, FR4.

The naturally occurring antibody may also be a heavy-chain antibody (HCAbs) as produced by camelids (camels, dromedaries and llamas). HCAbs are homodimers of heavy chains only, devoid of light chains and the first constant domain (Hamers-Casterman et al., 1993). Other naturally occurring antibodies may be devoid of light chains as is the case for the New or Nurse Shark Antigen Receptor (NAR) protein, which exists as a dimer of two heavy chains with no associated light chains. Each chain is composed of one variable (V) and five constant domains. The NAR proteins constitute a single immunoglobulin variable-like domain (Greenberg et al., 1995.) which is much lighter than an antibody molecule.

Naturally occurring antibodies according to the invention may consist of one heterotetramer or they may comprise several identical heterotetramers. Thus, the naturally occurring antibody according to the invention may for example be selected from the group consisting of IgG, IgM, IgA, IgD and IgE. The subunit structures and three-dimensional configurations of these different classes of immunoglobulins are well known. In a preferred embodiment of the invention the antibody is IgG, e.g. IgG-1, IgG-2, IgG-3 and IgG-4.

The antibody may be a monoclonal antibody, such as a naturally occurring monoclonal antibody. In other embodiments, the antibody may be polyclonal antibodies, such as naturally occurring polyclonal antibodies. Monoclonal and polyclonal antibodies are discussed in further detail herein below.

Naturally occurring antibodies may be antibodies of a particular species, for example the antibody may be a murine, a rat, a rabbit, a goat, a sheep, a chicken, a donkey, a camelid or a human antibody. The antibody may be a murine or rat monoclonal antibody. The antibody may however also be a hybrid between antibodies from several species, for example the antibody may be a chimeric antibody, such as a humanised antibody. Human and humanised antibodies are discussed in further detail herein below.

Antigen Binding Fragments of Antibodies

Antigen binding fragments of antibodies are fragments of antibodies retaining the ability to specifically bind to an antigen. Thus in some embodiments the functional equivalent of an antibody comprises a binding fragment of an antibody. Preferably, said fragment is an antigen binding fragment of a naturally occurring antibody. It has been shown that the antigen-binding function of an antibody can be performed by fragments of a full-length antibody. Examples of antigen binding fragments of naturally occurring antibodies include for example (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) an Fd fragment consisting of the $V_H$ and $C_{H1}$ domains; (iv) an Fv fragment consisting of the $V_L$ and $V_H$ domains of a single arm of an antibody or (v) a dAb fragment (Ward et al., 1989), which consists of a $V_H$ domain. Fab fragments may be prepared by papain digestion. F(ab')$_2$ fragments may be prepared by pepsin treatment.

The antigen binding fragment of an antibody preferably comprises at least one complementarity determining region (CDR) or more preferably a combination of two or more isolated CDRs which may optionally be joined by a synthetic linker.

A further example of an antigen binding fragment of an antibody is binding-domain immunoglobulin fusion proteins comprising (i) an antigen binding site fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The antigen binding site can be a heavy chain variable region or a light chain variable region. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The antigen binding fragment of an antibody may also be a diabody, which are small antibody fragments with two antigen-binding sites. Diabodies preferably comprises a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993.

Heterospecific Antibodies

The antibody disclosed herein may also be a "heterospecific antibody", such as a bispecific antibody. A bispecific antibody is a protein or polypeptide, which comprises two different antigen binding sites with different specificities. For example, the bispecific antibody may recognise and bind to (a) a first epitope within a first antigen and (b) a second epitope within a second antigen; or it may recognise and bind to two different epitopes within the same antigen. The term "heterospecific antibody" is intended to include any protein or polypeptide, which has more than two different antigen binding sites with different specificities. For example, the heterospecific antibody may recognise and bind to (a) a first epitope on a first antigen, (b) a second epitope on a second antigen and (c) a third epitope on a third antigen; or it may recognise and bind to (a) a first epitope on a first antigen and (b) a second and third epitope on a second antigen; or it may recognise and bind to different epitopes on the same antigen. Accordingly, the invention includes, but is not limited to, bispecific, trispecific, tetraspecific, and other multispecific antibodies which are directed to different epitopes on the same or on different antigens.

Bispecific antibodies may for example be prepared starting from monoclonal antibodies, for example by fusing two hybridoma's in order to combine their specificity, by chemical crosslinking or using recombinant technologies. For example the $V_H$ and $V_L$ of two different antibodies (1 and 2) may be linked by recombinant means to form "cross-over" chains $V_H1$-$V_L2$ and $V_H2$-$V_L1$, and then dimerised to reassemble both antigen-binding sites (see WO 94/09131). Bispecific antibodies may also be prepared by genetically linking two single chain antibodies with different specificities as for example described in WO 94/13806. Also two antigen binding fragments of an antibody may be linked.

Human and Humanised Antibodies

It is not always desirable to use non-human antibodies for human therapy, accordingly the antibody according to the invention may be a human antibody or a humanised antibody.

A human antibody as understood herein is an antibody, which is obtained from a system using human immunoglobulin sequences. Human antibodies may for example be antibodies isolated from an animal (e.g., a mouse) that is transgenic or transchromosomal for human immunoglobulin genes or a hybridoma prepared therefrom. Human antibodies may also be isolated from a host cell transformed to express the antibody, e.g., from a transfectoma. Human antibodies may also be isolated from a recombinant, combinatorial human antibody library.

Human antibodies have variable and constant regions derived from human germline immunoglobulin sequences. In certain embodiments, however, such recombinant human antibodies can be subjected to in vitro mutagenesis or in vivo somatic mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A human antibody is preferably at least 90%, more preferably at least 95%, even more preferably at least 96%, 97%, 98%, or 99% identical in amino acid sequence to the amino acid sequence encoded by a wild type human immunoglobulin gene. Said transgenic or transchromosomal animal may contain a human immunoglobulin gene minilocus that encodes unrearranged human heavy (p and/or y) and K light chain immunoglobulin sequences. Furthermore, the animal may contain one or more mutations that inactivate the endogenous heavy and light chain loci. Examples of such animals are described in Lonberg et al. (1994) and WO 02/43478.

The antibody disclosed herein may be a chimeric antibody, i.e. an antibody comprising regions derived from different species. The chimeric antibody may for example comprise variable regions from one animal species and constant regions from another animal species. For example, a chimeric antibody can be an antibody having variable regions which derive from a mouse monoclonal antibody and constant regions which are human. Such antibodies may also be referred to as humanised antibodies. Thus, the antibody may also be a humanised antibody, which is encoded partly by sequences obtained from human germline immunoglobulin sequences and partly from other sequences. Said other sequences are preferably germline immunoglobulines from other species, more preferably from other mammalian species. In particular a humanised antibody may be an antibody in which the antigen binding site is derived from an immunoglobulin from a non-human species, preferably from a non-human mammal, e.g. from a mouse or a rat, whereas some or all of the remaining immunoglobulin-derived parts of the molecule are derived from a human immunoglobulin. The antigen binding site from said non-human species may for example consist of a complete $V_L$ or $V_H$ or both, or one or more CDRs grafted onto appropriate human framework regions in $V_L$ or $V_H$ or both. Thus, in a humanized antibody, the CDRs can be from a mouse or rat monoclonal antibody and the other regions of the antibody are of human origin.

Monoclonal Antibodies

Monoclonal antibodies (MAbs) refer to a population of antibodies, wherein the antibody molecules are similar and thus recognise and bind to the same epitope. Monoclonal antibodies are in general produced by a host cell line and frequently by a hybridoma cell line. Methods of making monoclonal antibodies and antibody-synthesizing hybridoma cells are well known to those skilled in the art. Antibody producing hybridomas may for example be prepared by fusion of an antibody producing B lymphocytes with an immortalized B-lymphocyte cell line. Monoclonal antibodies according to the present invention may for example be prepared by the standard somatic cell hybridization technique of Kohler and Milstein, *Nature* 256:495 (1975) or as described in Antibodies: A Laboratory Manual, By Ed Harlow and David Lane, *Cold Spring Harbor Laboratory Press,* 1988. Said monoclonal antibodies may be derived from any suitable mammalian species, however frequently the monoclonal antibodies will be rodent antibodies for example murine or rat monoclonal antibodies.

Polyclonal Antibodies

Polyclonal antibodies refer to a population of antibodies comprising a mixture of different antibody molecules recognising and binding to a specific given antigen, hence polyclonal antibodies may recognise different epitopes within said antigen. In general polyclonal antibodies are purified from the serum of an animal, preferably a mammal, which previously has been immunized with the antigen. Polyclonal antibodies may for example be prepared by any of the methods described in Antibodies: A Laboratory Manual, By Ed Harlow and David Lane, *Cold Spring Harbor Laboratory Press,* 1988.

Recombinant Antibodies

The antibody may also be a recombinant antibody, i.e. an antibody prepared, expressed, created or isolated by recombinant means. Recombinant antibodies according to the invention may be for example be produced using a synthetic library or by phage display. In some embodiments, the antibody is produced in a recombinant cell. The recombinant cell may be a microorganism selected from the group comprising bacteria and eukaryotic microorganisms. Recombinant antibodies may be produced in microbial host organisms, such as bacteria, yeasts or cultures of cells derived from multicellular organisms. Frequently, *Escherichia coli* is useful as host organism. Frequently recombinant antibodies are fragments of naturally occurring antibodies comprising at least one antigen binding site, such as a Fab fragment, a F(ab')$_2$, a Fv fragment or the recombinant antibody is a scFV. Thus in some embodiments the antibody is a fragment of a naturally occurring antibody comprising at least one antigen binding site, such as a Fab fragment, a F(ab')$_2$, a Fv fragment. In other embodiments, the recombinant antibody is a scFV.

Recombinant antibodies may be identified using various systems, such as phage display or ribosome display. The starting point of phage display is usually a library of antibodies, such as single chain antibodies or fragments of naturally occurring antibodies expressed by a phage. Various different kinds of phages are suitable for use in phage display, e.g. M13, fd filamentous phage, T4, T7 or λ phage. Phagemids may also be used, but that usually requires use of a helper phage. Typically the library comprises in the range of $10^7$ to $10^{15}$, such as $10^9$ to $10^{11}$ different phages. The antibodies may be either of naive or immune origin. The antibodies of the library may be fused to a phage coat protein (e.g. g3p or g8p) in order to ensure display on the surface. Thus, the antibody (fragment) may be encoded by a nucleic acid sequence, which is cloned upstream or downstream of a nucleic acid encoding a phage coat protein, which is operably linked to a suitable promoter.

The genomic information coding for antibody e.g. for the antibody variable domains may be obtained from B cells of non-immunised or immunised donors using recombinant DNA technology to amplify the $V_H$ and $V_L$ gene segments and cloning into an appropriate phage. Synthetic libraries may be prepared by rearranging $V_H$ and $V_L$ gene segments in vitro and/or by introducing artificial sequences into $V_H$ and $V_L$ gene segments. For example synthetic libraries may be prepared using a $V_H$ and $V_L$ gene framework, but introducing into this artificial complementarity determining regions (CDRs), which may be encoded by random oligonucleotides. The library may also be different libraries, which are then combined in the host cell. Thus, one library may comprise heavy chain sequences, such as the heavy chain Fv fragment or Fab fragment or $V_H$ and the other light chain sequences, such as the light chain Fv fragment or Fab fragment $V_L$. Typically several rounds of selection, e.g. 2 to 5, such as 2 to 3 are performed. This may be done by immobilising the antigen, contacting the antigen with the phage and isolating the bound phages. The antigen may be immobilised on any suitable solid surface, such as a plastic surface, beads (such as magnetic beads), a resin in a column, or it may be expressed on the surface of a cell.

Single Chain Antibodies

Naturally occurring antibodies are heterotetramers. However, the antibody as defined herein may also be a single polypeptide comprising one or more antigen binding sites.

Such antibodies are also referred to as "single chain antibodies". Thus the antibody may also be a single chain antibody. Single chain antibodies may comprise the two domains of the Fv fragment, $V_L$ and $V_H$. To obtain such single chain antibodies the genes encoding the $V_L$ and $V_H$ may be joined, using recombinant methods. Usually they are separated by a synthetic linker, for example a linker of 5 to 100, such as of 5 to 50, for example of 25 amino acids. Said linker may either connect the N-terminus of the $V_H$ with the C-terminus of the $V_L$, or vice versa. This enables production of a single protein chain in which the $V_L$ and $V_H$ regions pair to form monovalent antibody like molecules (also known as single chain antibodies or single chain Fv (scFv); see e.g., Bird et al. (1988) *Science* 242:423-426; and Huston et al. (1988) *Proc. Natl. Acad. Sci. USA* 85:5879-5883).

The single chain antibody may also be a divalent antibody, e.g. a single peptide chain comprising two $V_H$ and two $V_L$ regions, which may be linked two by two by a linker. The single chain antibody may also be a multivalent antibody, e.g. a single peptide chain comprising multiple $V_H$ and multiple $V_L$ regions, which may be linked two by two by a linker. The $V_H$ and $V_L$ regions may be identical or different, yielding monospecific or heterospecific antibodies, respectively. Said $V_H$ and said $V_L$ may be a naturally occurring $V_H$ or $V_L$, or a synthetic $V_H$ and $V_L$ comprising at least one antigen binding site. Preferably said $V_H$ and $V_L$ are naturally occurring $V_H$ and $V_L$.

The compound disclosed herein may be a monoclonal or polyclonal antibody. The antibody may originate from any organism known in the art to be suitable for the production of antibodies, such as live organisms, for example mice, sheep, rabbit, or cell cultures such as bacterial cells, yeast cells, plant cells, insect cells or mammalian cell lines such as CHO cells. The antibody may be humanised. Preferably the antibody is a murine monoclonal antibody.

Also within the scope of the invention are functional equivalents which comprise a binding fragment of an antibody. The fragment may be selected from the group consisting of Fab, Fab', $F(ab)_2$ and Fv fragments such as ScFv fragments. The functional equivalent may also be a single chain antibody. Other embodiments relate to functional equivalents that e.g. comprise or consist of the binding fragment of an antibody binding to the HSPG binding domain of PCSK9 as detailed above. In some embodiments the functional equivalent may further comprise engineered domains which may for example increase the half-life, the stability, the bioavailability, the solubility or other relevant characteristics of the antibody fragment. For example, it is known in the art that engineered intradomain sulphide bonds can stabilise antibodies (Wozniak-Knopp et al. 2012). Other methods of stabilisation include e.g. the use of a peptide linker between the $V_H$ and the $V_L$ domains, resulting in stabilisation of Fv fragments (Reiter et al., 1994).

The functional equivalent may also be an antibody mimetic, or a small molecule mimicking an antibody. Antibody mimetics are organic compounds, including, but not limited to, nucleic acids, that can specifically bind antigens, but that are not structurally related to antibodies. They are usually artificial peptides or proteins, typically with a molar mass of about 3 to 20 kDa. Some types have an antibody-like β-sheet structure. Antibody mimetics sometimes display better solubility, tissue penetration, stability towards heat and enzymes compared to antibodies, as well as comparatively low production costs.

Thus is provided an antibody or functional equivalent thereof, which specifically recognises and binds an epitope within the HSPG binding site of PCSK9 (SEQ ID NO: 1) that comprises at least one of amino acid residues 78 to 167 of PCSK9 (SEQ ID NO: 1), such as at least 2, such as at least 5, such as at least 10, such as at least 15, such as at least 20, such as at least 25, such as at least 30, such as at least 35, such as at least 40, such as at least 45, such as at least 50, such as at least 55, such as at least 60, such as at least 65, such as at least 70, such as at least 75, such as at least 80, such as at least 85, such as all of amino acid residues 78 to 167 of PCSK9 (SEQ ID NO: 1).

In some embodiments, the antibody or functional equivalent thereof specifically recognises and binds an epitope comprising at least one of amino acid residues 78 to 92, such as at least one of amino acid residues 93 to 97, such as at least one of amino acid residues 98 to 103, such as at least one of amino acid residues 104 to 105, such as at least one of amino acid residues 106 to 135, such as at least one of amino acid residues 136 to 139, such as at least one of amino acid residues 140 to 164, such as at least one of amino acid residues 165 to 167 of PCSK9 (SEQ ID NO: 1).

In some embodiments, the antibody or functional equivalent thereof specifically recognises and binds an epitope comprising at least one of amino acid residues 78 to 92, such as amino acid residues 93 to 97, such as amino acid residues 98 to 103, such as amino acid residues 104 to 105, such as amino acid residues 106 to 135, such as amino acid residues 136 to 139, such as amino acid residues 140 to 164, such as amino acid residues 165 to 167 of PCSK9 (SEQ ID NO: 1).

Thus in one embodiment, the antibody or functional equivalent thereof specifically recognises and binds an epitope within the HSPG binding site of PCSK9 comprising amino acid residues 78 to 167. In another embodiment, the antibody or functional equivalent thereof specifically recognises and binds an epitope within the HSPG binding site of PCSK9 comprising amino acid residues 78 to 95. In another embodiment, the antibody or functional equivalent thereof specifically recognises and binds an epitope within the HSPG binding site of PCSK9 comprising amino acid residues 96 to 100. In another embodiment, the antibody or functional equivalent thereof specifically recognises and binds an epitope within the HSPG binding site of PCSK9 comprising amino acid residues 101 to 105. In another embodiment, the antibody or functional equivalent thereof specifically recognises and binds an epitope within the HSPG binding site of PCSK9 comprising amino acid residues 106 to 110. In another embodiment, the antibody or functional equivalent thereof specifically recognises and binds an epitope within the HSPG binding site of PCSK9 comprising amino acid residues 111 to 115. In another embodiment, the antibody or functional equivalent thereof specifically recognises and binds an epitope within the HSPG binding site of PCSK9 comprising amino acid residues 116 to 120. In another embodiment, the antibody or functional equivalent thereof specifically recognises and binds an epitope within the HSPG binding site of PCSK9 comprising amino acid residues 121 to 125. In another embodiment, the antibody or functional equivalent thereof specifically recognises and binds an epitope within the HSPG binding site of PCSK9 comprising amino acid residues 126 to 130. In another embodiment, the antibody or functional equivalent thereof specifically recognises and binds an epitope within the HSPG binding site of PCSK9 comprising amino acid residues 131 to 135. In another embodiment, the antibody or functional equivalent thereof specifically recognises and binds an epitope within the HSPG binding site of PCSK9 comprising amino acid residues 136 to 140. In another embodiment, the antibody or functional equivalent thereof specifically recognises and binds an epitope within the HSPG binding site of PCSK9 comprising amino acid residues 141 to 145. In another embodiment, the antibody or functional equivalent thereof specifically recognises and binds an epitope within the HSPG binding site of PCSK9 comprising amino acid residues 146 to 150. In another embodiment, the antibody or functional equivalent thereof specifically recognises and binds an epitope within the HSPG binding site of PCSK9 comprising amino acid residues 151 to 155. In another embodiment, the antibody or functional equivalent thereof specifically recognises and binds an epitope within the HSPG binding site of PCSK9 comprising amino acid residues 156 to 160. In another embodiment, the antibody or functional equivalent thereof specifically recognises and binds an epitope within the HSPG binding site of PCSK9 comprising amino acid residues 161 to 167.

Thus there is provided an antibody or functional equivalent thereof which binds to one or more amino acids selected from the group consisting of R93, R96, R97, R104, R105, K136, H139, R165 and R167 of PCSK9 (SEQ ID NO: 1), such as one amino acid, such as two amino acids, such as three amino acids, such as four amino acids, such as five amino acids, such as six amino acids, such as seven amino acids, such as eight amino acids, such as all of the amino acids selected from the group consisting of R93, R96, R97, R104, R105, K136, H139, R165 and R167 of PCSK9.

Thus in one embodiment, the antibody or functional equivalent thereof binds to R93 of PCSK9. In another embodiment, the antibody or functional equivalent thereof binds to R96 of PCSK9. In another embodiment, the compound binds to R97 of PCSK9. In another embodiment, the antibody or functional equivalent thereof binds to R104 of PCSK9. In another embodiment, the antibody or functional equivalent thereof binds to R105 of PCSK9. In another embodiment, the antibody or functional equivalent thereof binds to K136 of PCSK9. In another embodiment, the antibody or functional equivalent thereof binds to H139 of PCSK9. In another embodiment, the antibody or functional equivalent thereof binds to R165 of PCSK9. In another embodiment, the antibody or functional equivalent thereof binds to R167 of PCSK9.

In one embodiment, the antibody or functional equivalent thereof binds to R96 and to R97 of PCSK9. In another embodiment, the antibody or functional equivalent thereof binds to R104 and R105 of PCSK9. In another embodiment, the antibody or functional equivalent thereof binds to K136 and H139 of PCSK9. In another embodiment, the antibody or functional equivalent thereof binds to R93 and H139 of PCSK9. In another embodiment, the antibody or functional equivalent thereof binds to R93, R104, R105 and H139 of PCSK9. In another embodiment, the antibody or functional equivalent thereof binds to R165 and R167 of PCSK9. In another embodiment, the antibody or functional equivalent thereof binds to R93, R96, R97, R104, R105 and H139 of PCSK9.

In a particular embodiment, the antibody is a monoclonal antibody. In one embodiment, the antibody is a murine monoclonal antibody. In some embodiments, the antibody or functional equivalent thereof has been humanised. The antibody may be a single chain antibody.

In some embodiments, the antibody is a bispecific antibody. In one embodiment, the bispecific antibody is capable of recognising and binding the HSPG binding site of PCSK9 as detailed above but is also capable of binding and recognising the LDLR binding site of PCSK9 so that binding of such an antibody to PCSK9 inhibits binding of HSPG and of LDLR to PCSK9. Without being bound by theory, the LDLR binding site comprises residue 194 (A194) and the domain comprising residues 367 to 381 of PCSK9 (SEQ ID NO: 1), in particular P379. Thus in some embodiments, the compound is a bispecific antibody capable of binding to the HSPG binding site of PCSK9 as described above and capable of binding to at least one amino acid residue of the LDLR binding domain, where the at least one amino acid residue of the LDLR binding domain is residue 194 of SEQ ID NO: 1 or is comprised within the domain comprising residues 367 to 381 of SEQ ID NO: 1.

In some embodiments, the antibody is not capable of binding to the LDLR-binding domain of PCSK9.

Thus is also disclosed an antibody or antigen-binding fragment thereof comprising:
  (i) a heavy chain variable region or a humanized version thereof, comprising at least one of the three CDRs as defined by SEQ ID NO: 10, SEQ ID NO: 11 or SEQ ID NO: 12, and
  (ii) a light chain variable region comprising or a humanized version thereof, comprising at least one of the three CDRs as defined by SEQ ID NO: 13, SEQ ID NO: 14 or SEQ ID NO: 15.

In some embodiments, the heavy chain variable region or humanized version thereof comprises one of CDR1 (SEQ ID NO: 10), CDR2 (SEQ ID NO: 11) and CDR3 (SEQ ID NO: 12), and a light chain variable region or a humanized version thereof.

In some embodiments, the heavy chain variable region or humanized version thereof comprises one of CDR1 (SEQ ID NO: 10), CDR2 (SEQ ID NO: 11) and CDR3 (SEQ ID NO: 12), and a light chain variable region or a humanized version thereof, comprising at least one of CDR1 (SEQ ID NO: 13), CDR 2 (SEQ ID NO: 14) or CDR3 (SEQ ID NO: 15).

In some embodiments, the heavy chain variable region or humanized version thereof comprises one of CDR1 (SEQ ID NO: 10), CDR2 (SEQ ID NO: 11) and CDR3 (SEQ ID NO: 12), and a light chain variable region or a humanized version thereof, comprising at least two of CDR1 (SEQ ID NO: 13), CDR 2 (SEQ ID NO: 14) or CDR3 (SEQ ID NO: 15).

In some embodiments, the heavy chain variable region or humanized version thereof comprises one of CDR1 (SEQ ID NO: 10), CDR2 (SEQ ID NO: 11) and CDR3 (SEQ ID NO: 12), and a light chain variable region comprising or a humanized version thereof, comprising all of CDR1 (SEQ ID NO: 13), CDR 2 (SEQ ID NO: 14) and CDR3 (SEQ ID NO: 15).

In some embodiments, the heavy chain variable region or humanized version thereof comprises two of CDR1 (SEQ ID NO: 10), CDR2 (SEQ ID NO: 11) and CDR3 (SEQ ID NO: 12), and a light chain variable region or a humanized version thereof.

In some embodiments, the heavy chain variable region or humanized version thereof comprises two of CDR1 (SEQ ID NO: 10), CDR2 (SEQ ID NO: 11) and CDR3 (SEQ ID NO: 12), and a light chain variable region or a humanized version thereof, comprising at least one of CDR1 (SEQ ID NO: 13), CDR 2 (SEQ ID NO: 14) or CDR3 (SEQ ID NO: 15).

In some embodiments, the heavy chain variable region or humanized version thereof comprises two of CDR1 (SEQ ID NO: 10), CDR2 (SEQ ID NO: 11) and CDR3 (SEQ ID NO: 12), and a light chain variable region or a humanized version thereof, comprising at least two of CDR1 (SEQ ID NO: 13), CDR 2 (SEQ ID NO: 14) or CDR3 (SEQ ID NO: 15).

In some embodiments, the heavy chain variable region or humanized version thereof comprises two of CDR1 (SEQ ID NO: 10), CDR2 (SEQ ID NO: 11) and CDR3 (SEQ ID NO: 12), and a light chain variable region comprising or a humanized version thereof, comprising all of CDR1 (SEQ ID NO: 13), CDR 2 (SEQ ID NO: 14) and CDR3 (SEQ ID NO: 15).

In some embodiments, the heavy chain variable region or humanized version thereof comprises all of CDR1 (SEQ ID NO: 10), CDR2 (SEQ ID NO: 11) and CDR3 (SEQ ID NO: 12), and a light chain variable region or a humanized version thereof.

In some embodiments, the heavy chain variable region or humanized version thereof comprises all of CDR1 (SEQ ID NO: 10), CDR2 (SEQ ID NO: 11) and CDR3 (SEQ ID NO: 12), and a light chain variable region or a humanized version thereof, comprising at least one of CDR1 (SEQ ID NO: 13), CDR 2 (SEQ ID NO: 14) or CDR3 (SEQ ID NO: 15).

In some embodiments, the heavy chain variable region or humanized version thereof comprises all of CDR1 (SEQ ID NO: 10), CDR2 (SEQ ID NO: 11) and CDR3 (SEQ ID NO: 12), and a light chain variable region or a humanized version thereof, comprising at least two of CDR1 (SEQ ID NO: 13), CDR 2 (SEQ ID NO: 14) or CDR3 (SEQ ID NO: 15).

In some embodiments, the heavy chain variable region or humanized version thereof comprises all of CDR1 (SEQ ID NO: 10), CDR2 (SEQ ID NO: 11) and CDR3 (SEQ ID NO: 12), and a light chain variable region comprising or a humanized version thereof, comprising all of CDR1 (SEQ ID NO: 13), CDR 2 (SEQ ID NO: 14) and CDR3 (SEQ ID NO: 15).

In some embodiments, the antibody or antigen-binding fragment thereof comprises a heavy chain variable region or a humanized version thereof as defined by SEQ ID NO: 7 and/or a light chain variable region or a humanized version thereof as defined by SEQ ID NO: 5, In other embodiments, the antibody or antigen-binding fragment thereof comprises:
(i) a heavy chain variable region or a humanized version thereof, comprising at least one of the three CDRs as defined by SEQ ID NO: 16, SEQ ID NO: 17 or SEQ ID NO: 18, and
(ii) a light chain variable region comprising or a humanized version thereof, comprising at least one of the three CDRs as defined by SEQ ID NO: 19, SEQ ID NO: 20 or SEQ ID NO: 21.

In some embodiments, the heavy chain variable region or humanized version thereof comprises one of CDR1 (SEQ ID NO: 16), CDR2 (SEQ ID NO: 17) and CDR3 (SEQ ID NO: 18), and a light chain variable region or a humanized version thereof.

In some embodiments, the heavy chain variable region or humanized version thereof comprises one of CDR1 (SEQ ID NO: 16), CDR2 (SEQ ID NO: 17) and CDR3 (SEQ ID NO: 18), and a light chain variable region or a humanized version thereof, comprising at least one of CDR1 (SEQ ID NO: 19), CDR 2 (SEQ ID NO: 20) or CDR3 (SEQ ID NO: 21).

In some embodiments, the heavy chain variable region or humanized version thereof comprises one of CDR1 (SEQ ID NO: 16), CDR2 (SEQ ID NO: 17) and CDR3 (SEQ ID NO: 18), and a light chain variable region or a humanized version thereof, comprising at least two of CDR1 (SEQ ID NO: 19), CDR 2 (SEQ ID NO: 20) or CDR3 (SEQ ID NO: 21).

In some embodiments, the heavy chain variable region or humanized version thereof comprises one of CDR1 (SEQ ID NO: 16), CDR2 (SEQ ID NO: 17) and CDR3 (SEQ ID NO: 18), and a light chain variable region comprising or a humanized version thereof, comprising all of CDR1 (SEQ ID NO: 19), CDR 2 (SEQ ID NO: 20) or CDR3 (SEQ ID NO: 21).

In some embodiments, the heavy chain variable region or humanized version thereof comprises two of CDR1 (SEQ ID NO: 10), CDR2 (SEQ ID NO: 11) and CDR3 (SEQ ID NO: 12), and a light chain variable region or a humanized version thereof.

In some embodiments, the heavy chain variable region or humanized version thereof comprises two of CDR1 (SEQ ID NO: 16), CDR2 (SEQ ID NO: 17) and CDR3 (SEQ ID NO: 18), and a light chain variable region or a humanized version thereof, comprising at least one of CDR1 (SEQ ID NO: 19), CDR 2 (SEQ ID NO: 20) or CDR3 (SEQ ID NO: 21).

In some embodiments, the heavy chain variable region or humanized version thereof comprises two of CDR1 (SEQ ID NO: 16), CDR2 (SEQ ID NO: 17) and CDR3 (SEQ ID NO: 18), and a light chain variable region or a humanized version thereof, comprising at least two of CDR1 (SEQ ID NO: 19), CDR 2 (SEQ ID NO: 20) or CDR3 (SEQ ID NO: 21).

In some embodiments, the heavy chain variable region or humanized version thereof comprises two of CDR1 (SEQ ID NO: 16), CDR2 (SEQ ID NO: 17) and CDR3 (SEQ ID NO: 18), and a light chain variable region comprising or a humanized version thereof, comprising all of CDR1 (SEQ ID NO: 19), CDR 2 (SEQ ID NO: 20) and CDR3 (SEQ ID NO: 21).

In some embodiments, the heavy chain variable region or humanized version thereof comprises all of CDR1 (SEQ ID NO: 16), CDR2 (SEQ ID NO: 17) and CDR3 (SEQ ID NO: 18), and a light chain variable region or a humanized version thereof.

In some embodiments, the heavy chain variable region or humanized version thereof comprises all of CDR1 (SEQ ID NO: 16), CDR2 (SEQ ID NO: 17) and CDR3 (SEQ ID NO: 18), and a light chain variable region or a humanized version thereof, comprising at least one of CDR1 (SEQ ID NO: 19), CDR 2 (SEQ ID NO: 20) or CDR3 (SEQ ID NO: 21).

In some embodiments, the heavy chain variable region or humanized version thereof comprises all of CDR1 (SEQ ID NO: 16), CDR2 (SEQ ID NO: 17) and CDR3 (SEQ ID NO: 18), and a light chain variable region or a humanized version thereof, comprising at least two of CDR1 (SEQ ID NO: 19), CDR 2 (SEQ ID NO: 20) or CDR3 (SEQ ID NO: 21).

In some embodiments, the heavy chain variable region or humanized version thereof comprises all of CDR1 (SEQ ID NO: 16), CDR2 (SEQ ID NO: 17) and CDR3 (SEQ ID NO: 18), and a light chain variable region comprising or a humanized version thereof, comprising all of CDR1 (SEQ ID NO: 19), CDR 2 (SEQ ID NO: 20) and CDR3 (SEQ ID NO: 21).

In some embodiments, the antibody or antigen-binding fragment thereof comprises a heavy chain variable region or a humanized version thereof as defined by SEQ ID NO: 9 and/or a light chain variable region or a humanized version thereof as defined by SEQ ID NO: 3, In some embodiments the antibody or functional equivalent thereof is an antibody variant. Such variants include, but are not limited to, antibodies which have been modified in order to increase half-life, solubility and/or bioavailability. The functional equivalent may comprise a fragment of an antibody which is capable of binding to the HSPG binding site of PCSK9 (SEQ ID NO: 1). In some embodiments, the fragment is selected from the group consisting of Fab, Fab', F(ab')$_2$ and Fv fragments. Such variants may comprise engineered intradomain disulphide bonds.

The antibody or functional equivalent thereof may be obtained by domain shuffling. Domain shuffling can be performed by methods known in the art, such as by traditional cloning or by ligase-independent methods, e.g. uracil-specific excision reagent (USER) cloning and fusion (Nour-Eldin et al., 2010; Villiers et al., 2010).

In some embodiments, one or more Fv fragment of the antibody or functional equivalent thereof comprises a peptide linker between the V$_H$ and the V$_L$ domains.

LDLR and LDL-C Levels

Binding of the compound disclosed herein to PCSK9 results in reduced binding of PCSK9 to LDLR compared to the binding in the absence of said compound. This in turn results in increased levels of LDLR of cells derived from an LDLR-expressing cell line such as a hepatocyte-derived cell line, for example on their surface, compared to the levels in the absence of said compound. In some embodiments, the compound is an antibody and its binding to PCSK9 results in reduced binding of PCSK9 to LDLR compared to the binding in the absence of said antibody. This in turn results in increased levels of LDLR of cells derived from an LDLR-expressing cell line such as a hepatocyte-derived cell line compared to the levels in the absence of said antibody.

Thus in some embodiments, binding of the compound to PCSK9 results in increased levels of LDLR of cells derived from an LDLR-expressing cell line such as a hepatocyte-derived cell line compared to the levels in the absence of said compound. In specific embodiments, the compound is an antibody as defined above and binding of the antibody to PCSK9 results in increased levels of LDLR of cells derived from an LDLR-expressing cell line such as a hepatocyte-derived cell line compared to the levels in the absence of said antibody.

In some embodiments, binding of the compound to PCSK9 results in decreased lysosomal degradation of LDLR compared to the degradation in the absence of said compound. In specific embodiments, the compound is an antibody as defined above and binding of the antibody to PCSK9 results in decreased lysosomal degradation of LDLR compared to the degradation in the absence of said antibody.

In some embodiments, binding of the compound to PCSK9 results in decreased plasma levels of LDL-C compared to the levels in the absence of said compound. The term 'plasma LDL-C levels' shall be understood to refer to the levels of LDL-C in the plasma, i.e. the amount of LDL-C protein. In specific embodiments, the compound is an antibody as defined above and binding of the antibody to PCSK9 results in decreased plasma levels of LDL-C compared to the levels in the absence of said antibody.

The plasma levels of LDL-C can be determined in vivo or in vitro. Methods to determine plasma levels of LDL-C are known in the art and include, but are not limited to Western Blot, immuno-staining, ELISA, ultracentrifugation, fast protein liquid chromatography (FPLC) and electrophoresis methods.

The compound disclosed herein may be an antibody stable in serum.

Also provided herein is a compound as defined above which is non-toxic, in particular after administration. In some embodiments, the compound is an antibody which is non-toxic after administration.

In some embodiments, the compound is administered in combination with another compound, such as an anti-PCSK9 antibody, such as an antibody binding to the LDLR-binding site of PCSK9, or a statin. In some embodiments, the compound is administered together with an antibody selected from the group consisting of: lodelcizumab, ralpancizumab, alirocumab, evolocumab and bococizumab.

Accordingly, is provided herein a method for reducing plasma LDL-C levels in a subject in need thereof, said method comprising the step of administering to said subject a compound or a pharmaceutical composition as defined herein. Plasma LDL-C levels can be determined in vivo or in vitro by any method known in the art, as described above.

Heparin Analogues and Heparin Mimetics

In some embodiments, the compound capable of inhibiting binding of HSPGs to PCSK9 is a heparin analogue or a heparin mimetic. See e.g. R. Lever et al. (eds.), Heparin—A Century of Progress, Handbook of Experimental Pharmacology 207, Springer-Verlag Berlin Heidelberg 2012, herein incorporated by reference.

The heparin analogue or heparin mimetic may be a competitive antagonist, an uncompetitive antagonist, a non-competitive antagonist, a silent antagonist, a partial agonist or an inverse agonist of HSPGs.

In some embodiments, the compound is heparin. In other embodiments, the heparin analogue or heparin mimetic is a peptide.

In some embodiments, the heparin analogue or heparin mimetic is capable of inhibiting binding of heparin to PCSK9. The heparin analogue or heparin mimetic may bind to any of the amino acid residues of PCSK9 as described herein above.

The compound, the heparin analogue or the heparin mimetic may have a general structure of formula (I):

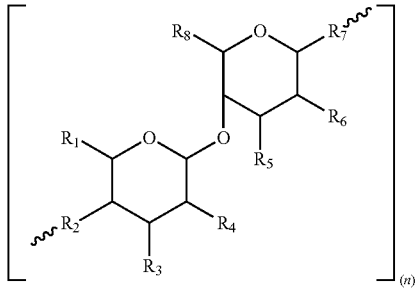

wherein:
R₁ is selected from the group consisting of COOH and ⁻O₃SO,
R₂, R₃, R₅ and R₇ are selected from the group consisting of O and OH
R₄ is selected from the group consisting of a sulfate group,
R₆ is selected from the group consisting of a sulphamate group, OH and O,
R₈ is selected from the group consisting of a sulfate group,
n is an integer equal or greater than 1,
and wherein R₂ and/or R₇ optionally can act as linkers linking monomer units.

In one embodiment, the heparin analogue or mimetic is
a) Fondaparinux (Arixtra™) and has the formula:

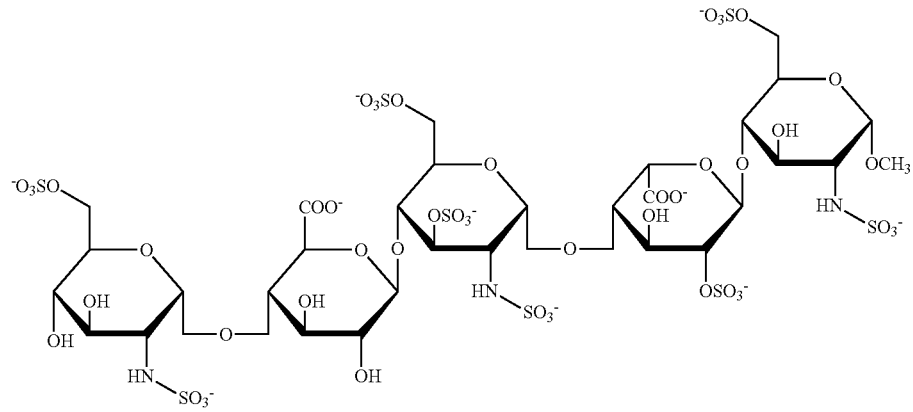

b) a low molecular weight heparin such as dalteparin sodium or tinzaparin sodium; and
c) a compound of formula (II):

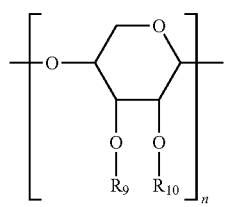

wherein R₉ and R₁₀ are independently selected from the group consisting of H, COOH, ⁻O₃SO, O, OH, sulfate and sulfamate, and wherein n is an integer equal to or greater than 1.

In one embodiment, the compound of formula (II) is pentosan and has the formula:

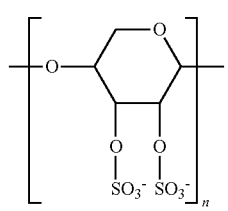

where n is an integer equal to or greater than 1.

In one embodiment, the compound is a low molecular weight heparin. In a specific embodiment, the low molecular weight heparin is dalteparin sodium (trade name fragmin). In another embodiment, the low molecular weight heparin is tinzaparin sodium (trade name Innohep™).

In yet another embodiment, the compound is a compound of formula (II):

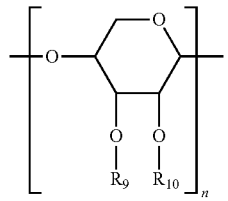

wherein $R_9$ and $R_{10}$ are independently selected from the group consisting of H, COOH, $^-O_3SO$, O, OH, sulfate and sulfamate, and wherein n is an integer equal to or greater than 1.

In one embodiment, the compound of formula (II) is pentosan and has the formula:

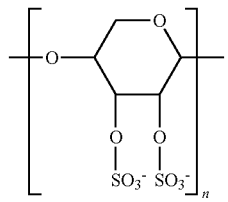

where n is an integer equal to or greater than 1.
In some embodiments, the compound is suramin. Suramin has the formula:

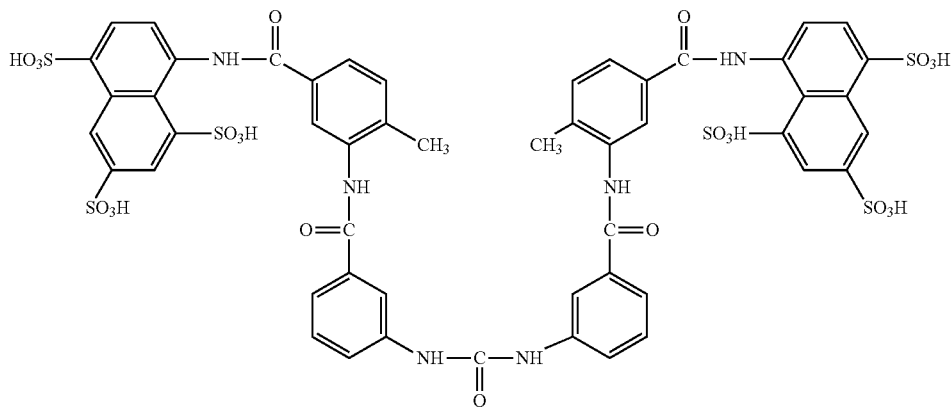 [SMILES: Cc1ccc(C(=O)Nc2ccc(S(=O)(=O)O)c3cc(S(=O)(=O)O)cc(S(=O)(=O)O)c23)cc1NC(=O)c1cccc(NC(=O)Nc2cccc(C(=O)Nc3cc(C(=O)Nc4ccc(S(=O)(=O)O)c5cc(S(=O)(=O)O)cc(S(=O)(=O)O)c45)ccc3C)c2)c1]

In a specific embodiment, the compound is a compound of formula (III):

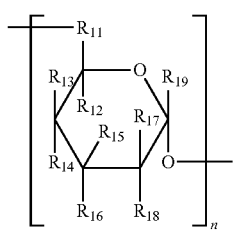

wherein $R_{11}$, $R_{12}$, $R_{13}$, $R_{14}$, $R_{15}$, $R_{16}$, $R_{17}$, $R_{18}$, and $R_{19}$ are independently selected from the group consisting of COOH, $^-O_3SO$, O, OH, sulfate and sulfamate, and n is an integer equal to or greater than 1, and wherein $R_{14}$ optionally can act as linkers linking monomer units.

In one embodiment, the compound of formula (III) is dextran sulphate and has the formula:

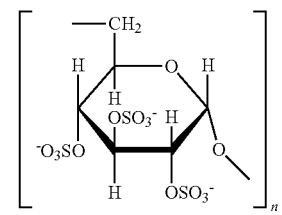

where n is an integer equal to or greater than 1.

In another embodiment, the compound is a phosphorothioate oligonucleotide S-dNn, where N is any nucleotide and where n is the number of phosphorothioate linkages in said phosphorothioate oligonucleotide. Phosphorothioate oligonucleotides are known to act as heparin mimetics and bind to heparin binding proteins such as bFGF (Benimetskaya et al., 1995). Their polyanonic backbone makes them resemble heparin, dextran sulphate and pentosan. In some embodiments, the phosphorothioate oligonucleotide is S-dCn. In other embodiments, the phosphorothioate oligonucleotide is S-dAn. In other embodiments, the phosphorothioate oligonucleotide is S-dGn. In other embodiments, the phosphorothioate oligonucleotide is S-DTn. In other embodiments, any nucleotide of the phosphorothioate oligonucleotide is chosen independently from the others from the group consisting of A, T, G and C.

The general structure of an S-dCn, where n is an integer nucleotide is represented in the below formula:

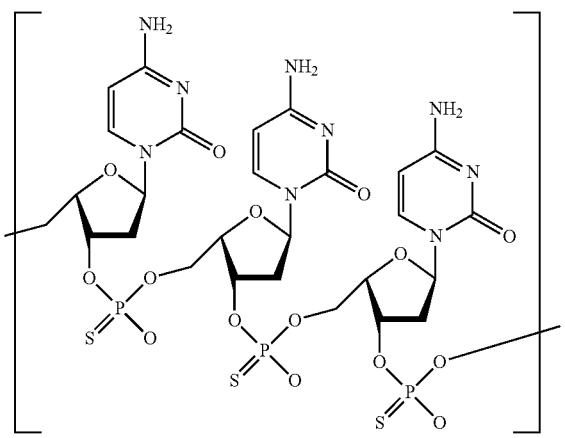

Preferably, n is between 12 and 60. Thus in some embodiments, n is between 15 and 55, such as between 20 and 50, such as between 25 and 45, such as between 30 and 40, such as 36.

Normally, S-oligonucleotides are designed so that their sequence is complementary to a target mRNA, and thus specifically induce said target mRNA's degradation. Without being bound by theory, the inventors believe that the important mechanism for phosphothioate oligonucleotides in the context of the present disclosure is their ability to bind non-specifically to a variety of proteins (see e.g. Yabukov et al., 1993; Stein et al. 1995). Accordingly, in some embodiments, the phosphorothioate oligonucleotides have no or little antisense activity; instead, they bind nucleotide sequence independent to any of the amino acid residues of PCSK9 as described herein. The skilled person knows how to optimise the design of S-oligonucleotides to obtain such phosphorothioate oligonucleotides having a nucleotide sequence that do not exhibit antisense activity.

While the length of the oligonucleotide and in particular the number of phosphorothioate linkages influences the heparin mimetic activity of phosphorothioate oligonucleotides, it appears that the nucleotide sequence within the S-oligonucleotides has essentially no influence on the heparin mimetic activity. Accordingly, any sequence can be used as long as the length of and the number of phosphorothioate bonds in the S-oligonucleotides have been optimised as is routine in the art.

Methods for synthesising phosphorothioate oligonucleotides are known in the art. As non-limiting examples, one method involves the action of a solution of elemental sulfur in carbon disulfide on a hydrogen phosphonate, while another involves sulfurizing phosphite triesters with either tetraethylthiuram disulfide (TETD) or 3H-1,2-bensodithiol-3-one 1,1-dioxide (BDTD).

A phosphorothioate linkage is inherently chiral. The sulfurization methods give a mixture of isomers at each incorporation site, resulting in 2n−1 isomers for an oligo of length n. Without being bound by theory, the isomer mix in any standard S-oligonucleotide preparation does not appear to affect the biological activity of the oligonucleotides. In one embodiment, the S-oligonucleotides are an isomer mix. In another embodiment, the S-oligonucleotides are provided as one isomeric form.

For oligonucleotides to resist degradation, phosphorothioate linkages do not have to be present throughout the oligonucleotide. The person skilled in the art knows how the number of phosphorothioate linkages can be adjusted.

Disorders of Lipoprotein Metabolism

Herein is also provided a compound as defined above for use as a medicament.

The compound disclosed herein is useful for treating a disorder of lipoprotein metabolism. Accordingly is also provided herein a use of the compound as defined herein for the preparation of a medicament for the treatment of a disorder of lipoprotein metabolism. There is also disclosed the compound as defined above for use in a method of treatment of a disorder of lipoprotein metabolism in a subject in need thereof. The sequence of PCSK9 may vary from one subject to another, e.g. individual-specific SNPs that may lead to conservative substitutions may be found in some individuals. It will be understood that compounds inhibiting binding of HSPGs to such PCSK9 variants are also within the scope of the invention.

Disorders of lipoprotein metabolism are disorders of lipid homeostasis and disorders associated therewith and include by way of example hypercholesterolemia, hyperlipidemia, hypertriglyceridaemia, sitosterolemia, atherosclerosis, arteriosclerosis, coronary heart disease, metabolic syndrome, acute coronary syndrome, xanthoma, hypertension, angina, obesity, diabetes and vascular inflammation. Such disorders can be caused for example by defects in the structural proteins of lipoprotein particles, in the cell receptors that recognize the various types of lipoproteins, or in the enzymes that break down fats. As a result of such defects, lipids may become deposited in the walls of blood vessels.

Hypercholesterolemia (or dyslipidemia) is the presence of high levels of cholesterol in the blood. It is a form of hyperlipidemia (elevated levels of lipids in the blood) and hyperlipoproteinemia (elevated levels of lipoproteins in the blood).

Hypertriglyceridemia denotes high blood levels of triglycerides. Elevated levels of triglycerides are associated with atherosclerosis, even in the absence of hypercholesterolemia, and predispose to cardiovascular disease. Very high triglyceride levels also increase the risk of acute pancreatitis.

Sitosterolemia or phytosterolemia is a rare autosomal recessively inherited lipid metabolic disorder characterized by hyperabsorption and decreased biliary excretion of dietary sterols leading to e.g. hypercholesterolemia, tendon and tuberous xanthomas, premature development of atherosclerosis.

Atherosclerosis (also known as arteriosclerotic vascular disease or ASVD) is a specific form of arteriosclerosis in which an artery wall thickens as a result of invasion and accumulation of white blood cells, containing both living, active white blood cells (producing inflammation) and remnants of dead cells, including cholesterol and triglycerides. Atherosclerosis is therefore a syndrome affecting arterial blood vessels due to a chronic inflammatory response of white blood cells in the walls of arteries.

Arteriosclerosis is a condition involving thickening, hardening and loss of elasticity of the walls of arteries.

Coronary heart disease, also known as atherosclerotic artery disease, atherosclerotic cardiovascular disease, coronary heart disease or ischemic heart disease, is the most common type of heart disease and cause of heart attacks. The disease is caused by plaque building up along the inner walls of the arteries of the heart, which narrows the lumen of arteries and reduces blood flow to the heart.

Metabolic syndrome is a disorder of energy utilization and storage, diagnosed by a co-occurrence of three out of five of the following medical conditions: abdominal (central) obesity, elevated blood pressure, elevated fasting plasma glucose, high serum triglycerides, and low high-density cholesterol levels. Metabolic syndrome increases the risk of developing cardiovascular disease, particularly heart failure, and diabetes. Metabolic syndrome is also known as metabolic syndrome X, cardiometabolic syndrome, syndrome X, insulin resistance syndrome, Reaven's syndrome, and CHAOS (in Australia). Metabolic syndrome and pre-diabetes appear to be the same disorder, just diagnosed by a different set of biomarkers.

Acute coronary syndrome refers to a group of conditions due to decreased blood flow in the coronary arteries such that part of the heart muscle is unable to function properly or dies.

A xanthoma is a cutaneous manifestations of lipidosis in which lipids accumulate in large foam cells within the skin. Xanthomas are associated with hyperlipidemias.

Hypertension or high blood pressure, sometimes called arterial hypertension, is a chronic medical condition in which the blood pressure in the arteries is elevated.

Angina pectoris (or angina) refers to a sensation of chest pain, pressure, or squeezing, often due to ischemia of the heart muscle from obstruction or spasm of the coronary arteries. While angina pectoris can derive from anemia, cardiac arrhythmias and heart failure, its main cause is coronary artery disease.

Obesity is a medical condition in which excess body fat has accumulated to the extent that it may have a negative effect on health, leading to reduced life expectancy and/or increased health problems, such as increased risk of heart disease, type 2 diabetes, obstructive sleep apnea, certain types of cancer, and osteoarthritis.

Diabetes mellitus, commonly referred to as diabetes, is a group of metabolic diseases in which there are high blood sugar levels over a prolonged period. Several types of diabetes exist, including type I diabetes, type II diabetes and gestational diabetes. Type 1 diabetes is characterized by loss of the insulin-producing beta cells of the islets of Langerhans in the pancreas, leading to insulin deficiency. Type 2 diabetes is characterized by insulin resistance, which may be combined with relatively reduced insulin secretion. The defective responsiveness of body tissues to insulin is believed to involve the insulin receptor. Gestational diabetes, which resembles type 2 diabetes, occurs in about 2-10% of all pregnancies.

In some embodiments, the disorder of lipoprotein metabolism is linked to abnormal PCSK9 plasma levels. In other embodiments, the disorder of lipoprotein metabolism is linked to abnormal LDLR levels at the surface of LDLR-expressing cells such as hepatocytes. The disorder of lipoprotein metabolism can also be linked to abnormal PCSK9 plasma levels and abnormal LDLR levels at the surface of LDLR-expressing cells such as hepatocytes. PCSK9 plasma levels vary in humans from 30 to 3000 ng/ml. Abnormal PCSK9 plasma levels refer to plasma levels of PCSK9 which are significantly different from the average levels in a healthy individual. In some embodiments, the abnormal PCSK9 plasma level is significantly higher than the average level in a healthy individual. Likewise, abnormal LDLR levels at the surface of e.g. hepatocytes refer to LDLR levels which are significantly different from the average levels in a healthy individual. In some embodiments, the abnormal LDLR level at the surface of LDLR-expressing cells such as hepatocytes is significantly lower than the average level in a healthy individual.

In some embodiments, the disorder is characterized by abnormal levels of LDL-C, in particular by elevated levels of LDL-C.

Treatment of a Lipoprotein Metabolism Disorder

An individual or a subject in need of treatment of a disorder of lipoprotein metabolism is an individual suffering from, suspected of suffering from or at risk of suffering from a disorder of lipoprotein metabolism. In some embodiments, the individual in need of treatment is a mammal, preferably a human.

In preferred embodiments, the disorder of lipoprotein metabolism is selected from the group consisting of dyslipidemia, hypercholesterolemia and coronary heart diseases. In a preferred embodiment, the disorder of lipoprotein metabolism is coronary heart diseases.

In some embodiments, the treatment is prophylactic.

In some embodiments, the treatment comprises a step of administering to said subject a compound as disclosed herein. The compound can be administered at a daily dosage of between 0.1 mg and 1000 mg per kg bodyweight. Thus in some embodiments, the compound is administered at a daily dosage of between 0.1 mg and 1000 mg per kg bodyweight, such as between 0.2 and 900 mg per kg bodyweight, such as between 0.3 and 800 mg per kg bodyweight, such as between 0.5 and 700 mg per kg bodyweight, such as between 1.0 and 500 mg per kg bodyweight, such as between 5 and 400 mg per kg bodyweight, such as between 10 and 300 mg per kg bodyweight, such as between 25 and 250 mg per kg bodyweight, such as between 50 and 200 mg per kg bodyweight, such as between 75 and 150 mg per kg bodyweight, such as between 100 and 125 mg per kg bodyweight. In some embodiments, the compound is administered at a daily dosage of between 0.1 mg and 1000 mg per kg bodyweight, such as between 0.1 and 10 mg per kg bodyweight, such as between 10 and 25 mg per kg bodyweight, such as between 25 and 50 mg per kg bodyweight, such as between 50 and 100 mg per kg bodyweight, such as between 100 and 250 mg per kg bodyweight, such as between 250 and 500 mg per kg bodyweight, such as between 500 and 750 mg per kg bodyweight, such as between 750 and 1000 mg per kg bodyweight.

Also disclosed herein is a method of treatment of a disorder of lipoprotein metabolism selected from the group consisting of dyslipidemia, hypercholesterolemia and heart coronary diseases in an individual in need thereof, the method comprising the steps of:
  i. providing a tissue sample or a plasma sample isolated from said individual,
  ii. determining the levels of LDLR in said tissue and/or the levels of PCSK9 and/or the levels of LDL-C in said plasma sample,
  iii. correlating the expression level of step ii) with the levels of a control tissue sample or a control plasma sample,
  iv. assessing a treatment regime,
  v. administering to the individual a composition comprising a therapeutically effective amount of a compound as disclosed herein.

In some embodiments, the method comprises the steps of:
  i. providing a tissue sample isolated from said individual,
  ii. determining the levels of LDLR of said tissue,
  iii. correlating the expression level of step ii) with the levels of a control tissue sample,
  iv. assessing a treatment regime, v. administering to the individual a composition comprising a therapeutically effective amount of a compound as disclosed herein.

Thus in some embodiments, a composition comprising a therapeutically effective amount of a compound as disclosed herein is administered to the individual if the levels of LDLR at the surface of the cells of said tissue are abnormal. In some embodiments, abnormal levels of LDLR are reduced levels of LDLR. In some embodiments, the tissue sample comprises LDLR-expressing cells such as hepatocytes and the levels of LDLR at the surface of said cells are measured.

In other embodiments, the method comprises the steps of:
i. providing a plasma sample isolated from said individual,
ii. determining the levels of PCSK9 and/or the levels of LDL-C in said plasma sample,
iii. correlating the expression level of step ii) with the levels of a control plasma sample,
iv. assessing a treatment regime,
v. administering to the individual a composition comprising a therapeutically effective amount of a compound as disclosed herein.

Thus in some embodiments, a therapeutically effective amount of a composition comprising a compound as disclosed herein is administered to the individual if the levels of LDL-C and/or the levels of PCSK9 in the plasma sample are abnormal. In some embodiments, abnormal levels of LDL-C are increased levels of LDL-C. In some embodiments, the tissue sample comprises LDLR-expressing cells such as hepatocytes and the levels of LDLR at the surface of said cells are measured.

Also disclosed herein is a method of inhibiting degradation of LDLR, said method comprising administering a compound as defined herein. In particular, the compound may be a compound of general formula (I) as defined herein above.

In some embodiments, the compound is a heparin analogue or mimetic such as Fondaparinux. In another embodiment, the compound is pentosan. In yet another embodiment, the compound is suramin. In yet another embodiment, the compound is dextran sulphate. In yet another embodiment, the compound is a low molecular weight heparin such as dalteparin sodium or tinzaparin sodium. In yet another embodiment, the compound is a phosphorothioate oligonucleotide as defined herein above.

Pharmaceutical Composition

Also disclosed herein is a pharmaceutical composition comprising at least one compound as defined herein. In some embodiments, the composition comprises one compound as disclosed herein. In other embodiments, the composition comprises two compounds or more, such as three compounds or more, such as four compounds or more, such as five compounds or more.

In some embodiments, the composition further comprises at least one of:
an antibody inhibiting binding of PCSK9 to LDLR;
a statin;
cholestyramine
a cholesterol absorption inhibitor e.g. ezetimibe.

Thus in some embodiments, the pharmaceutical composition comprises at least one compound as defined herein and at least one additional compound selected from the group consisting of an antibody inhibiting binding of PCSK9 to LDLR, a statin or cholestyramine. In one embodiment, the pharmaceutical composition comprises one compound as defined herein and an antibody inhibiting binding of PCSK9 to LDLR. In one embodiment, the pharmaceutical composition comprises one compound as defined herein and a statin. In one embodiment, the pharmaceutical composition comprises one compound as defined herein and cholestyramine. In one embodiment, the pharmaceutical composition comprises one compound as defined herein, an antibody inhibiting binding of PCSK9 to LDLR and a statin. In one embodiment, the pharmaceutical composition comprises one compound as defined herein, an antibody inhibiting binding of PCSK9 to LDLR and cholestyramine. In one embodiment, the pharmaceutical composition comprises one compound as defined herein, cholestyramine and a statin. In one embodiment, the pharmaceutical composition comprises one compound as defined herein, an antibody inhibiting binding of PCSK9 to LDLR, a statin and cholestyramine.

The pharmaceutical composition may optionally comprise one or more pharmaceutically acceptable carriers excipients, and may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications. Typically, the pharmaceutical compositions of the present invention may be formulated for parenteral administration e.g., by intravenous or subcutaneous injection, and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. The compositions may be suitable for oral ingestion. This is particularly relevant for small molecule compositions. Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water. Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. The parenteral formulations typically will contain from about 0.0001 to about 25%, such as from about 0.5 to about 25%, by weight of the active ingredient in solution. Preservatives and buffers may be used. In order to minimise or eliminate irritation at the site of injection, such compositions may contain one or more nonionic surfactants having a hydrophile-lipophile balance (HLB) of from about 12 to about 17. The quantity of surfactant in such formulations will typically range from about 0.000001 to about 15% by weight, such as from about 0.000001 to about 5% by weight or from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

The main route of drug delivery according to this invention is however parenteral in order to introduce the agent into the blood stream to ultimately target the relevant tissue.

The agent may also be administered to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth.

In a preferred embodiment the agent of the invention is administered parenterally, that is by intravenous, intramuscular, intraspinal, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

In one embodiment the pharmaceutical composition according to the present invention is formulated for parenteral administration such as by injection.

In a further embodiment the pharmaceutical composition according to the present invention is formulated for intravenous, intramuscular, intraspinal, intraperitoneal, subcutaneous, a bolus or a continuous administration.

The rate and frequency of the administration may be determined by the physician from a case to case basis. In one embodiment the administration occurs at intervals of 30 minutes to 24 hours, such as at intervals of 1 to 6 hours, such as once daily.

The duration of the treatment may vary depending on severity of the disorder. In one embodiment the duration of the treatment is from 1 day to 28 days, such as from 2 days to 25 days, such as from 5 days to 20 days, such as from 7 days to 15 days. In chronic cases the duration of the treatment may be lifelong.

The dosage can be determined by the physician in charge based on the characteristics of the patient and the means and mode of administration. In one embodiment of the present invention, the dosage of the active compound of the pharmaceutical composition as defined herein above, is between 0.1 mg and 1000 mg per kg bodyweight.

The dosage may be administered as a bolus administration or as a continuous administration. In relation to bolus administration the pharmaceutical composition may be administered at intervals of 30 minutes to 24 hours, such as once daily.

In some embodiments, the pH of the composition is between pH 4 and pH 10.

In some embodiments, the composition is formulated for oral administration.

In some embodiments, the composition is formulated for parenteral administration. In specific embodiments, the parenteral administration is by injection. Such parenteral administration may be intravenous, intramuscular, intraspinal, intraperitoneal, subcutaneous, a bolus or a continuous administration.

Method of Selecting an Antibody

Also disclosed herein is a method of selecting an antibody specifically recognising and binding an epitope within the HSPG binding site of PCSK9 (SEQ ID NO: 1), said method comprising the steps of:

i. administering to a mammal a polypeptide fragment of PCSK9 or a polynucleotide encoding a polypeptide fragment of PCSK9 comprising at least one amino acid residue of the domain consisting of amino acid residues 78 to 167 of SEQ ID NO: 1, such as at least 5, such as at least 10, such as at least 15, such as at least 20, such as at least 25, such as at least 30, such as at least 35, such as at least 40, such as at least 45, such as at least 50, such as at least 55, such as at least 60, such as at least 65, such as at least 70, such as at least 75, such as at least 80, such as at least all amino acids of the domain consisting of amino acid residues 78 to 167 of SEQ ID NO: 1;

ii. identifying and selecting antibodies recognising said polypeptide, and iii. determining whether said selected antibodies are capable of displacing one or more reference antibodies in a competitive ELISA assay.

Methods for administering the polypeptide fragment of PCSK9 or the polynucleotide encoding a polypeptide fragment of PCSK9 are known in the art and include immunisation of the mammal or phage display.

In some embodiments, the method further comprises a step of selecting antibodies capable of displacing at least one of said reference antibodies. The reference antibodies are antibodies capable of binding to PCSK9 or a fragment thereof.

The step of determining whether said selected antibodies are capable of displacing one or more reference antibodies in a competitive ELISA comprises the steps of:

i. providing PCSK9 or a fragment thereof comprising the epitope recognised by said reference antibody; and ii. adding a test antibody and said reference antibody to said PCSK9 or fragment thereof, wherein either the test antibody or the reference antibody is labelled with a detectable label or both antibodies are labelled with different detectable labels; and iii. detecting the presence of the detectable label at PCSK9;

thereby detecting whether the test antibody is capable of displacing the reference antibody.

The method may further comprise testing the antibodies to determine whether they are capable of inhibiting LDLR degradation and selecting antibodies capable of inhibiting LDLR degradation.

Also disclosed herein is a method of selecting a peptide or a heparin analogue or mimetic capable of inhibiting binding of HSPGs such as heparin to PCSK9, said method comprising the steps of:

i. providing a plurality of peptides or heparin analogues or mimetics;

ii. incubating said plurality of peptides or heparin analogues or mimetics with cells derived from an LDLR-expressing cell line such as a hepatocyte-derived cell line in a medium;

iii. determining the levels of PCSK9 in said medium and/or the levels of LDLR of said cells;

iv. selecting the peptides or heparin analogues or mimetics resulting in the highest levels of PCSK9 and/or LDLR as determined in step iii.

In some embodiments, the levels of PCSK9 are the levels of PCSK9 detached from the cell surface.

Compounds Capable of Binding the Compounds Disclosed Herein

Also disclosed herein are compounds capable of selectively binding the compound as defined above. In some embodiments, the compound capable of selectively binding the compound as defined above is an antibody.

Method for Producing the Antibody Disclosed Herein

A method for producing the antibody as defined herein, said method comprising the steps of:
i. administering to a mammal a protein or a polynucleotide encoding a protein comprising the HSPG binding domain of PCSK9 or a fragment thereof or a functional equivalent thereof;
ii. selecting said antibody if it is able to bind to PCSK9 (SEQ ID NO: 1);
iii. selecting said antibody if it is unable to bind to mutated PCSK9, wherein said mutated PCSK9 is unable to bind to HSPG.

Methods for administering the protein or a polynucleotide encoding a protein comprising the HSPG binding domain of PCSK9 or a fragment thereof or a functional equivalent thereof are known in the art and include immunisation of the mammal or phage display.

In some embodiments, said mutated PCSK9 is mutated at least at one of positions 93, 96, 97, 104, 105, 136, 139, 165 or 167. In some embodiments, the mutations are alanine substitutions. In some embodiments, two or more of the amino acid residues at positions 93, 96, 97, 104, 105, 136, 139, 165 or 167 are mutated.

In specific embodiments, the mutated PCSK9 is selected from the group consisting of mutants R93A, R96A, R97A, R104A, R105A, K136A, H139A, R165A or R167A, where the positions are the positions of PCSK9 as set forth in SEQ ID NO: 1. In one particular embodiment, the mutated PCSK9 is mutated at positions R93, R96, R97, R104, R105 and H139 of PCSK9. Preferably, the mutations are mutations to alanine.

In some embodiments, the mammal to which a protein comprising the HSPG binding domain of PCSK9 or a fragment thereof or a functional equivalent thereof is administered is a rodent, such as a mouse, a rat, a hamster or a guinea pig.

The method may further comprise isolating antibody producing cells from said mammal, preparing hybridoma cells from said antibody producing cells, cultivating said hybridomas and isolating antibodies produced by said hybridomas. Methods to isolate antibodies from hybridoma cells are known in the art.

In some embodiments, the method is for producing an antibody as disclosed herein, and comprises the steps of transfecting a host cell with a nucleic acid construct encoding said antibody. The antibody may be produced by a recombinant cell. Suitable recombinant cells can be microorganisms selected from the group comprising bacteria and eukaryotic microorganisms.

In some embodiments, the microorganism is a bacterium selected from the group comprising *Escherichia coli, Lactobacillus zeae, Bacillus subtilis, Streptomyces lividans, Staphylococcus carnosus, Bacillus megaterium* and *Corynebacterium glutamicum*.

In other embodiments, the microorganism is a eukaryotic microorganism selected from the group comprising *Saccharomyces cerevisiae, Aspergillus niger, Pichia pastoris, Schizosaccharomyces pombe, Yarrowia lipolytica* and *Kluyveromyces lactis*.

The host cell can also be selected from the group comprising plant cells and animal cells. In some embodiments, the host cells is a plant cell selected from the group comprising *Arabidopsis* sp., pea, rice, maize, tobacco, barley, or seeds thereof. In other embodiments, the host cell is an animal cell derived from a mammal selected from the group comprising Chinese Hamster Ovary, mouse and human. In other embodiments, the animal cell is derived from an insect or an avian cell line.

The method may also comprise the steps of identifying and selecting the antibody.

EXAMPLES

Example 1: Mapping of the HSPG Binding Site in PCSK9

Figure 1:
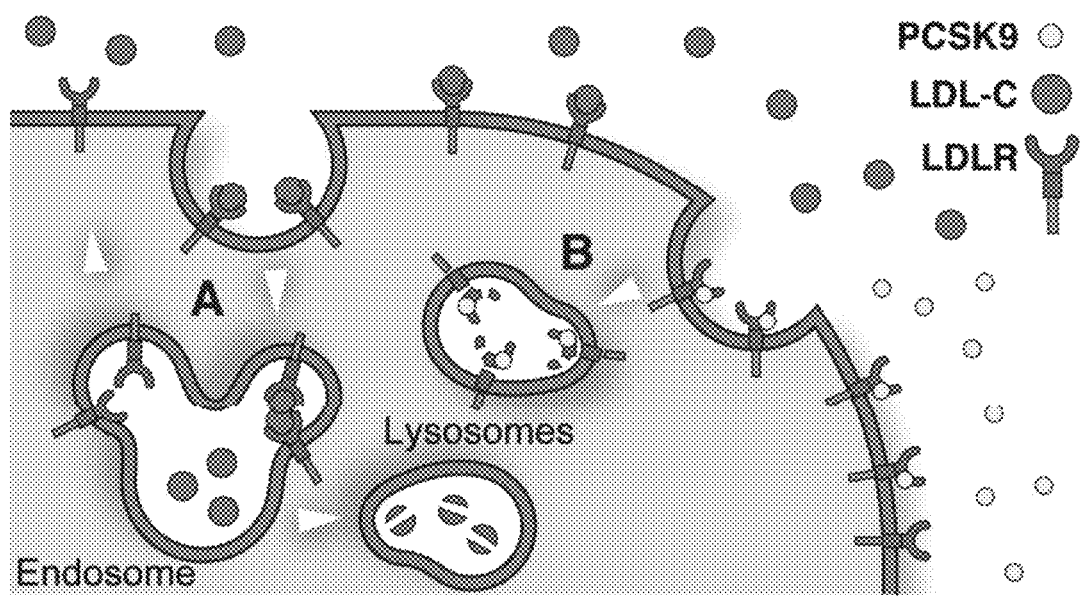
FIG. 1: A drawing of the current model as described in the literature showing that the LDLR takes up cholesterol-bearing LDL-C particles from the circulation and delivers them to lysosomes for degradation, while the receptor (LDLR) is recycled to the cell surface after release of cargo in endosomes (A). Upon binding to PCSK9 the LDLR itself is degraded in lysosomes (B). Accordingly high activity of PCSK9 results in decreased levels of LDLR at the cell surface and increased plasma cholesterol, whereas inhibition of PCSK9 activity reduces plasma cholesterol levels and slows the progression of coronary artery disease.
Figure 2:
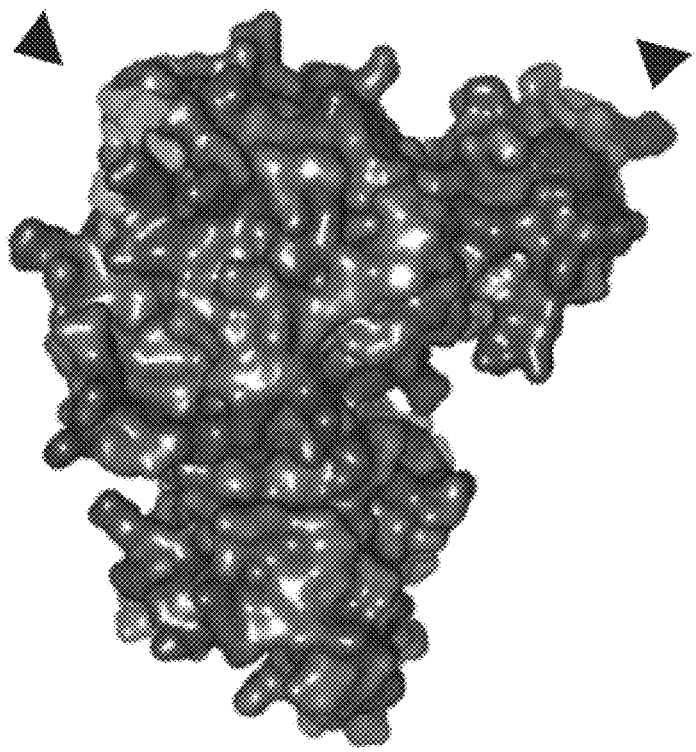
FIG. 2: (A) Shown is a spacefilling model of PCSK9 with the LDLR binding site and the HSPG binding sites indicated by the left and right arrowheads, respectively. (B) A heparin pentasaccharide (SANORG, sticks) at the electrostatic surface (red negative; blue positive) of the predicted HSPG binding site in PCSK9 (PDB ID: 2PMW) (Piper et al., 2007) with positively charged amino acids (R: arginine, H: histidine) indicated. (C) Superposition of SANORG onto the HSPG binding site in PCSK9 (ribbon). (D) Non-permeabilized HepG2 cells expressing PCSK9 (white) after treatment with or without heparinase I. Nuclei were stained with Hoechst (dark grey). (E) PCSK9 binding to heparin was analyzed by heparin affinity chromatography. PCSK9 was eluted from the column at a NaCl concentration of 500 mM.
Figure 2:
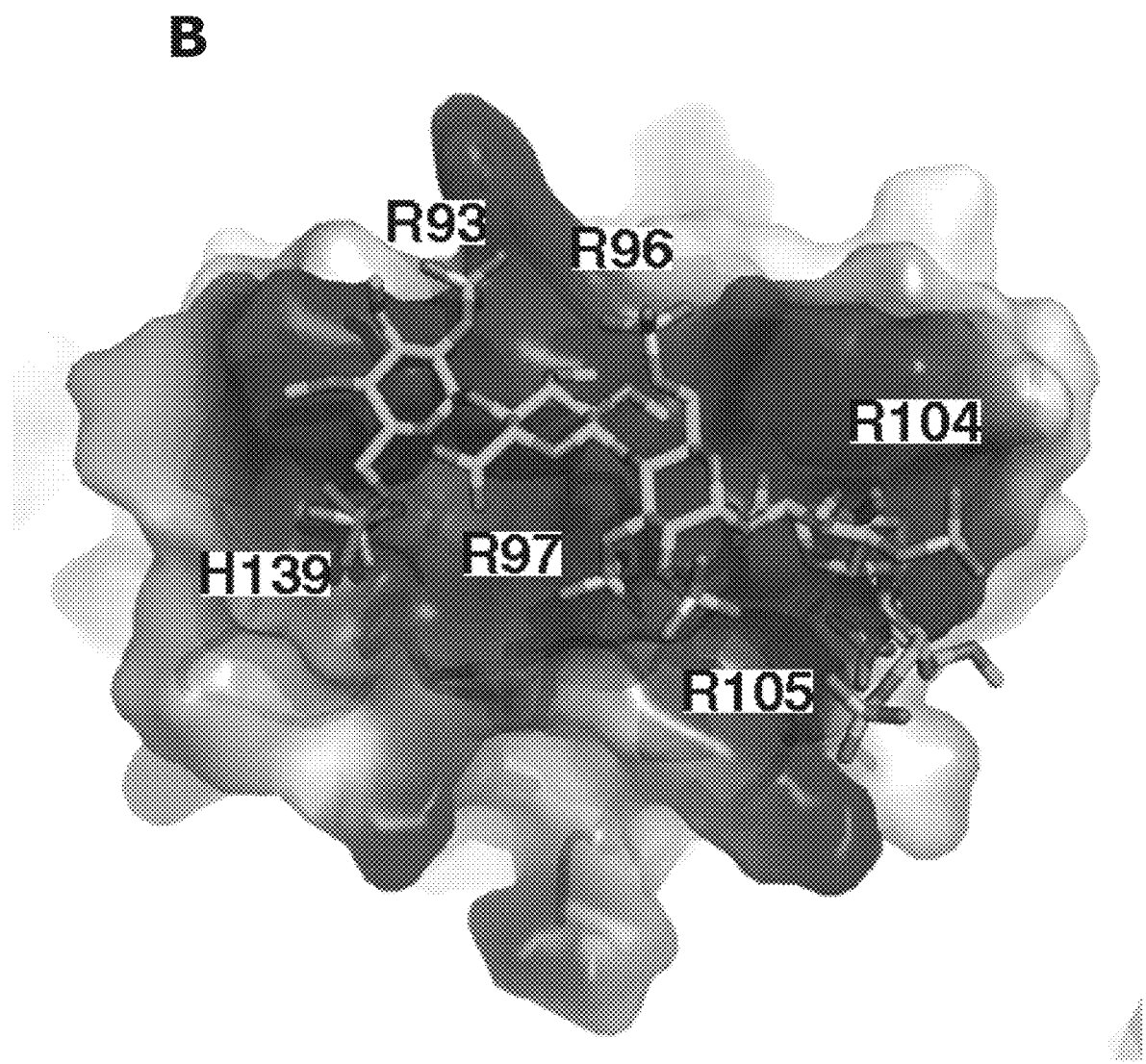
Figure 2:
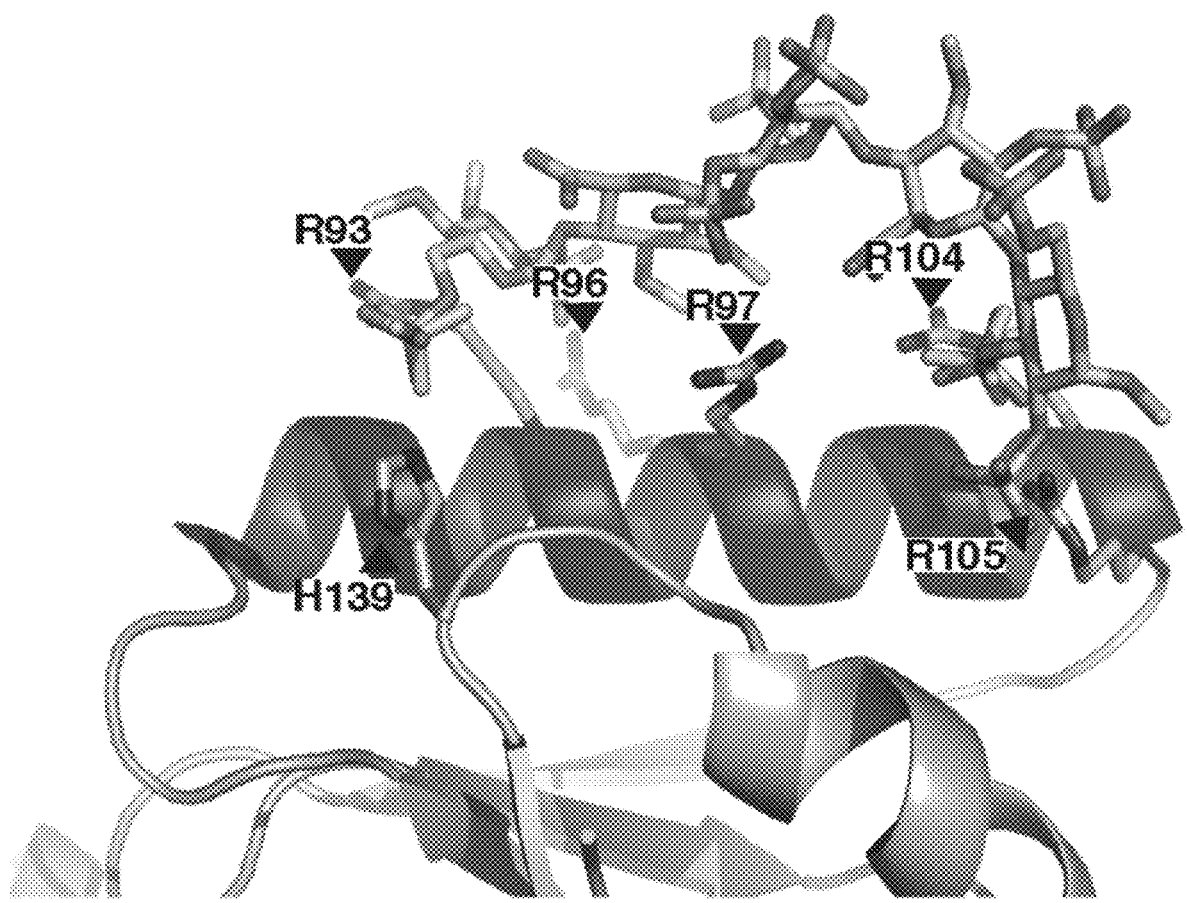
Figure 2:
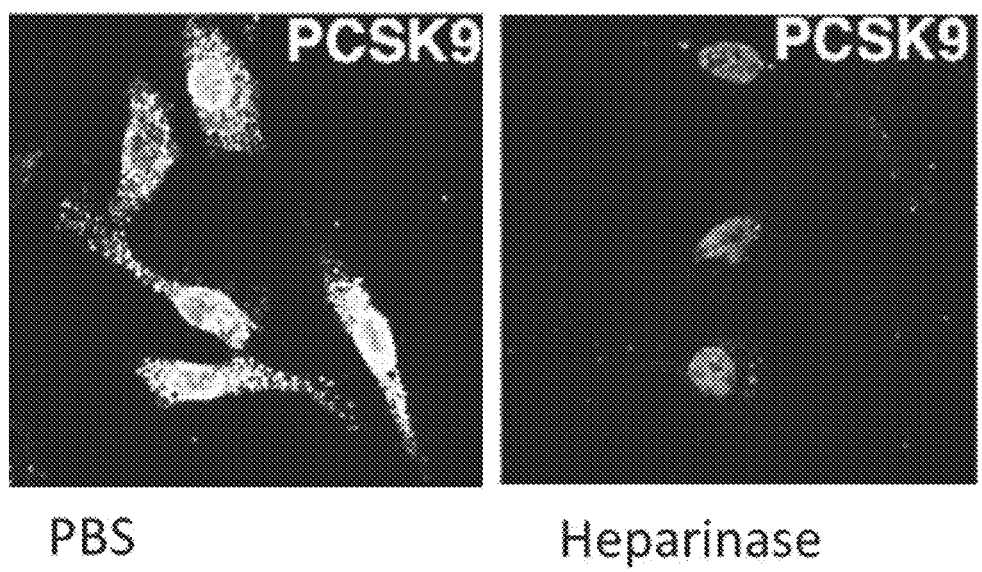
Figure 2:
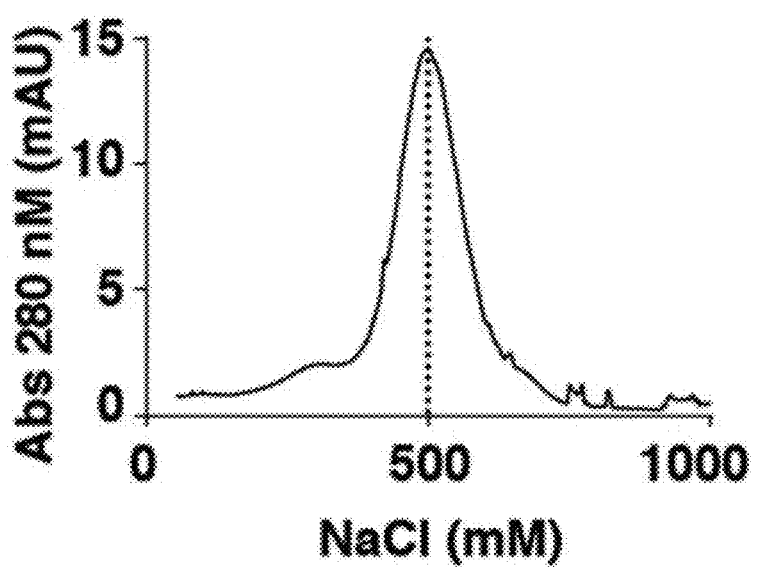
Figure 3:
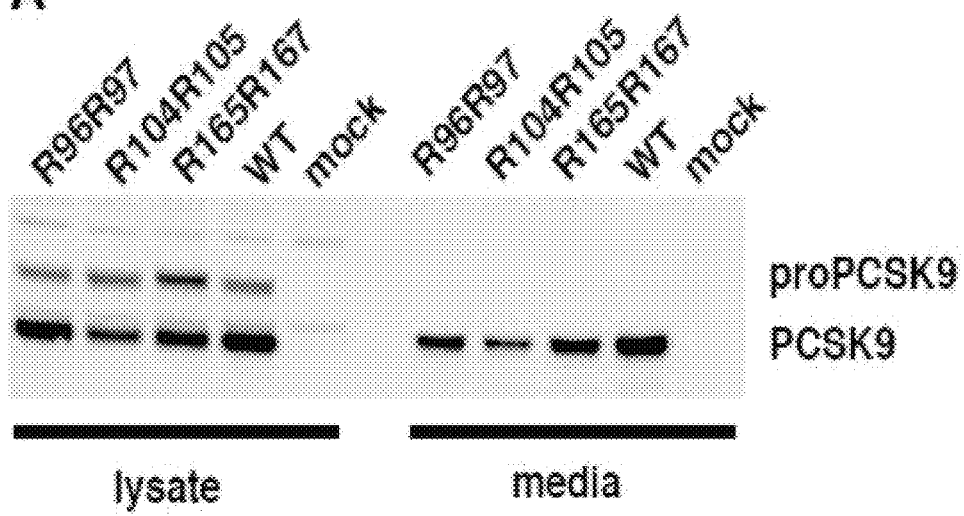
FIG. 3: PCSK9 variants, in which indicated amino acid residues were mutated to alanine, were transiently expressed in CHO cells. (A) Anti-PCSK9 Western blotting of cell lysate and media showed expression of all PCSK9 variants as well as correct processing from proprotein (proPCSK9) into mature PCSK9 in the cell lysate, and secretion of mature PCSK9 to the media of the cells. No expression of PCSK9 was detected in mock transfected cells. (B) PCSK9 mutants secreted to the media of transiently transfected CHO cells were analysed for binding to heparin by affinity chromatography followed by Western blotting of fractions with anti-PCSK9. All mutants have alanine substitutions at the indicated positions. Wildtype (WT) PCSK9 and mutant R165R167 were eluted in fractions corresponding to 0.3-0.4 M NaCl, whereas PCSK9 mutants R96R97 and R104R105 showed decreased affinity for heparin and were found in the flow through or in the first fraction. PCSK9 mutants R93R104R105H139 and R93R96R97R104R105H139 were found exclusively in the flow through and did not bind to heparin. (C): The HSPG binding domain is positioned opposite the LDLR binding site as shown in a space filling model of PCSK9 in a surface representation of PCSK9 in complex with a LDLR fragment (PDB:3P5B). The LDLR fragment contains the beta propeller domain and EGF domains A and B and L7, while PCSK9 C-terminal, catalytic domain, and prodomain are shown with the basic helix. The modeled heparin fragment is shown as sticks. (D) Endogenous PCSK9 and ApoE from the culture medium of HepG2 cells showed similar binding to heparin when analyzed by affinity chromatography and Western blot.
Figure 3:
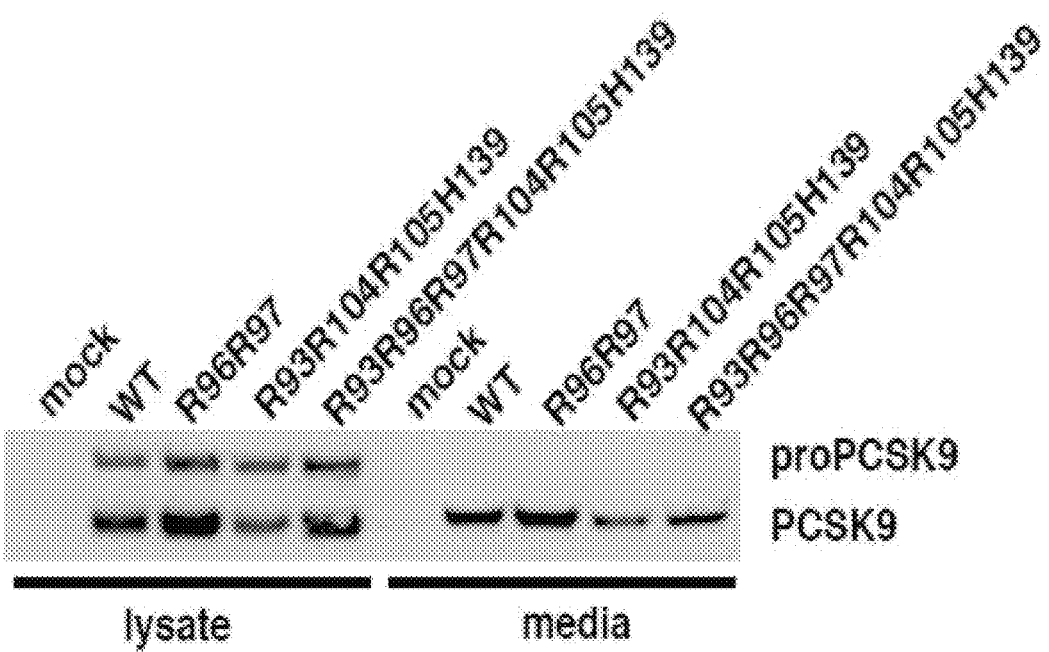
Figure 3:
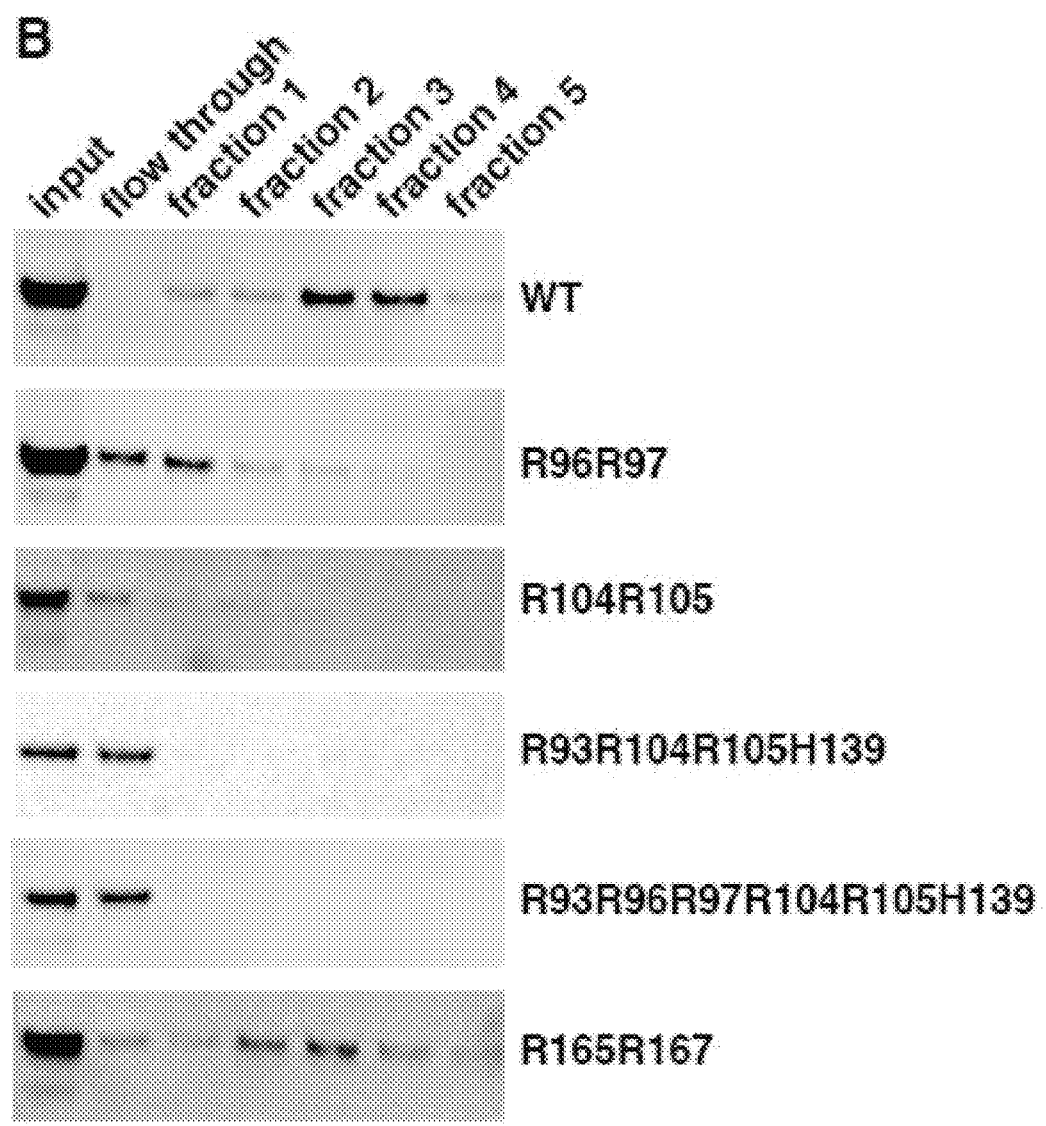
Figure 3:
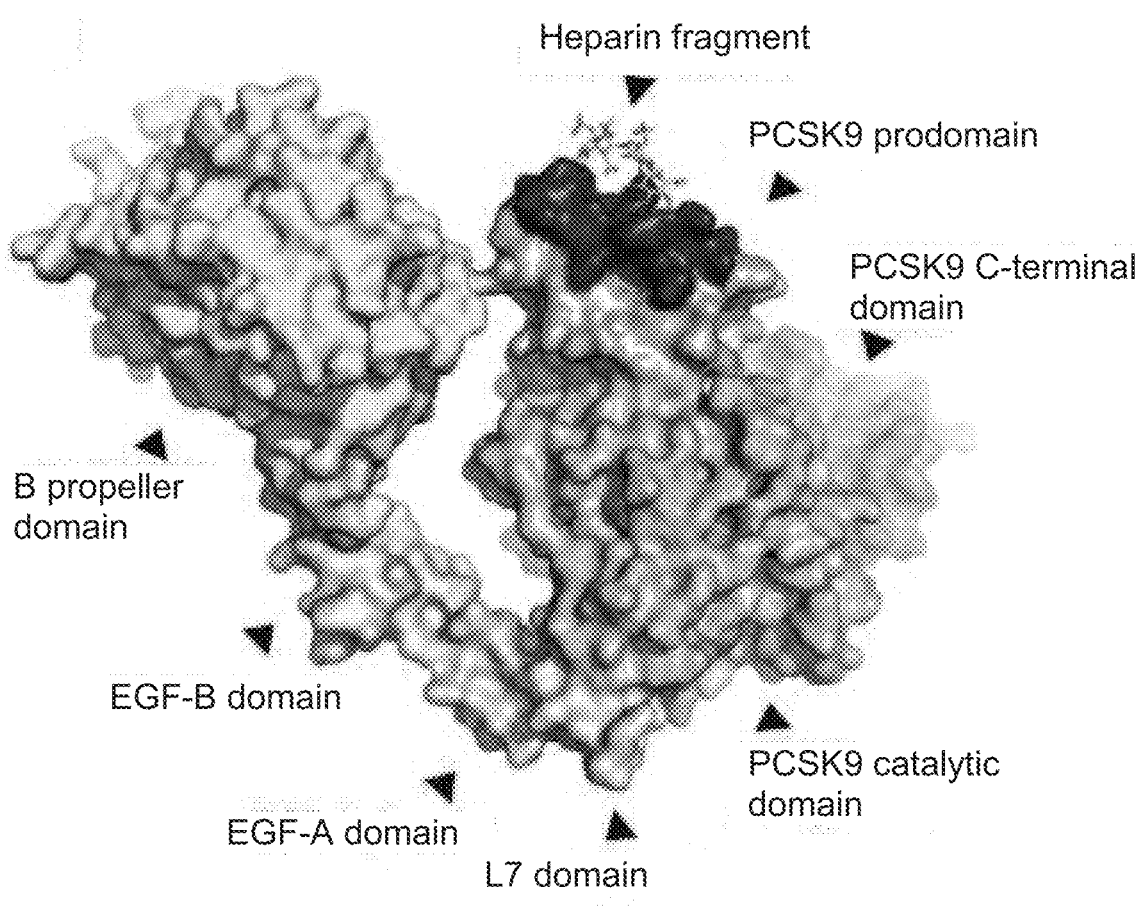
Figure 3:
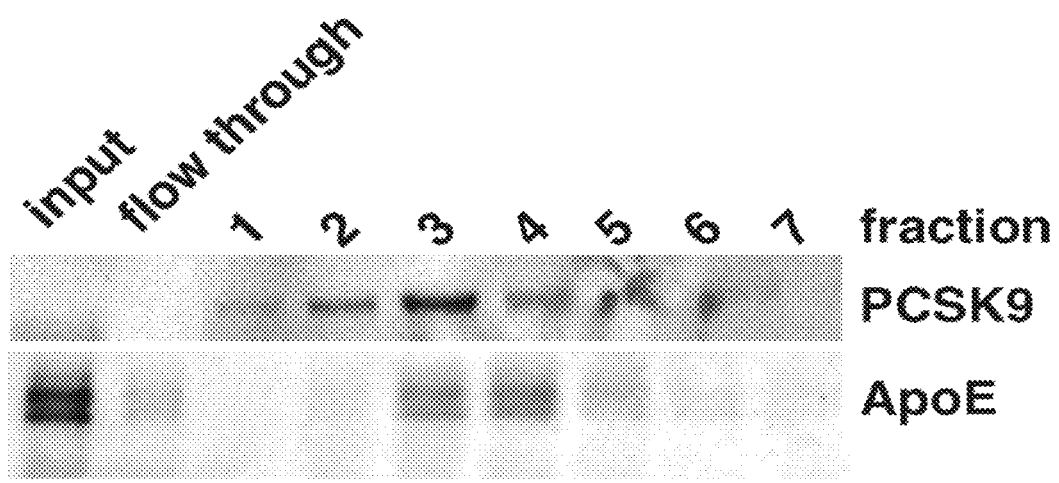

We examined the electrostatic surface of PCSK9 (PDB: 2PMW) (FIG. 2B), and identified a putative heparin binding site composed of six surface exposed basic residues located in the PCSK9 prodomain. The binding site is formed by arginine (R) residues at position 93, 96, 97, 104, and 105 and histidine (H) at position 139, which show perfect pairing with sulfate groups of a heparin pentasaccharide (SANORG) (Herbert et al., 1996) (Herbert et al., 1996) (FIGS. 2B and 2C). The site is found opposite to the LDLR binding surface located in the inactive catalytic domain of PCSK9 (FIG. 2A). Docking of heparin fragment onto a co-crystal structure of PCSK9 in complex with LDLR (PDB:3P5B) suggested that HSPG binding allows subsequent PCSK9:LDLR complex formation (FIG. 3C).

Example 2: Heparinase Treatment Inhibits PCSK9 Cell Surface Association In Vitro and Protects the LDL Receptor Against PCSK9-Induced Degradation In Vivo We speculated that HSPG might be involved in the capture of PCSK9. Thus, we treated human hepatocyte-derived HepG2 cells stably expressing PCSK9 with heparinase I. The enzyme heparinase I cleaves heparan sulfate GAG chains at the 1,4 O-linkage between uronic acid and D-glucosamine, thereby removing cell surface heparan sulfate chains.

HepG2 cells stably transfected with PCSK9 were seeded at 50.000 cells per coverslip and incubated overnight before addition of heparinase I (Sigma Aldrich/H2519) in PBS (0.0002 UN/ml) or PBS alone. Cells were incubated for 1 h. at 37▫ C, before fixation in 4% paraformaldehyd and immunostaining of non-permeabilized cells with primary and secondary antibodies. Nuclei were visualized with Hoechst dye (Sigma Aldrich). Images were acquired on a Zeiss LSM780.

Indeed, treatment resulted in a marked decrease in the intensity of surface PCSK9 staining, suggesting that HSPG are critical for PCSK9 cell binding (FIG. 2D).

To test the effect of enzymatic removal of heparan sulfate GAGs on PCSK9 activity in vivo 10-12 week-old male BALB/cJRj mice were infused with heparinase I (30 U) administered through a tail vein catheter 5 min prior injection of PCSK9 (10 µg). In control mice the heparinase injection and/or the PCSK9 injection were replaced with an injection of 0.9% saline. During heparinase infusion, mice were lightly anaesthetized with isoflurane continuously administered through a mask. One-hour post injection mice were sacrificed and liver tissue samples were harvested and snap frozen before extraction of proteins and evaluation of LDLR levels by Western blot (FIG. 10 A) Injection of heparinase I completely protected LDLR from PCSK9-induced degradation, demonstrating that HSPGs are instrumental in PCSK9 induced degradation of LDLR in vivo (FIGS. 10 A and B).

To verify the direct interaction between PCSK9 and heparan sulfate GAG chains, we employed affinity chromatography using Sepharose beads covalently coupled with heparin.

Purified PCSK9 was loaded onto a 5 ml HiTrap Heparin HP column (GE Healthcare) in PBS. The column was connected to an Äkta Prime and washed with 5 column volumes of 10 mM NaH2PO4 (pH 7.4). PCSK9 was eluted using a linear gradient of 10 mM NaH2PO4 (pH 7.4) and 2 M NaCl and fractions were analyzed by SDS-PAGE. Based on the measured conductivity, the elution profile was transformed to a function of NaCl concentration using the transformation coefficient 0.065 mS/mM NaCl. PCSK9 was retained on the heparin column and eluted at a NaCl concentration of approximately 500 mM (FIG. 2E), indicating a strong and highly specific interaction with heparin.

In a different experiment, conditioned media from HepG2 cells were incubated with Heparin Sepharose CL-6B beads (GE Healthcare) in 10 mM NaH2PO4 (binding buffer). Following overnight incubation on a rotor at 4□ C, beads were washed in binding buffer before batch elution of heparin bound proteins in increasing concentration of NaCl. PCSK9 in input, flow through, and elution fractions were evaluated by Western blotting.

We found that endogenous PCSK9 from conditioned media of HepG2 cells also bound heparin Sepharose and showed similar elution profile as that of ApoE, a well-established HSPG binding protein (FIG. 3D).

Example 3: Identification of Residues Important for the PCSK9/HSPG Interaction

To further narrow down critical residues involved in the PCSK9/HSPG interaction, PCSK9 variants with point mutations in the HSPG binding motif were cloned and expressed. Mutations were introduced by PCR in order to replace the charged amino acid arginine (Arg/R), lysine (Lys/K) and histidine (His/H) identified by 3D structure model docking by neutral residues such as alanines (Ala/A).

The human wild type and the following alanine substitution variants were analysed: Wild type PCSK9 (SEQ ID NO: 1)

Mutant R93
Mutant R96R97
Mutant R104R105
Mutant R165R167
Mutant R93R104R105H139A
Mutant R93R96R97R104R105H139

Since improper folded PCSK9 is generally not cleaved in the propeptide and therefore retained in the endoplasmic reticulum, correct folding of the PCSK9 mutant variants can be evaluated by monitoring their processing and secretion. Processing of proPCSK9 into mature protein and secretion of mature PCSK9 variants were assessed by transient transfection of Chinese Ovary Hamster (CHO) cells followed by Western blot analysis of PCSK9 in cell lysates and in the surrounding medium (FIG. 3A).

The ability of the PCSK9 mutant proteins to bind to heparin was assessed by affinity chromatography followed by Western blotting with anti-PCSK9 antibody.

Conditioned media from CHO cells transfected with PCSK9 variants of interest were incubated with Heparin Sepharose CL-6B beads (GE Healthcare) in 10 mM NaH2PO4 (binding buffer). Following overnight incubation on a rotor at 4° C., beads were washed in binding buffer before batch elution of heparin bound proteins in increasing concentration of NaCl. PCSK9 in input, flow through, and elution fractions were evaluated by Western blotting.

Mutants R93, R96R97 and R104R105 show less affinity for heparin compared to wild-type PCSK9 or mutant R165R167, and mutants R93R104R105H139 and R93R96R97R104R105H139 do not bind heparin and are found exclusively in the flow-through (FIG. 3B).

Example 4: PCSK9 Variant with Mutated HSPG-Binding Domain Fails to Induce LDL Receptor Degradation Purified PCSK9 variants were tested in a cell assay to test their ability to induce degradation of LDLR compared to wild-type PCSK9. Induction of LDLR degradation was analyzed by incubation of HepG2 cells with wild type PCSK9 (WT) or the above PCSK9 mutants and LDLR levels were assessed by Western blotting. HepG2 cells were seeded at a density 250.000 cells per well in 12-well plates. After overnight incubation, the media was replaced with fresh media containing PCSK9 WT or mutant R93R96R97R104R105H139. Cells were harvested and lysed following 18 hours incubation and LDLR levels were assessed by Western blotting and quantification by densitometry.

Figure 4:
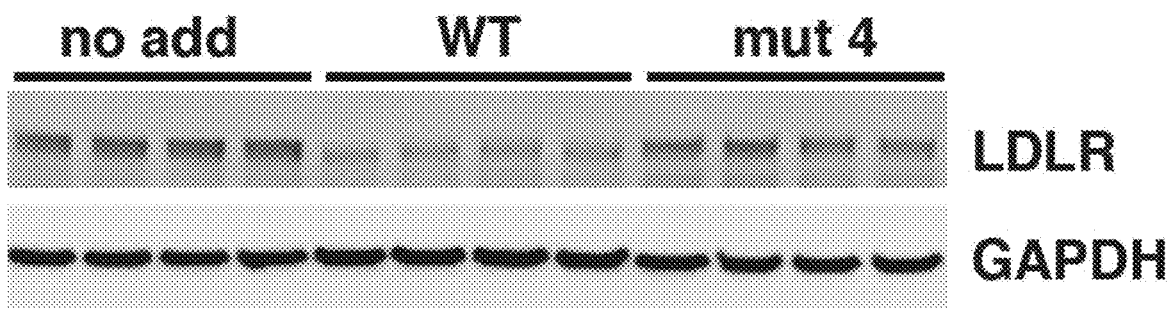
FIG. 4: HepG2 cells incubated 18 hours with WT PCSK9 (10 nM) show significantly lower levels of LDLR than cells incubated with mutant (R93R96R97R104R105H139) PCSK9 (mut). LDL receptor levels were evaluated by Western blotting (A), levels of GAPDH are shown as control. Bar graphs (B) show average values of LDLR quantified by densitometry (n=3) with standard error of mean (SEM). Results were evaluated using student's t-test. p<0.01, **p<0.0001.
Figure 4:
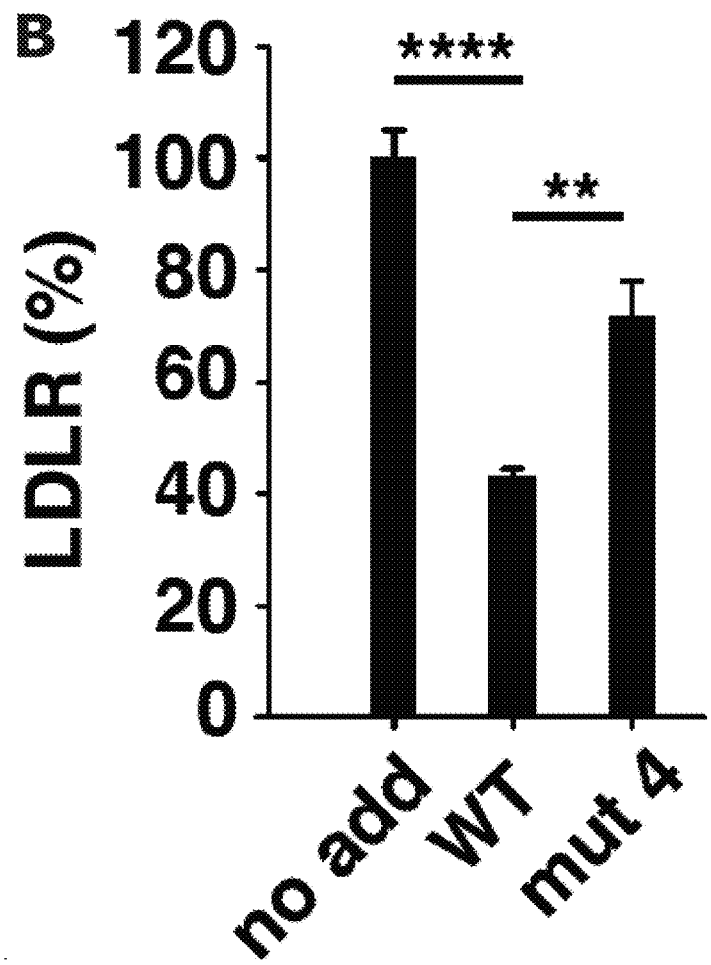

The LDLR levels in cells incubated with mutant R93R96R97R104R105H139 were markedly (approximately twice) higher compared to the levels measured in cells incubated with WT PCSK9 (FIGS. 4A and B), showing that mutations within the HSPG-binding domain resulted in reduced PCSK9-induced LDLR degradation.

Example 5: Heparin and Heparin Analogues Prevent PCSK9:LDLR Complex Formation

Using proximity ligation assay (PLA), we tested whether exogenously added heparin competes with cell surface HSPG for the binding of endogenous PCSK9 and thereby prevent PCSK9:LDLR complex formation (Soderberg et al., 2006).

The PLA (Duolink□II, Olink Bioscience) was performed according to manufacturer's protocol using anti-PCSK9 (R&D systems/AF3888), and anti-LDLR (Abcam/ab52818) as primary antibodies. PCSK9 and LDLR located within 30 nm from each other are visualized by oligonucleotide-conjugated secondary antibodies that hybridize with circle-forming oligonucleotides thereby priming rolling circle amplification. The amplified DNA is visualized by addition of complementary fluorescently-labeled oligonucleotides (Soderberg et al., 2006)

Figure 5:
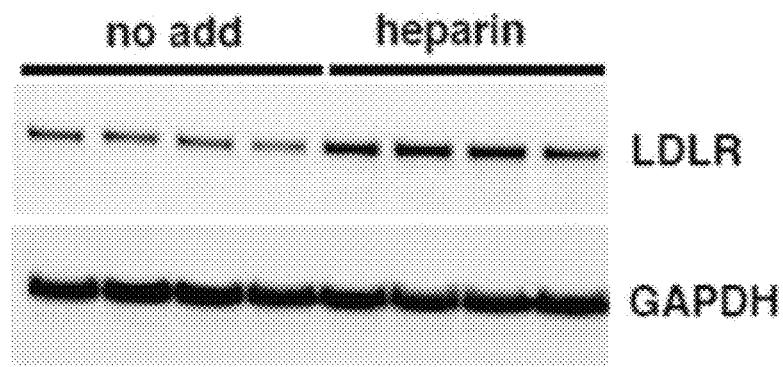
FIG. 5: HepG2 cells incubated 24 h with heparin (50 U/ml) show increased levels of LDLR evaluated by Western blotting (A). GAPDH levels are shown as control. Bar graphs (B) show average values with standard error of mean (SEM) of LDLR quantified by densitometry (n=4). Incubation with heparin also results in increased PCSK9 levels in the medium as measured by ELISA (C). Bar graphs show the average PCSK9 concentration with SEM (n=4). Results were evaluated using student's t-test. *p<0.001, **p<0.0001. (D)=PLA analysis of non-permeabilized HepG2 cells showed that co-localization between LDLR and PCSK9 was markedly reduced upon incubation of cells with heparin (50 U/ml).
Figure 5:
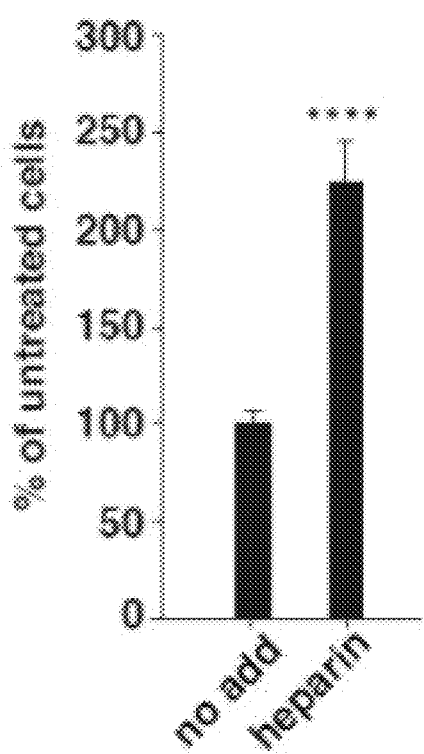
Figure 5:
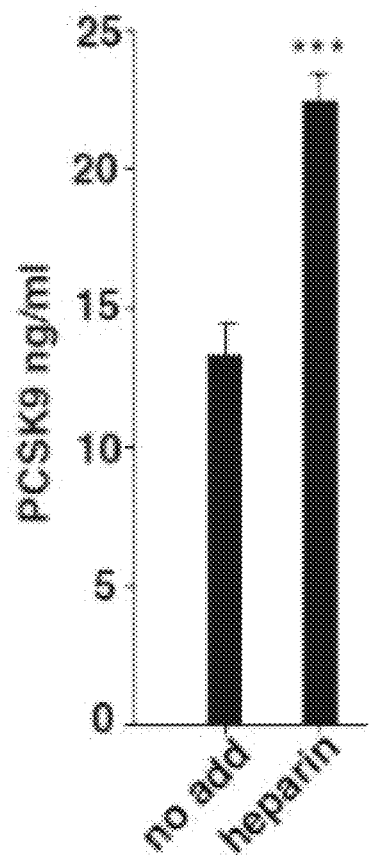
Figure 5:
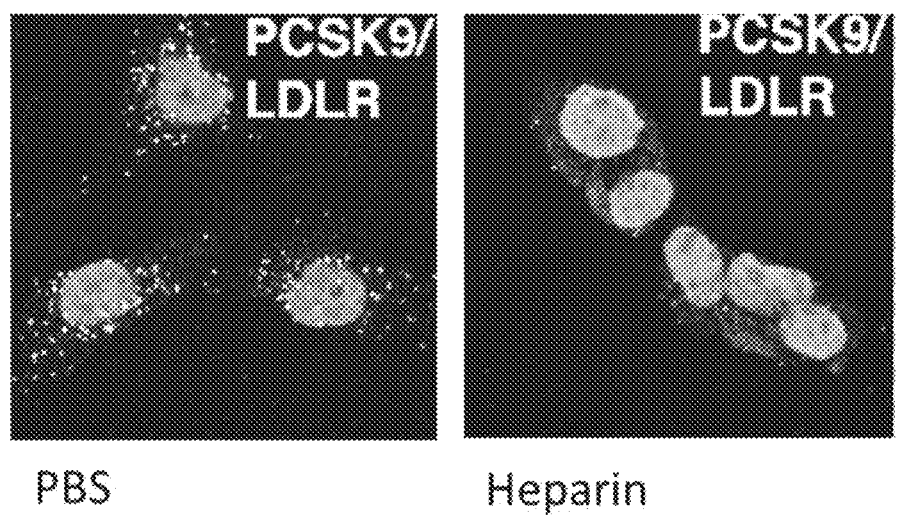

Using this assay on endogenous cell surface PCSK9 and LDLR in non-permeabilized HepG2 cells, abundant clusters of PCSK9:LDLR complexes were observed (FIG. 5D). These were markedly reduced both in numbers and intensity upon incubation with heparin, suggesting that PCSK9 binding to HSPG is instrumental in the subsequent complex formation with cell surface LDLR.

Figure 8:
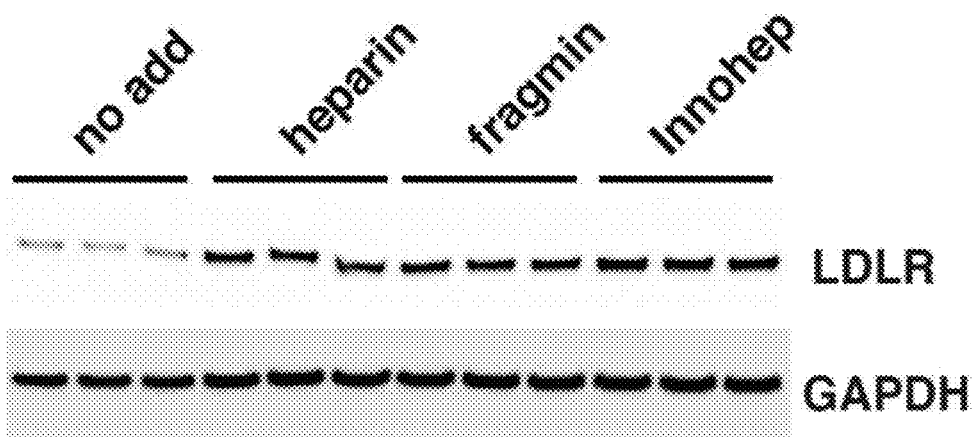
FIG. 8: (A) Western blot of LDLR in HepG2 cells following 18 hours incubation with fragmin (100 U/ml) and Innohep (100 U/ml), showing that these two therapeutic preparations of low-molecular weight heparins can increase the cellular level of LDLR comparable to the effect of heparin (50 U/ml). Western blot of GAPDH is shown as loading control. (B) Western Blot showing LDLR levels in liver of mice 1 hour after intravenous administration of 10 µg PCSK9 alone or in combination with 50 U Heparin. 50 µg membrane preparations were loaded. As control is shown Western Blot for sortilin, a PCSK9 receptor previously shown not to be target of PCSK9 induced degradation. (C) Quantification of B) Bands were quantified by densitometry and dot plot show the individual level of each sample in percent of vehicle (0.9% NaCl) injected controls with mean values and SEM. Mice co-injected with PCSK9 and Heparin show significantly higher level of LDLR (60.3±12.3% LDLR versus 24.0±4.04%, n=7 mice/group, p=0.0157, two-tailed student's t-test). (D) Autoradiography (16 h exposure) showing immunoprecipitation of native human $^{35}$S labeled PCSK9 by serum (1 µl) from three rats immunized with DNA encoding rat PCSK9 with human HSPG binding domain. As negative controls were used preimmune serum from the animals. (E) Western Blot showing LDLR in HepG2 cells after overnight incubation with preimmune or immune IgG (1 µg/ml). A markedly increased level of cellular LDLR was seen following incubation with immune IgG compared to preimmune controls. (F) Autoradiography (16 h exposure) showing immunoprecipitation of human $^{35}$S-PCSK9 by 24 individual mAbs (500 µl conditioned hybridoma media) selected in ELISA screening performed by Aldevron. As controls were used mAb #2A8 which did not show any PCSK9 immunoreactivity in an ELISA screen (*) (mAb #2A8 was tested unspecific in ELISA test screen performed by Aldevron), and unconditioned hybridoma media (**). (G) Bar graphs showing LDLR levels (average of 2-4 experiments with SEM) in HepG2 cells incubated with mAbs (1:10 dilution of conditioned hybridoma media) as analysed by Western Blot. Twelve individual mAb clones give an approximately two-fold increase LDLR. (H) Autoradiography (16 h exposure) showing immunoprecipitation of human $^{35}$S-mutant PCSK9 (with R93R96R97R104R105H139 mutated to alanine residues) by 12 individual mAbs (500 µl conditioned hybridoma media) all showing PCSK9 inhibitory effect. As control was used a polyclonal antibody (pAb, AF3888 from R&D systems). Three of the mAbs failed to precipitate the PCSK9 mutant indicating that they specifically recognize the HSPG binding domain. (I) Autoradiography showing immunoprecipitation of $^{35}$S-PCSK9 WT and variants R96R97, R104R104, R93R96R97H139, and R93R96R97R104R105H139 by mAbs 1G8, 5E11, and 10E5 indicating that the mAbs recognize epitopes within the HSPG binding domain. As control was used R&D Systems AF3888 (pAb).
Figure 8:
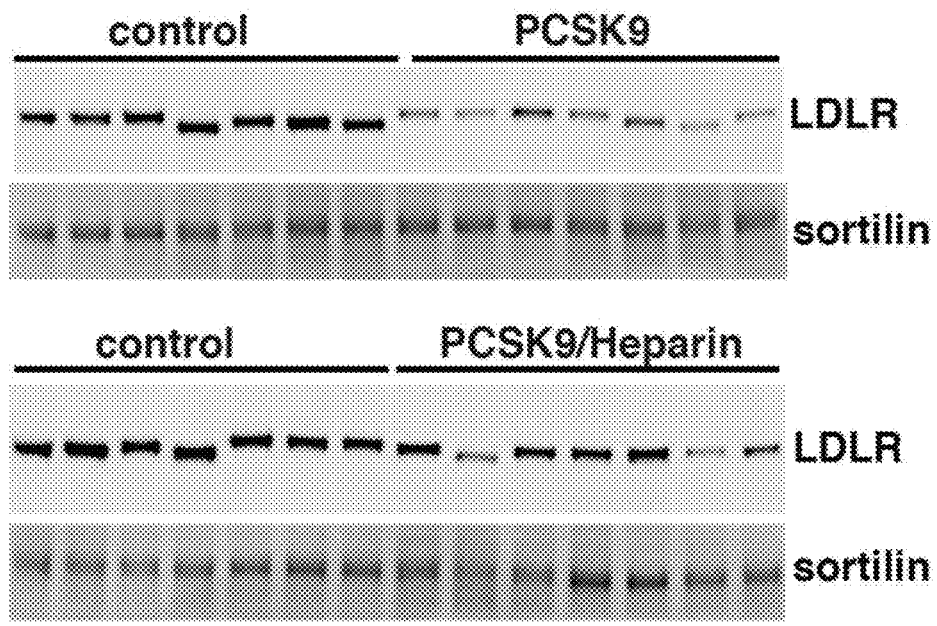
Figure 8:
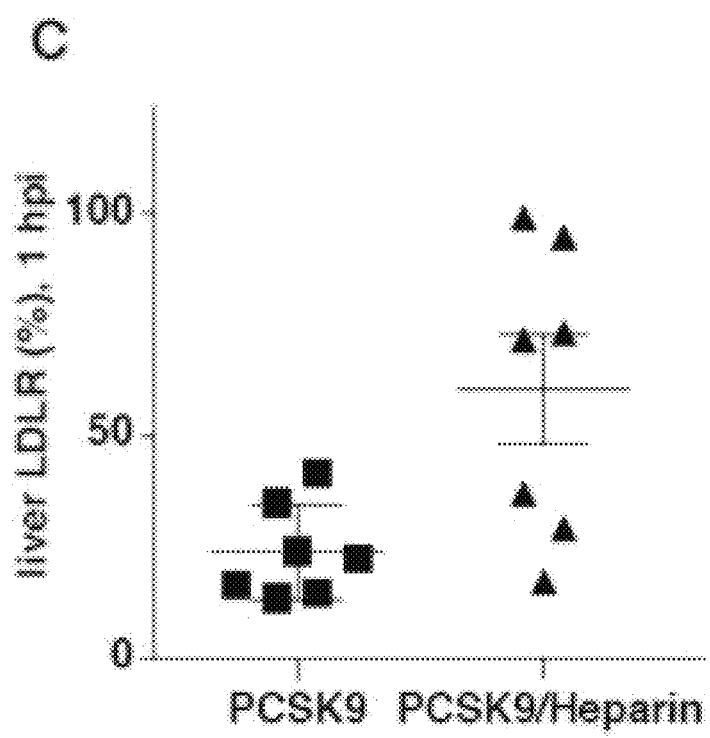
Figure 8:
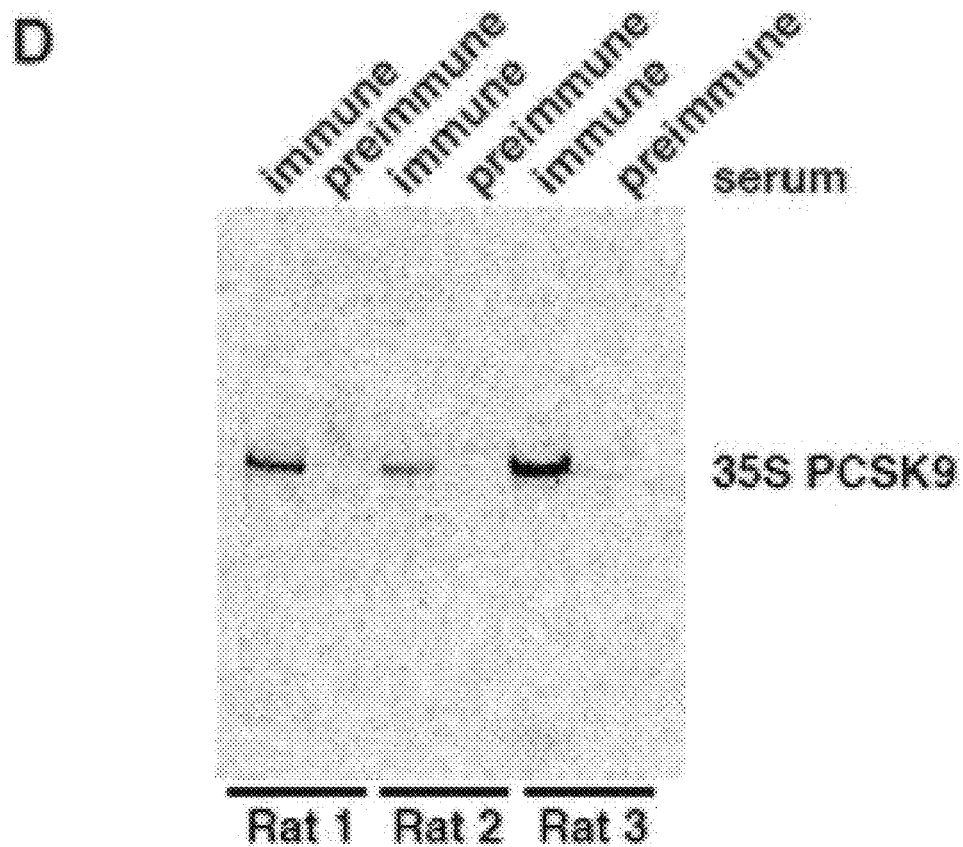
Figure 8:
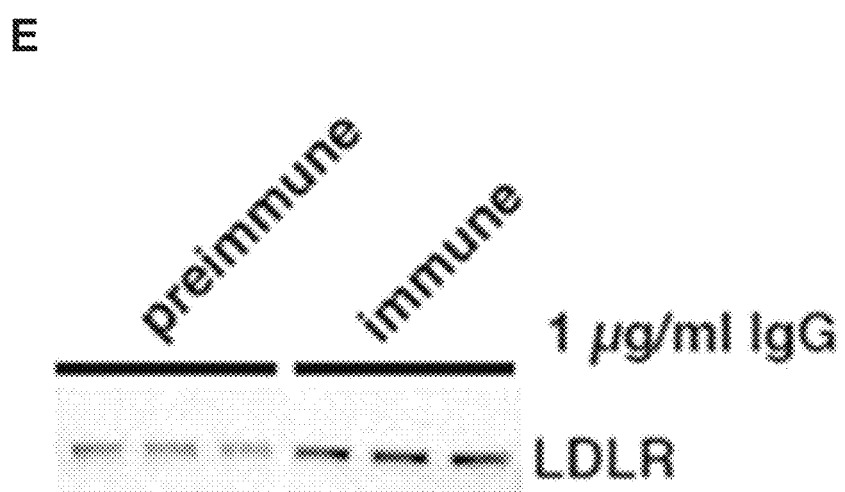
Figure 8:
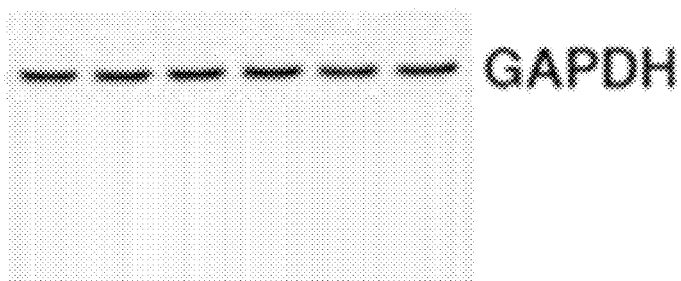
Figure 8:
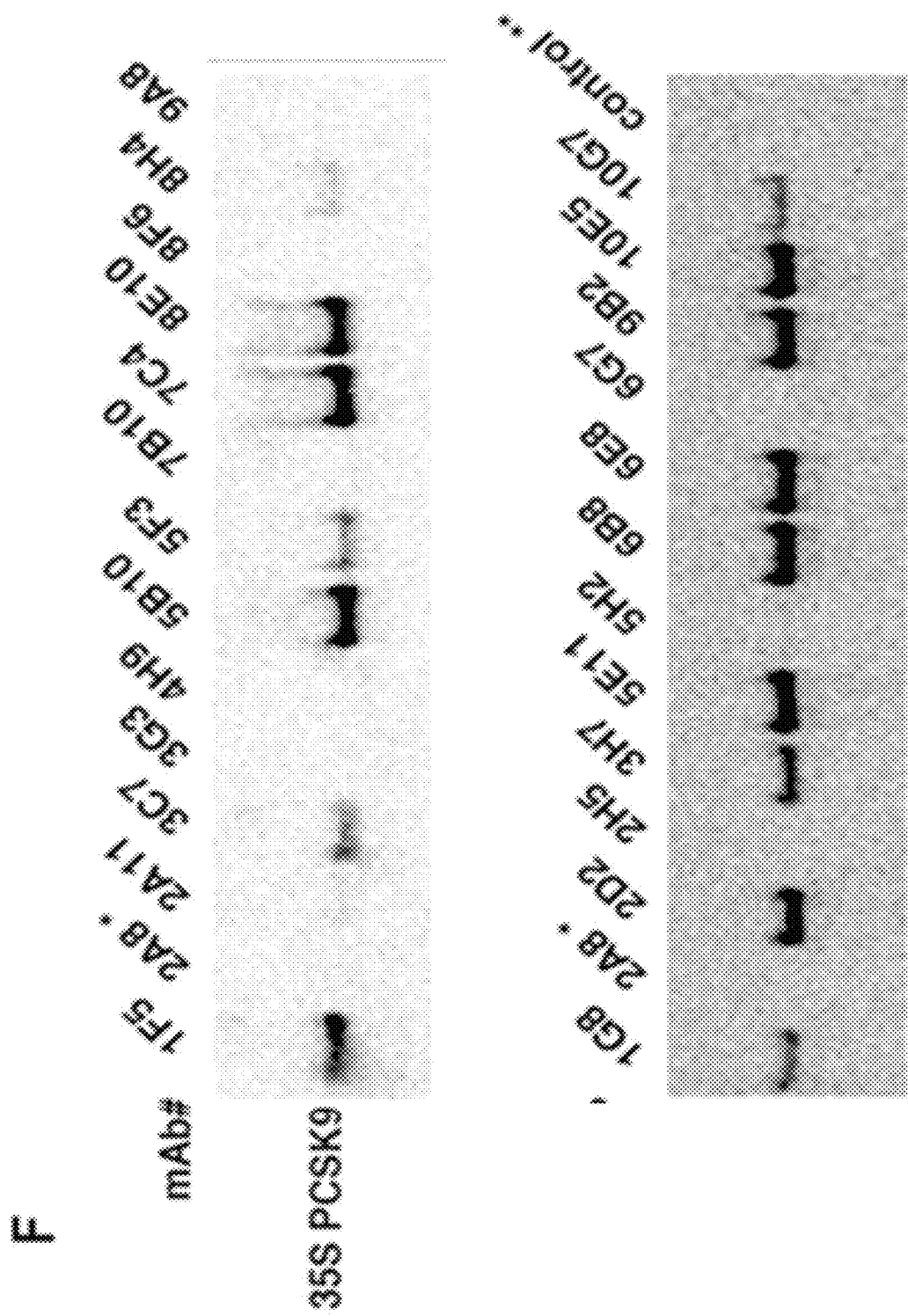
Figure 8:
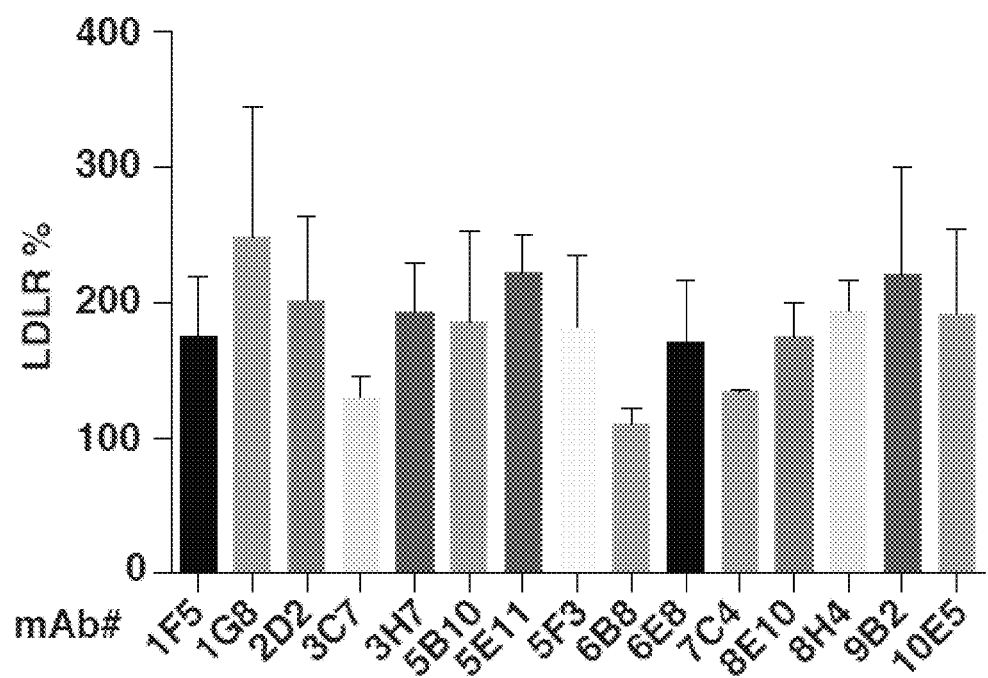
Figure 8:
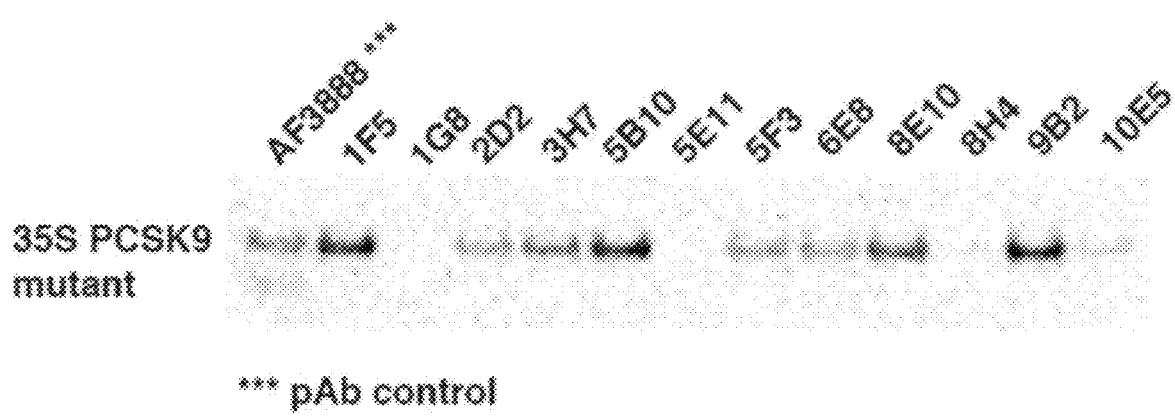
Figure 8:
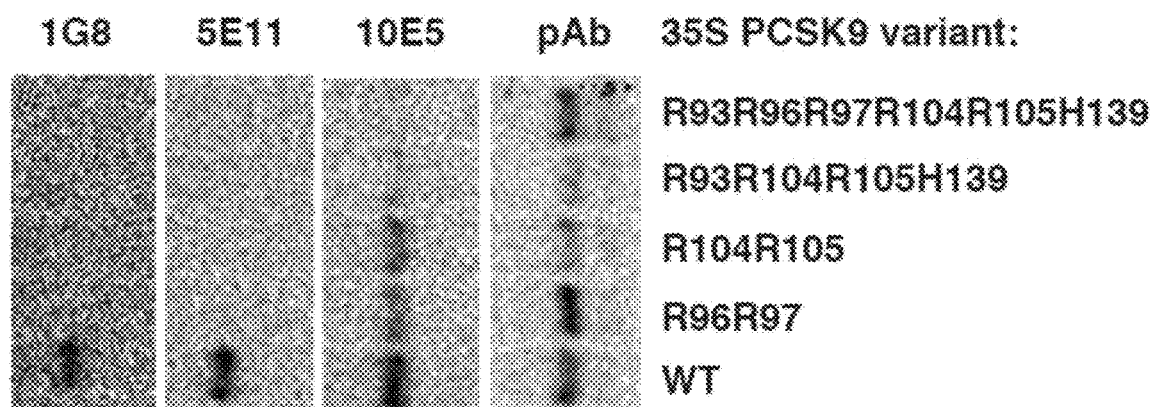

We found that incubation of HepG2 cells with heparin (50 U/ml for 18 hrs) resulted in two to three-fold higher level of LDLR protein (FIGS. 5A-5B), and a similar effect was observed with two therapeutic preparations of low-molecular weight heparins (FIG. 8A).

Figure 6:
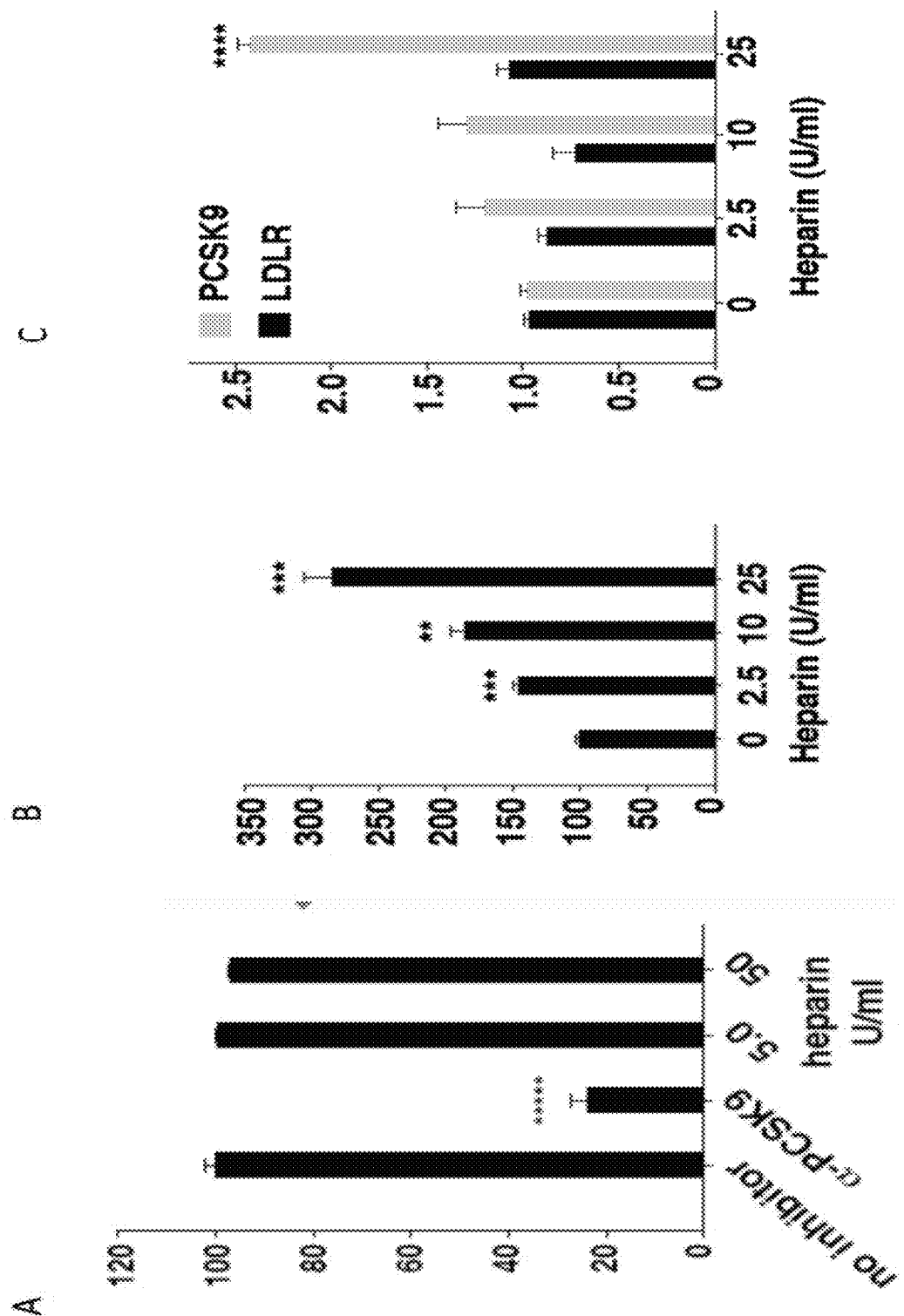
FIG. 6: (A) Using a cell-free PCSK9/LDLR binding assay (BPS Bioscience) we found that heparin (5 and 50 U/ml) does not inhibit the direct interaction of PCSK9 with LDLR in contrast to the control inhibitor anti-PCSK9 antibody (5 nM), which targets the LDLR binding region of PCSK9 (BPS Bioscience 71207). In the binding assay the chemiluminescent signal from biotinylated PCSK9 bound to immobilized LDLR is quantified and results are here shown normalized with respect to signal from samples without inhibitor. Bar graphs show average values (n=3) with standard deviation error bars. Results were evaluated using student's t-test. *****p<0.00001. Y-axis: % if no inhibitor. (B) Dose dependent effect of heparin on PCSK9 in the medium as measured by ELISA (n=3). Y-axis: PCSK9 in media (%); (C) Quantitative analysis of mRNA levels in cell lysates by RT-PCR.

The increase in cellular LDLR in heparin-treated HepG2 cells was dose dependent and accompanied by a marked increase in PCSK9 in the medium (FIG. 6B). The PCSK9 concentration was measured using Human (DPC900) Quantikine ELISA kit from R&D Systems according to manufacturer's protocol.

The increase in cellular LDLR and extracellular PCSK9 induced by heparin occurred at the post translational level as we observed no change in mRNA, except for PCSK9 at the highest heparin concentration (FIG. 6C).

RNA extraction from HepG2 cells was performed using NucleoSpin RNA preparation kit (Macherey-Nagel), following cDNA synthesis from 0.5 μg RNA template by iScript® cDNA synthesis kit (BIORAD). Real time PCR was performed with iQ SYBR® Green supermix and iTaq® polymerase using the following primers to detect transcripts of LDLR (forward primer 5'ACGGCGTCTCTTCCTATGACA3' (SEQ. ID NO: 22), reverse primer 5'CCCTTGGTATCCGCAACAGA3' (SEQ. ID NO: 23)), PCSK9 (forward primer 5'CCTGGAGCGGATTAC-CCCT3' (SEQ. ID NO: 24), reverse primer 5'CTGTATGCTGGTGTCTAGGAGA3' (SEQ. ID NO: 25)), and GAPDH (forward primer 5'ACAACTTTGGTATCGTGGAAGG3' (SEQ. ID NO: 26), reverse primer 5'GCCATCACGCCACA-GTTTC3' (SEQ. ID NO: 27)).

We found that 25 M/ml heparin effectively antagonized PCSK9 activity as evident from approximately 2.5-fold increase in LDLR levels (FIG. 8B) despite the two-fold increase in PCSK9 mRNA level.

HepG2 cells incubated 24 h with heparin (50 U/ml) showed increased levels of LDLR as evaluated by Western blotting (FIG. 5A). LDLR levels were also quantified by densitometry (n=4) (FIG. 5B). Incubation with heparin also resulted in increased PCSK9 levels in the medium as measured by ELISA (FIG. 5C).

Heparin does not interfere with the direct interaction between PCSK9 and LDLR as analysed by a PCSK9/LDLR binding assay (FIG. 6 A) (BPS Bioscience) according to the manufacturer's protocol. Briefly, microtiter plate wells coated with LDLR extracellular domain were incubated with biotinylated PCSK9 in the presence of heparin (5 or 50 U/ml) or anti-PCSK9 antibody raised against the LDLR binding domain of PCSK9 (BPS Bioscience #71207). Following washing, wells were incubated with horse radish peroxidase (HRP) labeled-streptavidin and binding of PCSK9 to the LDLR extracellular domain was assessed by addition of HRP substrate and evaluation of signal using a chemiluminescence microplate reader.

The interaction between PCSK9 and LDLR was unaffected by addition of heparin indicate that binding of heparin to PCSK9 results in reduced LDLR degradation by preventing the interaction of PCSK9 with cell surface HSPGs.

Figure 7:
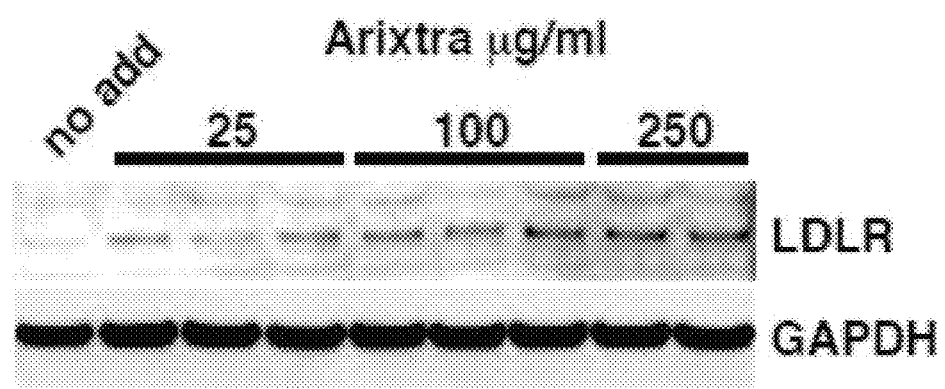
FIG. 7: HepG2 cells incubated for 24 hours with increasing concentration (0-250 µg/ml) of heparin analogue Arixtra (Fondaparinux, GlaxoSmithKline Pharma) have elevated level of LDLR. GAPDH Western Blot is shown as loading control.

HepG2 cells incubated 24 h with Fondaparinux (Arixtra) (25, 100 or 250 μg/ml) showed increased levels of LDLR as evaluated by Western blotting (FIG. 7). These results indicate that binding of a heparin analogue such as Fondaparinux to PCSK9 results in reduced LDLR degradation by preventing the interaction of PCSK9 with cell surface HSPGs.

Example 6: Heparin Mimetics Prevent PCSK9:LDLR Interaction

Figure 9:
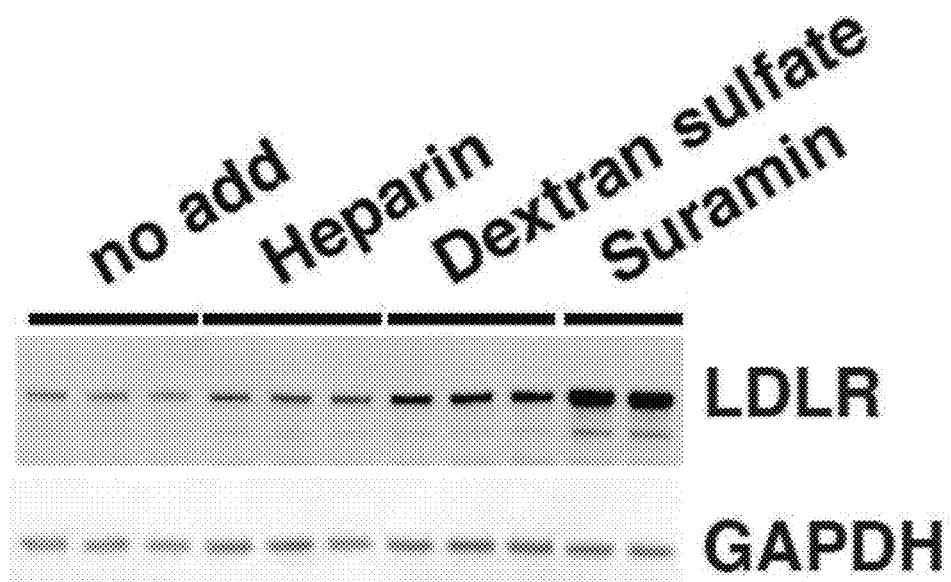
FIG. 9: (A) Western Blot of LDLR in HepG2 cells following 24 hour incubation with heparin mimetics dextran sulphate (200 µg/ml), showing that this compound can potently increase the cellular level of LDLR. For comparison is shown heparin (50 U/ml). GAPDH is shown as loading control. (B) Densitometric quantification of LDLR levels showing concentration dependent increases of LDLR in HepG2 cells after incubation with dextran sulphate (0-200 µg/ml). Bar graphs show LDLR average in % of untreated cells with SEM error bars. (C) Microscale thermophoresis (MST) binding curve for PCSK9 and dextran sulfate. Y axis: fluorescence signal. X axis: dextran sulfate or dextran concentration, $K_D$=180 µM. Circles: dextran sulfate. Squares: dextran. (D) Western Blot, densitometric quantification (E) of LDLR in HepG2 cells following 24 hour incubation with pentosan sulfate (0-200 µg/ml), showing a 4 fold increase in LDLR in lysate from cells treated with 50-200 µg/ml pentosan sulfate. Bar graphs show LDLR average in % of untreated cells with SEM error bars. (F), MST binding curve for PCSK9 and pentosan sulfate Y axis: fluorescence signal. X axis: pentosan sulfate concentration. Circles: pentosan sulfate, $K_D$=381 µM. Squares: control. (G), Quantification of LDLR in HepG2 cells following 24 hour incubation with suramin (0-200 µg/ml). Bar graphs show LDLR average in % of untreated cells with SEM error bars. Representative Western blot of LDLR in suramin-incubated HepG2 cells is shown in (A). (H): MST binding curve for PCSK9 and suramin. Y axis: fluorescence signal. X axis suramin concentration. Circles: suramin, $K_D$=190 µM. Squares: control. (I) Western Blot, and densitometric quantification (J) of LDLR in HepG2 cells following 24 hour incubation with phosphorothioateoligonucleotide S-dC-36 (0-5.0 µM), showing a concentration dependent increase in cellular receptor levels. Bar graphs show LDLR average in % of untreated cells with SEM error bars. Results were evaluated using student's t-test. *p<0.05, p<0.01, *p<0.001.
Figure 9:
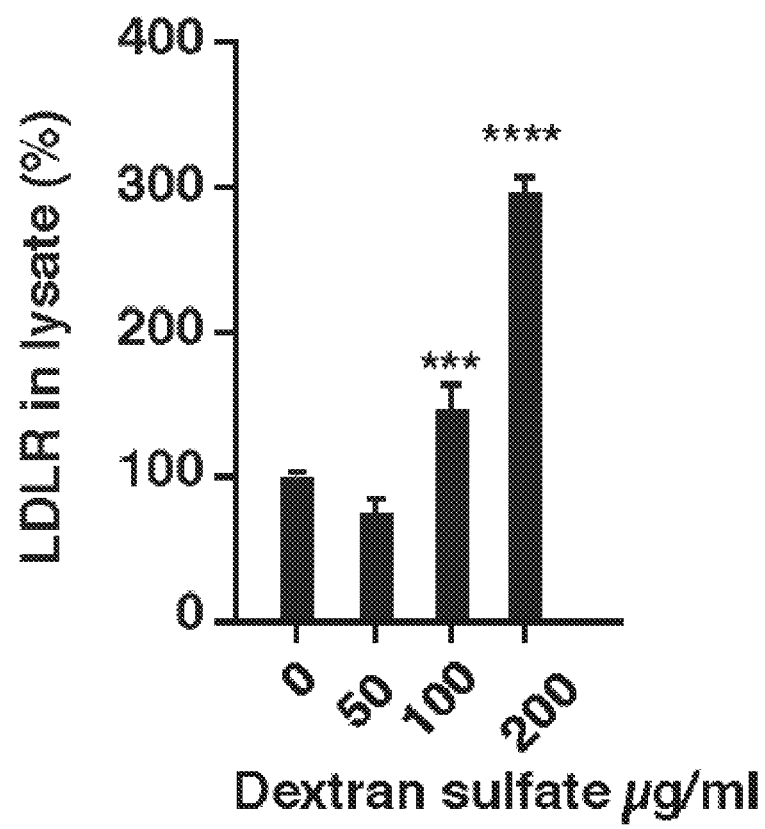
Figure 9:
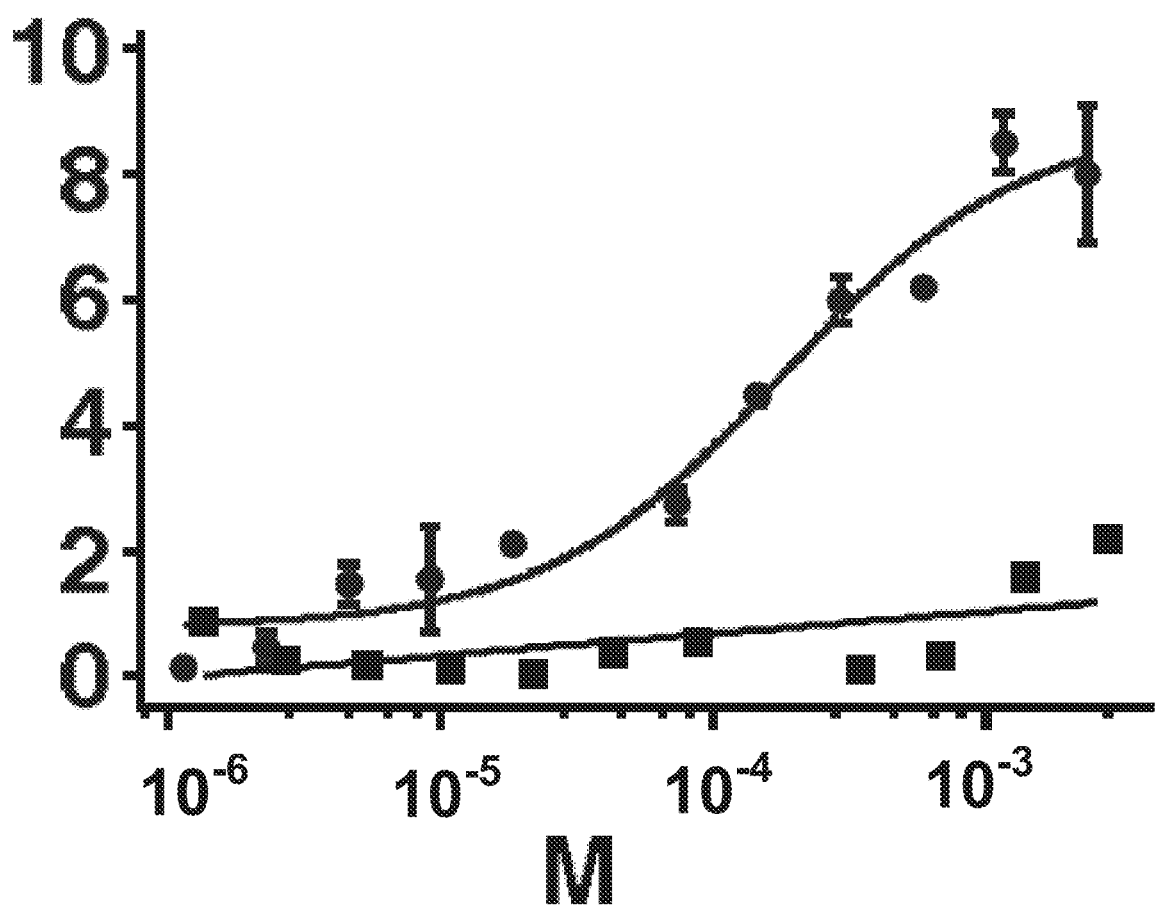
Figure 9:
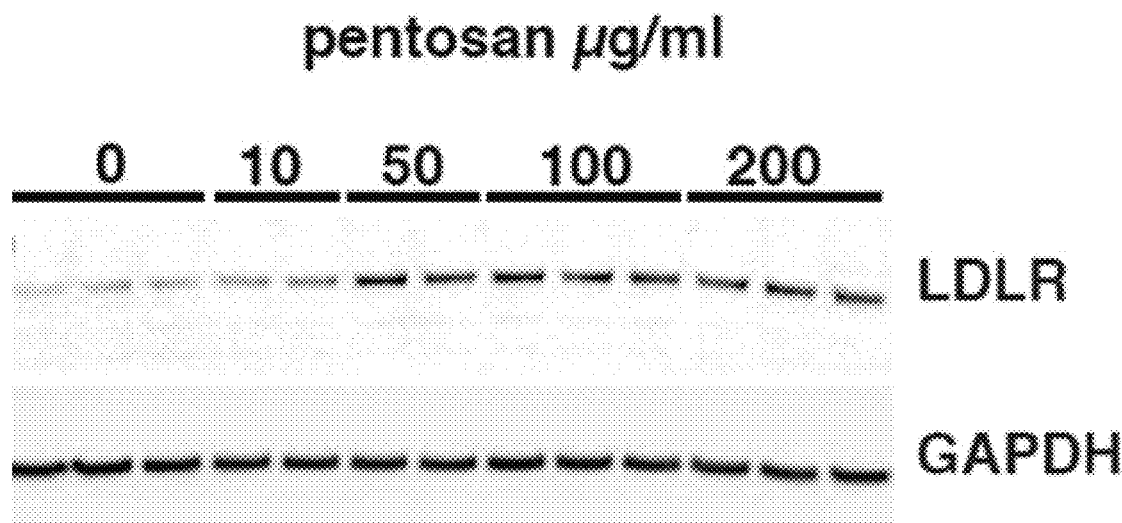
Figure 9:
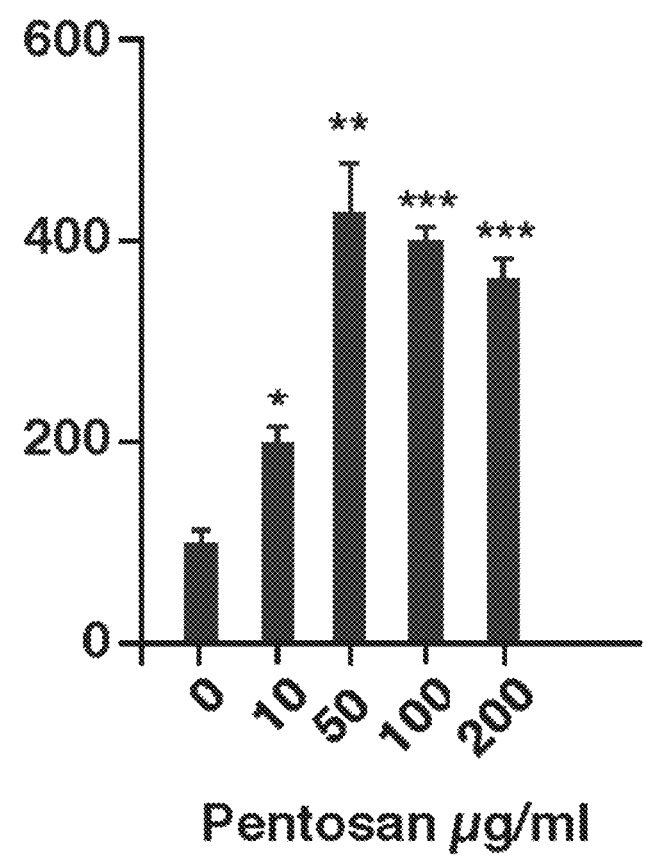
Figure 9:
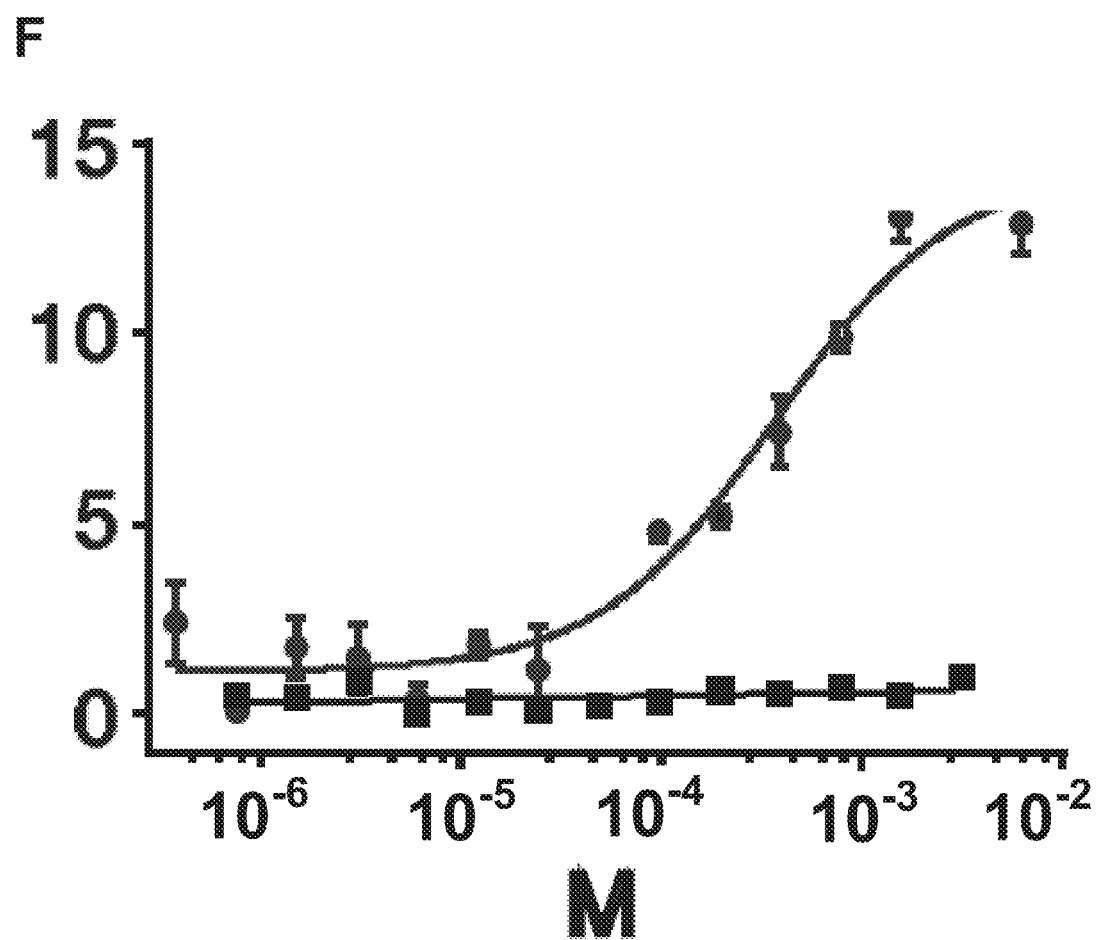
Figure 9:
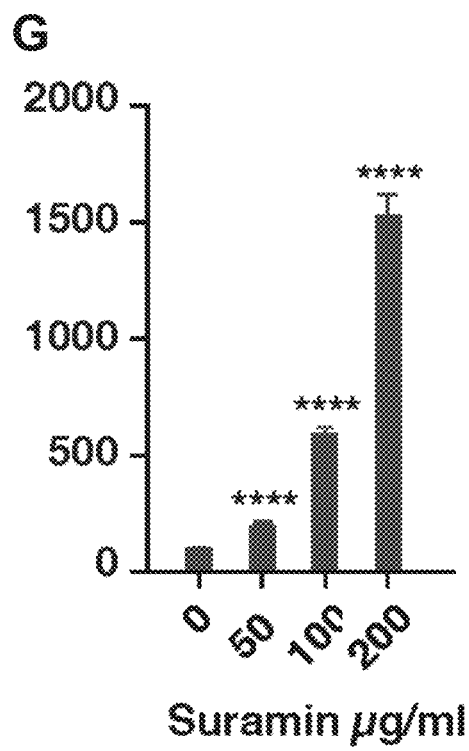
Figure 9:
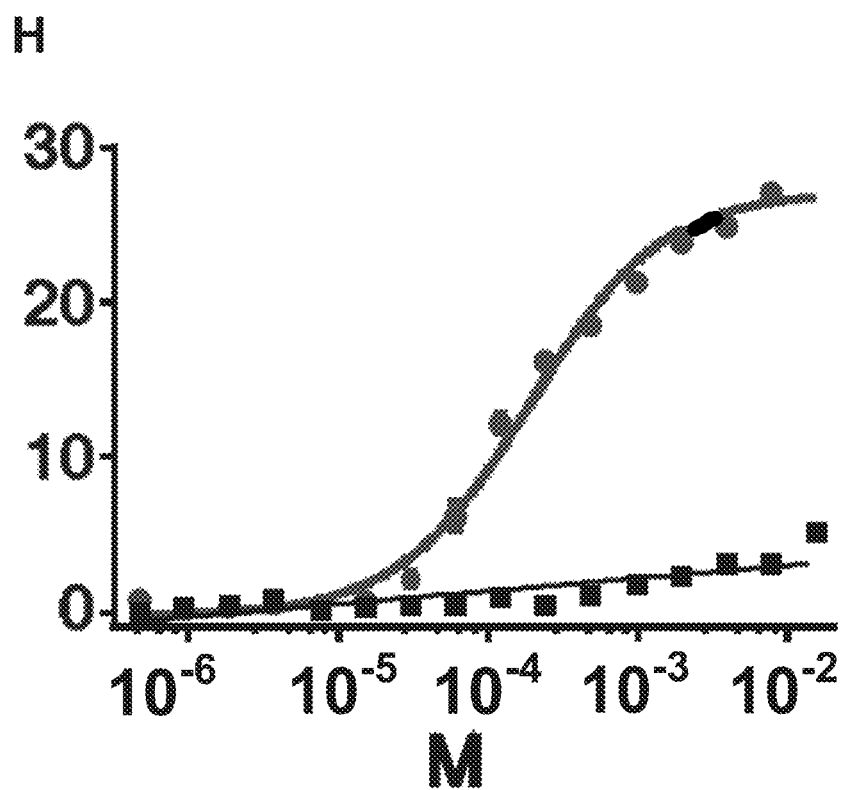
Figure 9:
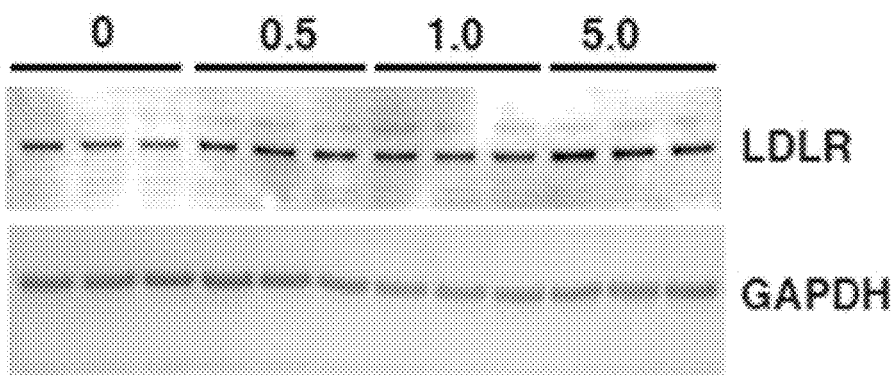
Figure 9:
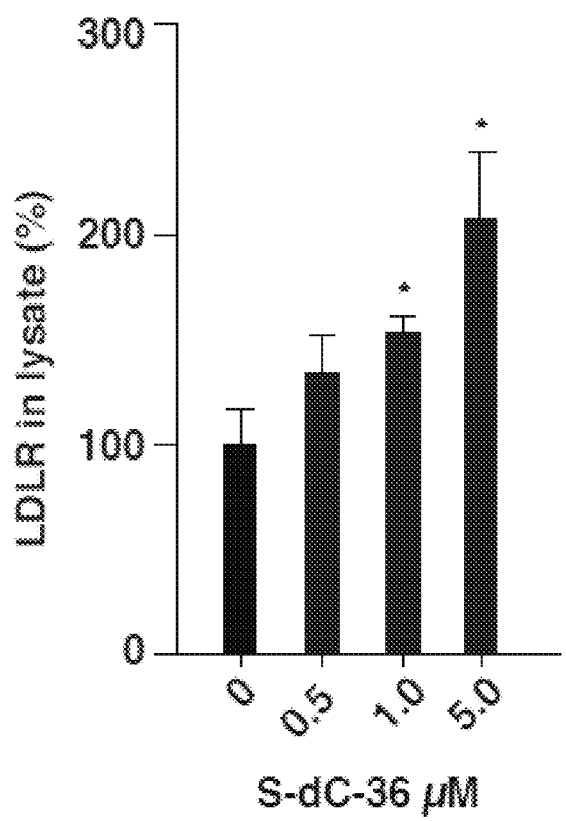
Figure 9:
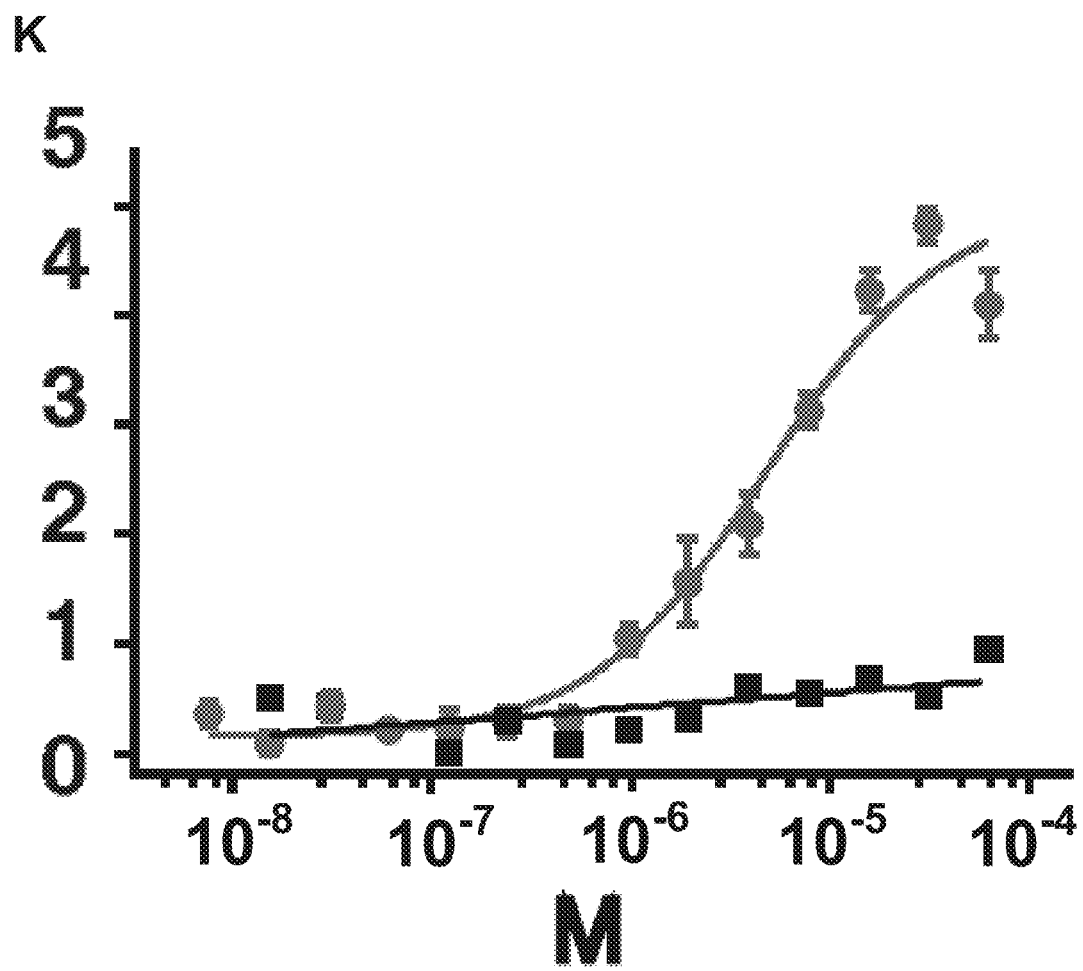

Several molecules mimicking the structure of heparin have been developed over the last 100 years for a number of therapeutic applications, seven of which are currently in clinical use. These are denoted heparin mimetics and belong to diverse chemical classes, including various oligosaccharides, oligonucleotides and naphthalene derivatives. We tested a subset of heparin mimetics for their ability to bind PCSK9 and increase LDLR in HepG2 cells (FIG. 9).

Equilibrium binding affinities between PCSK9 and ligands (suramin, dextran sulfate 5000, dextran 5000, pentosan sulfate and S-dC-36) were assessed using Microscale Thermophoresis (MST) (Jerabek-Willemsen et al., 2011). PCSK9 was labeled using the MO-L003 Monolith Blue-NHS labeling kit (NanoTemper Technologies) and a labeling efficiency of 1:1 molar ratio of protein to dye was achieved. PCSK9 was applied at a final concentration of 100 nM. The unlabeled binding partner was titrated in 1:1 dilutions (in PBS+0.05% Tween-20) where the highest concentrations were 15.4 mM for suramin, 2.3 mM for dextran sulfate 5000, 2.3 mM for dextran 5000, 16.3 mM for pentosan sulfate and 250 μM for S-dC-36. MST measurements were performed in standard-treated capillaries (NanoTemper Technologies) on a Monolith NT.115 instrument (NanoTemper Technologies) using 20% LED and 80% MST power. Laser on and off times were 5 s and 35 s, respectively. Negative controls were performed using 100 nM of labelled PCSK9 in MST buffer in all 16 capillaries under the same conditions as mentioned above. Binding curves were obtained from the temperature-jump phase at 80% MST power for suramin, dextran sulfate 5000 and S-dC-36; and from the thermophoresis+temperature-jump phase at 80% MST power for pentosan sulfate. For each binding partner, the sigmoidal dose-response curves were fitted with GraphPad Prism 6 to yield an average KD value. As fluorescence quenching of PCSK9 was observed in the presence of high concentrations of suramin, a denaturation test was performed by pre-treating PCSK9 with 10% SDS and then heating the samples for 15 min at 90° C. prior to analysis on the MST apparatus. This eliminated the quenching effect, indicating that the fluorescence quenching of PCSK9 under non-denaturing conditions was due to an actual ligand-binding event.

The sulfated oligosaccharides dextran sulfate (FIG. 9C) and pentosan sulfate (FIG. 9F) both bound directly to PCSK9 as determined using MST with an affinity of 179.5 μM and 381.3 μM, respectively, and resulted in dose-dependent increase in cellular LDLR (FIG. 9A-B and FIG. 9D-E), reaching a plateau of around 400% compared to vehicle control, and markedly superior to the maximal effect of statins in this assay. The interaction was dependent on the presence of sulfate groups as non-sulfated dextran showed no affinity for PCSK9. The sulfated naphthalene derivative suramin, an antiparasitic drug in African sleeping sickness, binds PCSK9 with an affinity of 190 μM (FIG. 9H) resulted in up to fifteen-fold increase in LDLR (FIG. 9A, 9G), accompanied by increased cellular uptake of fluorescently labelled LDL particles (FIG. 12). We further tested a 36-mer single strand DNA molecule and found that it bound PCSK9 with a KD of 4.8 μM (FIG. 9K) and showed potent inhibitory effects at this concentration range (FIG. 9I-J).

Example 7: Therapeutic Preparations of Low-Molecular Weight Heparins Protect LDLR Against PCSK9 Induced Degradation HepG2 cells incubated overnight with the low-molecular weight heparin preparation fragmin (1-100 U/ml) or Innohep (1-100 U/ml) showed increased levels of LDLR as evaluated by Western blotting (FIG. 8A). The effect of fragmin and Innohep were comparable to the effect of heparin (FIG. 5A) and the penta-saccharide Arixtra (FIG. 7).

These results show that structure-based drug design using the heparin:PCKS9 complex as a template is a feasible approach in the development of a small molecule PCSK9 inhibitor.

Example 8: Heparin Protects the LDLR Against PCSK9 Induced Degradation In Vivo Mice (BALB6/cJRj) were subjected to a single intravenous administration (tail vein) of 10 µg human recombinant PCSK9 alone or in combination with heparin (50 U). One hour post injection mice were sacrificed and liver tissues were collected. Western blot analysis of LDLR in membrane protein preparations showed a significant higher level of liver LDLR in mice co-injected with heparin compared to mice injected with PCSK9 alone (FIG. 8B, quantified in FIG. 8C).

These results show that the PCSK9:heparin interaction may provide a framework for the development of small molecule PCSK9 inhibitors.

Example 9: Polyclonal Antibodies Directed Against the HSPG Binding of PCSK9 Inhibit PCSK9 Activity Polyclonal antibodies were produced by immunization of three rats with DNA encoding chimeric rat PCSK9 containing the human HSPG binding domain. Serum samples obtained from immunized animals were tested for PCSK9-binding antibodies by immunoprecipitation.

Antibodies from 1 µl immune or preimmune rat serum were immobilized on GammaBind beads (GE Healthcare), and used for precipitation (3h at 4 □ C) of 35S human PCSK9 from conditioned media of metabolically labeled HEK293 transiently transfected with PCSK9 as described previously (Gustafsen et al., 2014). Following 3 washes in TBS containing 0.1% Triton X100, precipitated proteins were eluted by boiling samples in NUPAGE sample buffer supplemented with 20 mM dithioerythreitol (DTE), separated by SDS-PAGE, and visualized by phosphorimaging.

Immune serum from all animals specifically precipitated 35-S labeled PCSK9. No pull down of PCSK9 was detected in control immunoprecipitations performed with serum from pre-immune animals (FIG. 8D).

IgG purified from immune and pre-immune serum samples were tested using an in vitro model of PCSK9 induced LDLR degradation in which HepG2 cells incubated with immune IgG showed a markedly increase in LDLR levels (FIG. 8E). These results indicate that antibodies targeting the HSPG binding domain of PCSK9 efficiently inhibit PCSK9 activity.

Example 10: Generation of PCSK9 Inhibitory mAbs Directed at the PCSK9 HSPG Binding Domain Monoclonal antibodies (mAbs) against the HSPG binding domain in PCSK9 were produced by Aldevron Freiburg, Germany by immunization of three rats with DNA encoding chimeric rat PCSK9 containing the human HSPG binding domain. Monoclonal antibody producing hybridoma clones were obtained by fusion of rat spleen lymphocytes with myeloma cells and subsequent single cell subcloning of antibody producing cells before collection of mAb containing hybridoma supernatants. The individual mAbs were tested by immunoprecipitation of 35S human PCSK9 using 500 µl conditioned media from the mAb producing hybridoma clones immobilized on GammaBind beads (GE Healthcare). We found that 16 of 26 tested mAbs specifically precipitated native 35S human PCSK9 (FIG. 8F).

Further functional testing of PCSK9 binding mAbs in HepG2 cells showed that 12 of the clones inhibit PSCK9 activity and increase cellular levels of LDLR approximately two fold (FIG. 8G).

These 12 clones were tested to see whether they can bind an R93R96R97R104R105H139 PCSK9 mutant (FIG. 8H). Four of the clones which were able to increase cellular levels of LDLR by approximately two fold were not able to bind this mutant (compare mAb 1G8, 5E11, 8HA and 10E5 in FIGS. 8F, 8G and 8H). Further testing showed that mAb 10E5 precipitates WT PCSK9, as well as variants R96R97 and R104R105 (FIG. 8I), whereas mAbs 1G8 and 5E11 recognize only WT PCSK9 (FIG. 8I). These results demonstrate that these three clones specifically bind to the HSPG binding domain.

Clones 5E11 and 8HA were sequenced (SEQ ID NO: 2, 4, 6 and 8).

Example 11: Generation of Humanized Monoclonal Antibodies for Clinical Testing Monoclonal antibodies are generated by immunization of rats with DNA encoding a chimeric protein composed of rat PCSK9 and the human PCSK9 HSPG binding motif, candidate antibodies are found by screening for binding to human PCSK9 in an ELISA assay. Candidate antibodies are characterized with respect to epitope, affinity to human PCSK9 and recognition of native PCSK9. Selected candidate antibodies are tested for their ability to inhibit PCSK9 function in a HepG2 cell culture assay and the most promising antibody is tested in a transgenic mouse expressing human PCSK9 under the control of the endogenous murine PCSK9 promoter. Upon administration, analysing LDL receptor levels in the liver and cholesterol in plasma will assess the PCSK9 neutralizing effect of the antibody. The lead candidate is humanized and prepared for clinical testing.

Example 12: Reducing LDL Cholesterol Using an Antibody Directed Against the HSPG Binding Site of PCSK9

A patient with elevated LDL cholesterol levels is prescribed an active compound consisting of a humanized antibody directed against the HSPG binding site in human PCSK9. The patient receives subcutaneous injections of 25-500 mg of the composition at intervals of 1-28 days. Marked reductions in LDL-C levels are observed. These data show that parenteral administration of an antibody directed against the HSPG binding site in human PCSK9 can lead to reduction in LDL-C levels in a subject.

Example 13: Reducing LDL Cholesterol in a Patient not Responding to Statin Treatment A patient with elevated LDL cholesterol is prescribed a statin treatment. The patient does not respond to the statin treatment. The patient is then prescribed a treatment with subcutaneous injections of 25-500 mg of a composition comprising a humanized antibody directed against the HSPG binding site in human PCSK9. The injections take place at intervals of 1-28 days. Marked reductions in LDL-C levels are observed, showing that parenteral administration of an antibody directed against the HSPG binding site in human PCSK9 can lead to reduction in LDL-C levels in a patient non-responsive to statin treatment.

Example 14: Reducing LDL Cholesterol Using a Small Molecule Compound Directed Against the HSPG Binding Site of PCSK9

A patient with elevated LDL cholesterol levels is prescribed administration of a small molecule compound that is designed to block the HSPG binding site in human PCSK9. The compound is administered orally at a dosis of 0.1-30 mg/kg. Marked reductions in LDL-C levels are observed, showing that oral administration of a small molecule designed to block the HSPG binding site in human PCSK9 can lead to reduction in LDL-C levels in a patient.

Example 15: Generation of Antibodies Against the HSPG Binding Site in PCSK9

A purified mouse PCSK9 chimera is constructed where the mouse HSPG binding sequence stretch is substituted with the human sequence stretch (encompassed within amino acid residues 78 to 167 of SEQ ID NO: 1). A mouse is immunized with the chimera. Clones are subsequently selected by direct ELISA in two steps. In a first step, antibodies able to bind wild-type human PCSK9 are selected using microtiter wells coated with purified wild-type, human PCSK9. In a second selection step, microtiter wells are coated with mutant, human PCSK9 unable to bind HSPG. Antibodies able to bind the mutant PCSK9 are selected. The affinity of selected antibodies against immobilized human PCSK9 is evaluated by determining their $K_d$. Antibodies are subsequently tested for their ability to inhibit PCSK9-induced LDLR degradation in HepG2 cells.

Antibodies directed to the HSPG binding domain of human PCSK9 and capable of inhibiting PCSK9-induced LDLR degradation are thus selected.

Example 16: Selection of Antibodies Directed Against the HSPG Binding Site Using Biacore The affinity and specificity of antibodies directed against the HSPG binding site in PCSK9 are evaluated using surface plasmon resonance performed on a Biacore 3000 Instrument equipped with CM5 sensor chips activated as described (Munck Petersen et al., 1999). Wild-type human PCSK9 or human mutant PCSK9 unable to bind HSPG are immobilized to densities 74-83 fmol/mm$^2$ in 10 mM sodium acetate, pH 4.0, and the remaining coupling sites are blocked with 1 M ethanolamine. Antibody samples are injected at 5 μl/min at 25° C. in 10 mM HEPES, pH 7.4, 150 mM NaCl, 1.5 mM $CaCl_2$, 1 mM EGTA, and 0.005% Tween 20 (CaHBS). Binding is expressed in relative response units (RU), calculated as the difference in response between the immobilized protein flow cell and the corresponding control flow cell. Kinetic parameters are determined, e.g. using BIA evaluation 4.1.

Example 17

PCSK9 mAbs directed against the HSPG binding domain is tested using a coronary artery disease mouse model heterozygote for LDLR (LDLR+/−) with expression of human PCSK9 under control of the endogenous murine PCSK9 promoter. Western type diet fed animals is treated with PCSK9 mAb (10 mg/kg) every third week for a time period of 6-8 months. At the end of the experiment mice are sacrificed and atherosclerotic lesions in aorta are evaluated by microscopy. Plasma LDL-c is evaluated by ELISA every second months during the experiment.

Example 18: Combination Therapy Using Antibodies Directed Against the HSPG and LDLR Binding Sites A humanized antibody directed to the HSPG-binding domain of PCSK9 (among amino acids 78 to 167 of SEQ ID NO: 1) is used in combination with an antibody inhibiting binding of PCSK9 to the LDLR. A synergistic effect is observed, whereby lower amounts of each antibody need to be administered, leading to reduced side-effects.

Example 19: Reducing LDL Cholesterol in a Patient not Responding to Statin Treatment A patient receives statin treatment against elevated LDL-C levels. However, after an initial drop in LDL-C levels, and due to the statin-induced increased expression of PCSK9, the treatment does not succeed in significantly reducing LDL-C levels.

In addition to the statin, the patient is administered a compound inhibiting binding of HSPGs to PCSK9. The administration occurs weekly and with a low dose (25-150 mg) of the compound in combination with statins. Marked reductions in LDL-C levels are observed, and the desired level of LDL-C is reached.

This example shows that supplementing a statin-based treatment with administration of an antibody directed against the HSPG-binding domain of PCSK9 can successfully reduce LDL-C levels.

Example 20: PCSK9 with Mutated HSPG Binding Site Fails to Increase LDL Cholesterol Levels Wild-type PCSK9 and HSPG-binding mutants of PCSK9 are over-expressed in mouse livers by hydrodynamic tail injection of expression plasmids free of CG dinucleotides (Invivogen); these plasmids exhibit long term expression as compared to conventional plasmids that are prone to inactivation by methylation of CG base pairs. Over-expression of wild-type PCSK9 induces enhanced degradation of LDLR, resulting in elevated serum LDL cholesterol and thereby behaving as a "gain of function" variant. The HSPG mutants of PCSK9 behave as "loss of function" variants giving rise to less elevated serum LDL cholesterol levels due to reduced degradation of the LDL receptor.

The results demonstrate the pivotal role of the PCSK9 HSPG-binding domain for the degradation of the LDL receptor in animals.

Example 21: Structure-Based Drug Design of Small Molecule PCSK9 Inhibitors Based on the Interaction of PCSK9 with Heparin and Heparin Mimetics Candidate compounds selected among low molecular weight heparins and heparin mimetics are tested for their ability to inhibit PCSK9 function and increase LDLR levels in a HepG2 cell culture assay. The heparin analogue fondaparinux (trade name Arixtra) is used as the reference compound. The structural information obtained is used to derive 3-5 pharmacophore models, which are used to screen an existing database of 3 million purchasable compounds. A diversity-based collection of 50 compounds is selected for functional testing in HepG2 cells. Successful inhibitors facilitate calibration of the molecular docking model and a second screening of purchasable compounds. Fifty compounds are selected for purchase and in vitro testing. The three most promising candidates are subsequently tested in a mouse model to evaluate in vivo effect on LDLR levels in the liver and cholesterol in plasma.

Example 22: Testing of PCSK9 Inhibitor Candidates

Preclinical testing of PCSK9 inhibitor candidates is performed using a coronary artery disease mouse model heterozygote for LDLR (LDLR+/−) with expression of human PCSK9 under control of the endogenous murine PCSK9 promoter. Western type diet fed animals is treated with PCSK9 inhibitors for a time period of 6-8 months, before evaluation of atherosclerotic plaque area by microscopy after oil red 0 staining of fat deposits in dissected aorta. The plasma concentration of cholesterol is assessed by ELISA every second month during the experiment.

These studies will allow evaluation of the ability of PCSK9 inhibitor candidates to lower serum cholesterol.

Example 23: Suramin Protects LDLR from PCSK9-Induced Degradation

Suramin belongs to the class of non-carbonhydrate-based sulphated heparin mimetics and show overlapping binding site with heparin in a structural model of its complex with thrombin (Lima et al., 2009). The PCSK9 inhibitory effect of overnight incubation with suramin (0-200 µg/ml) was tested in HepG2 cells (FIG. 9 A-B). The LDLR level was 15 times up regulated in cells with the highest tested concentration of suramin (200 µg/ml), suggesting that suramin potently protects the LDLR from PCSK9 induced degradation.

Example 24: Effect of Suramin on Liver LDLR Levels

In vivo testing of suramin is performed with mice on Western-type diet subjected and with mice that were not subjected to a Western-type diet to a single intravenous administration (tail vein) of 5-20 µg human recombinant PCSK9 alone or in combination with 50-200 µg suramin. Groups of 5-7 mice are sacrificed to evaluate liver LDLR levels (1 hour post injection) by Western blot analysis and plasma LDL-c (7 hours post injection) by ELISA.

These studies will confirm that administration of suramin leads to increased LDLR levels in vivo.

Example 25: Dextran Sulphate and Pentosan Protect LDLR from PCSK9-Induced Degradation In the heparin mimetic class of modified polysaccharides compounds dextran sulfate (FIGS. 9 A-B) and pentosan (FIG. 9 D-E) were tested in a HepG2 based in vitro cell assay. After overnight incubation LDLR levels were evaluated by Western blotting showing a concentration dependent increase of LDLR upon treatment with dextran sulfate (0-200 µg/ml) with up to 3-fold up regulation of LDLR. Pentosan (0-200 µg/ml) incubation resulted in 4 fold increase LDLR at concentrations from 50 µg/ml.

Example 26: Effect on Pentosan on Liver LDLR Levels

Pentosan-polysulfate is injected into mice expressing human PCSK9 to evaluate the ability of the substance to protect the LDLR against PCSK9 induced degradation.

These studies will confirm that administration of pentosan leads to increased LDLR levels in vivo.

Example 27: Effect of Pentosan on Serum Cholesterol Levels

Patients with elevated serum cholesterol are treated with oral or subcutaneous injection of Pentosan-polysulfate to evaluate the ability of the substance to lower serum cholesterol. Pentosan-polysulfate is absorbed from the digestive tract with a median of 2 hours after ingestion of an oral dose according to the manufacturer. Cholesterol levels are then measured.

These studies will confirm that pentosan leads to decreased serum cholesterol levels.

Example 28: The Phosphorothioate Oligonucleotide S-dC-36 Protects LDLR from PCSK9-Induced Degradation HepG2 cells incubated with oligonucleotide s-dC-36 (0.5-5.0 µM) (FIG. 9 I-J) showed increased levels of cellular LDLR protein (2-fold increase at 5.0 µM S-dC-36). S-dC-36 belongs the heparin mimetic class of phosphorothioate oligonucleotides, and the data suggests that S-dC-36 efficiently protects the LDLR from PCSK9 induced degradation.

Example 29: Determination of Optimal Length of Phosphorothioate Oligonucleotide for LDLR Protection Phosphorothioate oligonucleotides bind to heparin binding proteins and inhibit their functions. The ability of phosphorothioate oligonucleotides to bind nonspecifically to a variety of proteins has been well documented (Yakubov et al, 1993; Stein 1995). Antisense phosphorothioate oligonucleotides are normally designed to have the complementary base sequence for binding the target mRNA specifically and thereby induce degradation of the mRNA.

The optimum length of the phosphorothioate oligonucleotide for binding to PCSK9 and thereby protecting the LDLR from degradation is determined in cell culture assays using the HepG2 cell line. The base sequence of the phosphorothioate oligonucleotide is chosen in order to have minimal effect on gene expression in variety of cell lines and tissues.

Example 30: Effect of Optimized Phosphorothioate Oligonucleotide on LDLR Protection An optimized phosphorothioate oligonucleotide is injected into mice expressing human PCSK9 to evaluate the ability of the substance to protect the LDLR against PCSK9 induced degradation.

Example 31: Effect of Optimized Phosphorothioate Oligonucleotide on Serum Cholesterol Levels An optimized phosphorothioate oligonucleotide is injected into patients having elevated serum cholesterol to evaluate the ability of the substance to lower serum cholesterol.

Example 32: Effect of Mipomersen on LDLR Levels

HepG2 cells are incubated with Mipomersen to evaluate the ability of the substance to increase levels of the LDLR.

Mipomersen is an apoB100 antisense modified phosphorothioate oligonucleotide and cholesterol-reducing drug. It is an antisense therapeutic that targets the messenger RNA for apolipoprotein B100. It is administered as a weekly injection for familial hypercholesterolemia.

These studies will show that Mipomersen leads to increased LDLR levels.

Example 33

ApoE-/- mice treated with suramin or PPDAS (pyridoxal-phosphate-6-azophenyl-2'-4'-disulphonic acid) are tested for up regulation of liver LDLR levels. Suramin and PPDAS have been reported to reduce plaque size in apoE-/- mice (Guns et al., 2009).

Example 34

ApoE-/- mice treated with suramin are tested for up regulation of liver LDLR levels. Suramin has been reported to reduce plaque size in apoE-/- mice (Guns et al., 2009).

Example 36

In contrast to ATP, the P2Y6-selective agonist UDP increases mRNA expression and activity of inducible nitric oxide synthase and interleukin-6 in J774 macrophages; this effect is blocked by suramin (100-300 mM) or pyridoxal-phosphate-6-azophenyl-2'-4'-disulphonic acid (PPADS, 10-30 mM). Finally, 4-week treatment of cholesterol-fed apoE-/- mice with suramin or PPADS (50 and 25 mg·kg-1·day-1 respectively) reduces plaque size, without changing plaque composition (relative SMC and macrophage content) or cell replication.

Example 37

The in vivo effect of mAb 5E11 is tested in 10-12 week-old male BALB6/cJRj mice. Mice are injected intravenously (tail vein) with 0.9% saline (vehicle control) or PCSK9 (10 μg) with or without 5E11 (50-250 μg). In one experiment mice are harvested 1 hour after injection and liver LDLR levels are evaluated by Western blotting. In a parallel experiment mice are injected with a comparable amount of 1:1 mixture of 5E11 and and antibody directed against the LDL receptor binding site in PCSK9 to evaluate the effect of PCSK9 inhibition targeting both the LDLR and the HSPG binding site. Plasma LDL-c concentrations are evaluated by ELISA at specific time points following injection. Similar experiments are carried out using mAb 8H4.

SEQUENCES

SEQ ID NO: 1: PCSK9 protein-NCBI accession number: NG_009061.1
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEEDGTRFHRQASKCDSHGTHLAGVVSGRDAGVAKGASMRSL

RVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGT

LGTNFGRCVDLFAPGEDIIGASSDCSTCFVSQSGTSQAAAHVAGIAAMML

SAEPELTLAELRQRLIHFSAKDVINEAWFPEDQRVLTPNLVAALPPSTHG

AGWQLFCRTVWSAHSGPTRMATAVARCAPDEELLSCSSFSRSGKRRGERM

EAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASC

CHAPGLECKVKEHGIPAPQEQVTVACEEGWTLTGCSALPGTSHVLGAYAV

DNTCVVRSRDVSTTGSTSEGAVTAVAICCRSRHLAQASQELQ*

SEQ ID NO: 2 (3), 4 (5), 6 (7) and 8 (9) were obtained by sequencing of the variable regions of the immunoglobulin genes expressed by rat hybridomas BNT-8H4-B8/C7-E11, BNT-5E11-D4/G1-E4, as indicated.

SEQ ID NO: 2: BNT-8H4-B8/C7-E11_VK DNA
gatattgtga tgacccagtc tccctcactc ctgtctgcat ctgtgggaga cagagtcact cttagctgca aaggaagtca gaatattaac aattacttag cctggtacca acaaaagctc ggagaagctc ccaaactcct gatctataat acaaacagtt tacaaacggg catcccatca aggttcagtg gcagtggatc tggtacagat tgcacactca ccatcagaag cctgcagcct gaagatgttg ccacatattt ctgctatcag tataacaacg ggaacacgtt tggaggtggg accaagctgg agctgaaa

| LOCUS BNT-8H4-B8/C7-E11_VK 318 bp DNA linear | |
|---|---|
| FEATURES | Location/Qualifiers |
| J_segment | 289.318 /label = JK |
| V_region | 169.264 /label = FWR3 |
| V_region | 103.147 /label = FWR2 |
| V_region | 1.69 /label = FWR1 |
| V_segment | 70.102 /label = CDR1 |
| V_segment | 148.168 /label = CDR2 |
| V_segment | 265.288 /label = CDR3 |
| CDS | 1.318 /label = VK |

SEQ ID NO: 3: BNT-8H4-B8/C7-E11_VK DNA
DIVMTQSPSLLSASVGDRVTLSCKGSQNINNYLAWYQQKLGEAPKLLIYN
TNSLQTGIPSRFSGSGSGTDCTLTIRSLQPEDVATYFCYQYNNGNTFGGG
TKLELK

SEQ ID NO: 4: BNT-5E11-D4/G1-E4_VK DNA
gatgttgtgt tgacacaaac tccagttttc ctgtctgtca cacttggaga tcagacttct atatcttgta ggtctagtca gagtctggaa tatagtgatg gatacactta tttggaatgg tacctacaga aaccgggcca gtctccacag ctcctcatct atgaagtttc caaccgattt tctggggtcc cagacaggtt cattggcagt gggtcaggga cagatttcac cctcaagatc -continued

```
agcagagtag agcctgagga cttgggagtt tattactgct tccaaggtac acatgatcct ctcacgttcg gttctgggac caagctggag atcaaa
```

| LOCUS BNT-5E11-D4/G1-E4_VK 336 bp DNA linear | |
|---|---|
| FEATURES | Location/Qualifiers |
| J_segment | 307..336 /label = JK |
| V_region | 184..279 /label = FWR3 |
| V_region | 118..162 /label = FWR2 |
| V_region | 1..69 /label = FWR1 |
| V_segment | 70..117 /label = CDR1 |
| V_segment | 163..183 /label = CDR2 |
| V_segment | 280..306 /label = CDR3 |
| CDS | 1..336 /label = VK |

SEQ ID NO: 5: BNT-5E11-D4/G1-E4_VK protein
DVVLTQTPVFLSVTLGDQTSISCRSSQSLEYSDGYTYLEWYLQKPGQSPQ
LLIYEVSNRFSGVPDRFIGSGSGTDFTLKISRVPEDLGVYYCFQGTHDP
LTFGSGTKLEIK

SEQ ID NO: 6: BNT-5E11-D4/G1-E4_VH DNA

| LOCUS BNT-5E11-D4/G1-E4_VH 336 bp DNA linear | |
|---|---|
| FEATURES | Location/Qualifiers |
| J_segment | 304..336 /label = JH |
| V_region | 199..294 /label = FWR3 |
| V_region | 109..150 /label = FWR2 |
| V_region | 1..90 /label = FWR1 |
| V_segment | 91..108 /label = CDR1 |
| V_segment | 151..198 /label = CDR2 |
| V_segment | 295..303 /label = CDR3 |
| CDS | 1..336 /label = VH |

```
gaggtgcagc tgcaggagtc aggacctggc cttgtgaaac cttcacagtc actctccctc acctgttctg tcactggtta caccattacc agtggttatg attggagctg gatccgagg ttcccaggaa atacaatgga gtggatggga gacataagtt acagtggtag cactaactac aacccatcgc tcaaaagtcg agtctccatt acaagagaca catccaagaa tcagttcttc ctgcagttga actctgtaac tactggggat acagccacat attactgtgc aaaactaccc ggctgggggcc aaggcactct ggtcactgtc tcttca
```

SEQ ID NO: 7: BNT-5E11-D4/G1-E4_VH protein
EVQLQESGPGLVKPSQSLSLTCSVTGYTITSGYDWSWIRRFPGNTMEWMG
DISYSGSTNYNPSLKSRVSITRDTSKNQFFLQLNSVTTGDTATYYCAKLP
GWGQGTLVTVSS

SEQ ID NO: 8: BNT-8H4-B8/C7-E11_VH DNA

| LOCUS BNT-8H4-B8/C7-E11_VH 354 bp DNA linear 09-MAR-2016 | |
|---|---|
| FEATURES | Location/Qualifiers |
| J_segment | 322..354 /label = JH |
| V_region | 202..297 /label = FWR3 |
| V_region | 112..153 /label = FWR2 |
| V_region | 1..90 /label = FWR1 |
| V_segment | 91..111 /label = CDR1 |
| V_segment | 154..201 /label = CDR2 |
| V_segment | 298..321 /label = CDR3 |
| CDS | 1..354 /label = VH |

```
caggttactc tgaaagagtc tggccctggg atattgcagc cttcccagac cctcagtctg acttgctctt tctctgggtt ttcactgagc agttcaggta tatgtgtgag ctggattcgt cagccttcag ggaagggtct ggagtggctg gcaactattt gttgggagga tagtaaggcc tacaaccctt ctctgaagaa ccggctcacg atctccaagg acacctccaa caaccaagca ctcctcagga tcaccagtgt ggacactgca gataccgcca tttactactg tgctcgggtt tattactggt actttgactt ctggggccca ggaaccatgg tcaccgtgtc ctca
```

SEQ ID NO: 9: BNT-8H4-B8/C7-E11_VH protein
QVTLKESGPGILQPSQTLSLTCSFSGFSLSSSGICVSWIRQPSGKGLEWL
ATICWEDSKGYNPSLKNRLTISKDTSNNQALLRITSVDTADTAIYYCARV
YYWYFDFWGPGTMVTVSS SEQ ID NO: 10-CDR1 of SEQ ID NO: 7
SGYDWS SEQ ID NO: 11-CDR2 of SEQ ID NO: 7
DISYSGSTNY NPSLKS SEQ ID NO: 12-CDR3 of SEQ ID NO: 7
LPG SEQ ID NO: 13-CDR1 of SEQ ID NO: 5
RSSQSLEYSD GYTYLE SEQ ID NO: 14-CDR2 of SEQ ID NO: 5
EVSNRFS SEQ ID NO: 15-CDR3 of SEQ ID NO: 5
FQGTHDPLT SEQ ID NO: 16-CDR1 of SEQ ID NO: 9
SSGICVS SEQ ID NO: 17-CDR2 of SEQ ID NO: 9
TICWEDSKGY NPSLKN SEQ ID NO: 18-CDR3 of SEQ ID NO: 9
VYYWYFDF SEQ ID NO: 19- DR1 of SEQ ID NO: 3
KGSQNINNYLA SEQ ID NO: 20-CDR2 of SEQ ID NO: 3
NTNSLQT SEQ ID NO: 21-CDR2 of SEQ ID NO: 3
YQYNNGNT

REFERENCES

Benimetskaya et al. (1995) Nucleic Acids Res 23: 4239-4245 Bird et al. (1988) Science 242:423-426.
Chan et al. (2009) Proc Natl Acad Sci USA. 2009 Jun. 16; 106(24):9820-5. doi: 10.1073/pnas.0903849106
Cunningham et al. (2007) Nat Struct Mol Biol. 14(5): p. 413-9.
Fisher et al. (2007) J Biol Chem. 282(28): p. 20502-12.
Greenberg A S, Avila D, Hughes M, Hughes A, McKinney E C, Flajnik. (1995) Nature. 374, 168-173.
Guns et al., 2009. British Journal of Pharmacology (2010), 159, 326-336
Gustafsen et al. (2014) Cell Metab 19(2): p. 310-8
Hamers-Casterman C, Atarhouch T, Muyldermans S, et al. (1993) Nature. 363(6428):446-8.
Herbert et al., Circ Res 79, 590-600 (1996).
Hollinger et al. (1993) Proc. Natl. Acad. Sci. USA 90: 6444-6448.
Huston et al. (1988) Proc. Natl. Acad. Sci. USA 85:5879-5883.
Jerabek-Willemsen et al. (2011) Assay Drug Dev Technol. 9(4): p. 342-53.
Kohler and Milstein (1975) Nature 256:495.
Lagace et al. (2006) J Clin Invest. 2006 November; 116(11): 2995-3005
Lakoski et al. (2009) J Clin Endocrinol Metab. 94(7): p. 2537-43.
Lima et al., Biochim Biophys Acta. 2009 June; 1794(6): 873-81.
Lonberg, N. et al. (1994) Nature 368 (6474):856-859.
Munck Petersen et al (1999) EMBO J 18(3):595-604.
McCoy, A. J., et al., Structure of beta-antithrombin and the effect of glycosylation on antithrombin's heparin affinity and activity. J Mol Biol, 2003. 326(3): p. 823-33.
Nour-Eldin H H, Hansen B G et al. (2006) Nucleic Acids Res. 34(18):e122.
Piper et al. (2007). Structure, 2007. 15(5): p. 545-52.
Reiter Y, Brinkmann U, et al. (1994) J. Biol. Chem. 269 (15):18327-31.
Seidah et al. (2014) Circ Res. 2014 Mar. 14; 114(6):1022-36. doi: 10.1161/CIRCRESAHA.114.301621
Sheridan (2013). Nat Biotechnol. 2013 December; 31(12): 1057-8. doi: 10.1038/nbt1213-1057.
Soderberg et al., Nat Methods 3, 995-1000 (2006).
Stein et al. (1995) Nat Med 1: 1119-1121.
Villiers B R, Stein V, Hollfelder F. (2010) Protein Eng Des Sel. 23(1):1-8.
Ward E S, Güssow D, Griffiths A D, Jones P T, Winter G. (1989) Nature 341:544-546.
Wozniak-Knopp G, Stadlmann J, Ruker F (2012) PLoS ONE 7(1): e30083.
Yabukov et al. (1993) J Biol Chem. 268(25):18818-23.
Xu and Esko (2014) Annu Rev Biochem. 2014; 83:129-57

The invention claimed is:

1. An antibody or antigen-binding fragment thereof that specifically binds a binding region within the HSPG binding site of PCSK9 (SEQ ID NO: 1), said site within amino acid residues 78 to 167 of PCSK9 (SEQ ID NO: 1), wherein:

(a) the antibody or antigen-binding fragment thereof comprises:

(i) a heavy chain variable region or a humanized version thereof, comprising three CDRs, wherein heavy chain CDR1 comprises SEQ ID NO: 10: heavy chain CDR2 comprises SEQ ID NO: 11; and heavy chain CDR3 comprises SEQ ID NO: 12, and (ii) a light chain variable region or a humanized version thereof, comprising three CDRs, wherein light chain CDR1 comprises SEQ ID NO: 13; light chain CDR2 comprises SEQ ID NO: 14; and light chain CDR3 comprises SEQ ID NO: 15; or
(b) the antibody or antigen-binding fragment thereof comprises:
(i) a heavy chain variable region or a humanized version thereof, comprising three CDRs, wherein heavy chain CDR1 comprises SEQ ID NO: 16; heavy chain CDR2 comprises SEQ ID NO: 17; and heavy chain CDR3 comprises SEQ ID NO: 18, and
(ii) a light chain variable region or a humanized version thereof, comprising three CDRs, wherein light chain CDR1 comprises SEQ ID NO: 19; light chain CDR2 comprises SEQ ID NO: 20; and light chain CDR3 comprises SEQ ID NO: 21.

2. The antibody or antigen-binding fragment of claim 1 comprising a heavy chain variable region or a humanized version thereof as defined by SEQ ID NO: 7 and a light chain variable region or a humanized version thereof as defined by SEQ ID NO: 5.

3. The antibody or antigen-binding fragment of claim 1, wherein the antibody or antigen-binding fragment thereof comprises a heavy chain variable region or a humanized version thereof as defined by SEQ ID NO: 9 and a light chain variable region or a humanized version thereof as defined by SEQ ID NO: 3.

4. The antibody or antigen-binding fragment of claim 1 wherein said site is within the HSPG binding site of PCSK9 (SEQ ID NO: 1) at amino acid residues 78 to 92, amino acid residues 93 to 97, amino acid residues 98 to 103, amino acid residues 104 to 105, amino acid residues 106 to 135, amino acid residues 136 to 139, amino acid residues 140 to 164, and/or amino acid residues 165 to 167.

5. A method of treatment of a disorder of lipoprotein metabolism in a subject in need thereof, said method comprising administering to said subject the antibody or antigen-binding fragment as defined in claim 1.

6. The method according to claim 5, wherein the disorder of lipoprotein metabolism is dyslipidemia.

7. The method according to claim 6, wherein the dyslipidemia is hypercholesterolemia, hyperlipidemia or hypertriglyceridemia.

8. The method according to claim 5, wherein the disorder of lipoprotein metabolism is selected from the group consisting of sitosterolemia, metabolic syndrome, xanthoma, obesity and diabetes.

9. The method according to claim 5, wherein the disorder of lipoprotein metabolism is coronary heart disease.

10. The method according to claim 5, wherein the disorder of lipoprotein metabolism is selected from the group consisting of atherosclerosis, arteriosclerosis, acute coronary syndrome, hypertension, angina, and vascular inflammation.

* * * * *